United States Patent
Singh et al.

(10) Patent No.: US 10,669,593 B2
(45) Date of Patent: Jun. 2, 2020

(54) GENE CONTROLLING FRUIT COLOR PHENOTYPE IN PALM

(71) Applicant: Malaysian Palm Oil Board, Kajang (MY)

(72) Inventors: Rajinder Singh, Kuala Lumpur (MY); Leslie Ooi Cheng Li, Kuala Lumpur (MY); Leslie Low Eng Ti, Kuala Lumpur (MY); Rahimah Abdul Rahman, Selangor (MY); Meilina Ong Abdullah, Seremban (MY); Jayanthi Nagappan, Malacca (MY); Rozana Rosli, Kluang (MY); Mohd Amin Ab. Halim, Selangor (MY); Rajanaidu Nookiah, Kuala Lumpur (MY); Chan Kuang Lim, Seremban (MY); Norazah Azizi, Alor Setar (MY); Ravigadevi Sambanthamurthi, Selangor (MY); Rob Martienssen, Cold Spring Harbor, NY (US); Steven W. Smith, Fitchburg, WI (US); Nathan D. Lakey, Chesterfield, MO (US); Andrew Van Brunt, St. Louis, MO (US); Jared Ordway, St. Louis, MO (US); Michael Hogan, Ballwin, MO (US); Chunyan Wang, Ballwin, MO (US)

(73) Assignee: Malaysian Pal Oil Board, Selangor (MY)

( * ) Notice: Subject to any disclaimer, the term of this patent is extended or adjusted under 35 U.S.C. 154(b) by 786 days.

(21) Appl. No.: 14/226,508

(22) Filed: Mar. 26, 2014

(65) Prior Publication Data

US 2014/0302497 A1 Oct. 9, 2014

Related U.S. Application Data

(60) Provisional application No. 61/809,767, filed on Apr. 8, 2013.

(51) Int. Cl.
*C12Q 1/6827* (2018.01)
*C12Q 1/6895* (2018.01)

(52) U.S. Cl.
CPC ......... *C12Q 1/6895* (2013.01); *C12Q 1/6827* (2013.01); *C12Q 2600/156* (2013.01)

(58) Field of Classification Search
None
See application file for complete search history.

(56) References Cited

FOREIGN PATENT DOCUMENTS

| WO | WO 2001/48224 A1 | 7/2001 |
|---|---|---|
| WO | WO 2001/51627 A2 | 7/2001 |
| WO | 2009/061214 A1 | 5/2009 |

OTHER PUBLICATIONS

Baker et al. Systematic Biology 58.2 (2009): 240-256.*
Barcelos et al. Pesq. agropec. bras., Brasilia, v. 37, n. 8, p. 1105-1114, 2002.*
GenBank Accession No. GH159178.1, created Nov. 30, 2009.*
Billotte et al. Theor Appl Genet (2005) 110: 754-765.*
EMBL Accession No. AJ578630, created Jul. 31, 2004.*
Sambanthamurthi et al. Breeding Plantation Tree Crops: Tropical Species, Chapter 10, 377-421, 2009.*
GenBank Submission CF802307, Dec. 28, 2010. http://www.ncbi.nlm.nih.gov/nucest/cf802307.
Ooi et al., "A 1536-plex Oil Palm SNP Set for Genetic Mapping and identification of markers Associateed with Oil Palm Fruit Colour", Plant and Animal Genome XX, Poster Abstract (Jan. 14-18, 2012).
International Search Report and Written Opinion dated Sep. 10, 2014 for International Patent Application No. PCT/US14/31867, 13 pages.
Abdullah, M.Z. et al., "Color Vision System for Ripeness Inspection of Oil Palm Elaeis Guineensis," Journal of Food Processing Preservation, 26 (2002) pp. 213-235.
Singh, R. et al., "The Oil Palm VIRESCENS Gene Controls Fruit Colour and Encodes a R2R3-MYB," Nature Communications, 5:4106 (2014) pp. 1-8.

* cited by examiner

*Primary Examiner* — Charles Logsdon
(74) *Attorney, Agent, or Firm* — Kilpatrick Townsend & Stockton LLP

(57) ABSTRACT

Methods, compositions, and kits for predicting and controlling fruit color in palm.

14 Claims, 26 Drawing Sheets

Specification includes a Sequence Listing.

**a. Wild-type *VIR* cDNA sequence**

ATGGGTAATTTGCGTGCCGAAGTCCAACGTCCAGCTGGTGTTCGCAAAGGAGCATGGAGTGAAGAGGAGG
ACAGGCTTCTGAGAAAGTGCGTTGAGAAATATGGCGAAGGGAACTGGCGCCATGTTCCCCAAAGGGCAGG
CCTCAGAAGGTGCCGAAAGAGCTGCCGACTACGGTGGTTGAACTATCTCAGCCCTAGGATCAACAGGGAG
AAATTTTCGGAGGAAGAAACAGATCTTATCATCAGGCTTCATAAGCTCTTGGGCAACAG**GTGGTCATTAA
TTGCAGGTAGGCTTCCAGGCAGGACAGCAAATGACATCAAGAACTACTGGAACACTCACCTGGGCAAGAA
AGTAGAAGTTGAAAACAAGAAGGCGGAGCCCAGTGCTGATGCCAAAGTAATTAAGCCACGGCCATGGAAA
GTACCGTTGCAATGGTTATGGTCAGAAGATCAGCAATCATGTGGAAGCCAGCAGCCGCAAGAAAAGTTTG
GGATACCAGAACTACCGACAATCTCAGAGAACGATGAAGCGTGGCTGAATTGTATAATGAATGGAGATAG
AGAGAACAGTGCAGTGCCAGACGTTGGAAACGGGAGCACAATGAACCTGCAGAATGAATTTGGAATCGGA
GGCTTGGAGGAAAATAGAGATGGGGCAGTGTTTCTGGAAGGAGTTCTAGGATGGGATGACTTGCTTTGGG
CCACTATATAGTGCTCATATATGGTAGTGCAATAGTTGCCATTATAAGTTGTTTCGAACTTTAATGCTCC
TGAAATTCCCATGCAAGTATTTAGAGCTTCATATCCTACAAAAAGACAGGAAACGAGACCTTGAAAAAAG
ACTCAGTACCAGAAGGCATCCACTTATTGATTGCTTTTATACTTGCAACATGAAGGAAGCACGCTTTCTC
ACCAAAAAAAAAA** b. Event 1 Exon 3 sequence

GTGGTCATTAATTGCAGGTAGGCTTCCAGGCAGGACAGCAAATGACATCAAGAACTACTGGAACACTCACCTGGGCA
AGAAAGTAGAAGTTGAAAACAAGAAGGCGGAGCCCAGTGCTGATGCCAAAGTAATTAAGCCACGGCCATGGAAAGTA
CCGTTGCAATGGTTATGGTCAGAAGATCAGCAATCATGTGGAAGCCAGCAGCCGCAAGAAAAGTTTGGGATACCAGA
ACTACCGACAATCTCAGAGAACGATGAAGCGTGGCTGAATTGTATAATGAATGGAGATAGAGAGAACAGTGCAGTGC
CAGACGTTGGAAACGGGAGCACAATGAACCTGCAGAATGAATTTGGAATCGGAGGCTTGGAGGAAAAT`tGA`GATGGG
GCAGTGTTTCTGGAAGGAGTTCTAGGATGGGATGACTTGCTTTGGGCCACTATATAGTGCTCATATATGGTAGTGCA
ATAGTTGCCATTATAAGTTGTTTCGAACTTTAATGCTCCTGAAATTCCCATGCAAGTATTTAGAGCTTCATATCCTA
CAAAAAGACAGGAAACGAGACCTTGAAAAAAGACTCAGTACCAGAAGGCATCCACTTATTGATTGCTTTTATACTTG
CAACATGAAGGAAGCACGCTTTCTCACCAAAAAAAAAA c. Event 2 Exon 3 sequence

GTGGTCATTAATTGCAGGTAGGCTTCCAGGCAGGACAGCAAATGACATCAAGAACTACTGGAACACTCACCTGGGCA
AGAAAGTAGAAGTTGAAAACAAGAAGGCGGAGCCCAGTGCTGATGCCAAAGTAATTAAGCCACGGCCATGGAAAGTA
CCGTTGCAATGGTTATGGTCAGAAGATCAGCAATCATGTGGAAGCCAGCAGCCGCAAGAAAAGTTTGGGATACCAGA
ACTACCGACAATCTCAGAGAACGATGAAGCGTGGCTGAATTGTATAATGAATGGAGATAGAGAGAACAGTGCAGTGC
CAGACGTTGGAAACGGGAGCACAATGAACCTGCAGAAT`tAA`TTTGGAATCGGAGGCTTGGAGGAAAATAGAGATGGG
GCAGTGTTTCTGGAAGGAGTTCTAGGATGGGATGACTTGCTTTGGGCCACTATATAGTGCTCATATATGGTAGTGCA
ATAGTTGCCATTATAAGTTGTTTCGAACTTTAATGCTCCTGAAATTCCCATGCAAGTATTTAGAGCTTCATATCCTA
CAAAAAGACAGGAAACGAGACCTTGAAAAAAGACTCAGTACCAGAAGGCATCCACTTATTGATTGCTTTTATACTTG
CAACATGAAGGAAGCACGCTTTCTCACCAAAAAAAAAA d. Event 3 Exon 3 sequence

GTGGTCATTAATTGCAGGTAGGCTTCCAGGCAGGACAGCAAATGACATCAAGAACTACTGGAACACTCACCTGGGCA
AGAAAGTAGAAGTTGAAAACAAGAAGGCGGAGCCCAGTGCTGATGCCAAAGTAATTAAGCCACGGCCATGGAAAGTA
CCGTTGCAATGGTTATGGTCAGAAGATCAGCAATCATGTGGAAGCCAGCAGCCGCAAGAAAAGTTTGGGATACCAGA
ACTACCGACAATCTCAGAGAACGATGAAGCG`TaG`CTGAATTGTATAATGAATGGAGATAGAGAGAACAGTGCAGTGC
CAGACGTTGGAAACGGGAGCACAATGAACCTGCAGAATGAATTTGGAATCGGAGGCTTGGAGGAAAATAGAGATGGG
GCAGTGTTTCTGGAAGGAGTTCTAGGATGGGATGACTTGCTTTGGGCCACTATATAGTGCTCATATATGGTAGTGCA
ATAGTTGCCATTATAAGTTGTTTCGAACTTTAATGCTCCTGAAATTCCCATGCAAGTATTTAGAGCTTCATATCCTA
CAAAAAGACAGGAAACGAGACCTTGAAAAAAGACTCAGTACCAGAAGGCATCCACTTATTGATTGCTTTTATACTTG
CAACATGAAGGAAGCACGCTTTCTCACCAAAAAAAAAA

*FIG. 5* e. Event 4 Exon 3 sequence

GTGGTCATTAATTGCAGGTAGGCTTCCAGGCAGGACAGCAAATGACATCAAGAACTACTGGAACACTCACCTGGGCA
AGAAAGTAGAAGTTGAAAACAAGAAGGCGGAGCCCAGTGCTGATGCCAAAGTAATTAAGCCACGGCCATGGAAAGTA
CCGTTGCAATGGTTATGGTCAGAAGATCAGCAATCATGTGGAAGCCAGCAGCCGCAAGAAAAGTTTGGGATACCAGA
ACTACCGACAATCTCAGAGAACGATGAAGCGTGGCTGAATTGT‑‑
AATGAATGGAGATAGAGAGAACAGTGCAGTGCCAGACGTTGGAAACGGGAGCACAATGAACCTGCAGAATGAATTTG
GAATCGGAGGCTTGGAGGAAAATAGAGATGGGGCAGTGTTTCTGGAAGGAGTTCTAGGATGGGATGACTTGCTTTGG
GCCACTATATAGTGCTCATATATGGTAGTGCAATAGTTGCCATTATAAGTTGTTTCGAACTTTAATGCTCCTGAAAT
TCCCATGCAAGTATTTAGAGCTTCATATCCTACAAAAAGACAGGAAACGAGACCTTGAAAAAGACTCAGTACCAGA
AGGCATCCACTTATTGATTGCTTTTATACTTGCAACATGAAGGAAGCACGCTTTCTCACCAAAAAAAAAA f. Event 5 Exon 3 sequence GTGGTCATTAATTGCAGGTAGGCTTCCAGGCAGGACAGCAAATGACATCAAGAACTACTGGAACACTCAC
CTGGGCAAGAAAGTAGAAGTTGAAAACAAGAAGGCGGAGCCCAGTGCTGATGCCAAAGTAATTAAGCCAC
GGCCATGGAAAGTACCGTTGCAATGGTTTTGGTCAGAAGATCAGCAATCATGTGGAAGCCAGCAGCCGCA
AGAAGATTAATGCTTTGGGCCACTATATAGTGCTTATATATGGGATGACTTGCTTTGGGCCACTATATAG
TGCTTATATATGGTAGTGCAATAG

Figure: Alignment of Wild Type and Five Mutant Alleles

```
RTPAP1_mrna    0  ATGGGTAATTTGCGTGCCGAAGTCCAACGTCCAGCTGGTGTTCGCAAAGG
       SNP_1   0  ATGGGTAATTTGCGTGCCGAAGTCCAACGTCCAGCTGGTGTTCGCAAAGG
       SNP_2   0  ATGGGTAATTTGCGTGCCGAAGTCCAACGTCCAGCTGGTGTTCGCAAAGG
       SNP_3   0  ATGGGTAATTTGCGTGCCGAAGTCCAACGTCCAGCTGGTGTTCGCAAAGG
       SNP_4   0  ATGGGTAATTTGCGTGCCGAAGTCCAACGTCCAGCTGGTGTTCGCAAAGG
       SNP_5   0  ATGGGTAATTTGCGTGCCGAAGTCCAACGTCCAGCTGGTGTTCGCAAAGG
RTPAP1_mrnaAA  0  MetGlyAsnLeuArgAlaGluValGlnArgProAlaGlyValArgLysGl
     SNP_1AA   0  MetGlyAsnLeuArgAlaGluValGlnArgProAlaGlyValArgLysGl
     SNP_2AA   0  MetGlyAsnLeuArgAlaGluValGlnArgProAlaGlyValArgLysGl
     SNP_3AA   0  MetGlyAsnLeuArgAlaGluValGlnArgProAlaGlyValArgLysGl
     SNP_4AA   0  MetGlyAsnLeuArgAlaGluValGlnArgProAlaGlyValArgLysGl
     SNP_5AA   0  MetGlyAsnLeuArgAlaGluValGlnArgProAlaGlyValArgLysGl
                  |---------|---------|---------|---------|---------
                  1         11        21        31        41

RTPAP1_mrna   50  AGCATGGAGTGAAGAGGAGGACAGGCTTCTGAGAAAGTGCGTTGAGAAAT
       SNP_1  50  AGCATGGAGTGAAGAGGAGGACAGGCTTCTGAGAAAGTGCGTTGAGAAAT
       SNP_2  50  AGCATGGAGTGAAGAGGAGGACAGGCTTCTGAGAAAGTGCGTTGAGAAAT
       SNP_3  50  AGCATGGAGTGAAGAGGAGGACAGGCTTCTGAGAAAGTGCGTTGAGAAAT
       SNP_4  50  AGCATGGAGTGAAGAGGAGGACAGGCTTCTGAGAAAGTGCGTTGAGAAAT
       SNP_5  50  AGCATGGAGTGAAGAGGAGGACAGGCTTCTGAGAAAGTGCGTTGAGAAAT
RTPAP1_mrnaAA 50  yAlaTrpSerGluGluGluAspArgLeuLeuArgLysCysValGluLysT
     SNP_1AA  50  yAlaTrpSerGluGluGluAspArgLeuLeuArgLysCysValGluLysT
     SNP_2AA  50  yAlaTrpSerGluGluGluAspArgLeuLeuArgLysCysValGluLysT
     SNP_3AA  50  yAlaTrpSerGluGluGluAspArgLeuLeuArgLysCysValGluLysT
     SNP_4AA  50  yAlaTrpSerGluGluGluAspArgLeuLeuArgLysCysValGluLysT
     SNP_5AA  50  yAlaTrpSerGluGluGluAspArgLeuLeuArgLysCysValGluLysT
                  |---------|---------|---------|---------|---------
                  51        61        71        81        91

RTPAP1_mrna  100  ATGGCGAAGGGAACTGGCGCCATGTTCCCCAAAGGGCAGGCCTCAGAAGG
       SNP_1 100  ATGGCGAAGGGAACTGGCGCCATGTTCCCCAAAGGGCAGGCCTCAGAAGG
       SNP_2 100  ATGGCGAAGGGAACTGGCGCCATGTTCCCCAAAGGGCAGGCCTCAGAAGG
       SNP_3 100  ATGGCGAAGGGAACTGGCGCCATGTTCCCCAAAGGGCAGGCCTCAGAAGG
       SNP_4 100  ATGGCGAAGGGAACTGGCGCCATGTTCCCCAAAGGGCAGGCCTCAGAAGG
       SNP_5 100  ATGGCGAAGGGAACTGGCGCCATGTTCCCCAAAGGGCAGGCCTCAGAAGG
RTPAP1_mrnaAA 100 yrGlyGluGlyAsnTrpArgHisValProGlnArgAlaGlyLeuArgArg
     SNP_1AA 100  yrGlyGluGlyAsnTrpArgHisValProGlnArgAlaGlyLeuArgArg
     SNP_2AA 100  yrGlyGluGlyAsnTrpArgHisValProGlnArgAlaGlyLeuArgArg
     SNP_3AA 100  yrGlyGluGlyAsnTrpArgHisValProGlnArgAlaGlyLeuArgArg
     SNP_4AA 100  yrGlyGluGlyAsnTrpArgHisValProGlnArgAlaGlyLeuArgArg
     SNP_5AA 100  yrGlyGluGlyAsnTrpArgHisValProGlnArgAlaGlyLeuArgArg
                  |---------|---------|---------|---------|---------
                  101       111       121       131       141

RTPAP1_mrna  150  TGCCGAAAGAGCTGCCGACTACGGTGGTTGAACTATCTCAGCCCTAGGAT
       SNP_1 150  TGCCGAAAGAGCTGCCGACTACGGTGGTTGAACTATCTCAGCCCTAGGAT
       SNP_2 150  TGCCGAAAGAGCTGCCGACTACGGTGGTTGAACTATCTCAGCCCTAGGAT
       SNP_3 150  TGCCGAAAGAGCTGCCGACTACGGTGGTTGAACTATCTCAGCCCTAGGAT
       SNP_4 150  TGCCGAAAGAGCTGCCGACTACGGTGGTTGAACTATCTCAGCCCTAGGAT
       SNP_5 150  TGCCGAAAGAGCTGCCGACTACGGTGGTTGAACTATCTCAGCCCTAGGAT
RTPAP1_mrnaAA 150 CysArgLysSerCysArgLeuArgTrpLeuAsnTyrLeuSerProArgIl
     SNP_1AA 150  CysArgLysSerCysArgLeuArgTrpLeuAsnTyrLeuSerProArgIl
     SNP_2AA 150  CysArgLysSerCysArgLeuArgTrpLeuAsnTyrLeuSerProArgIl
     SNP_3AA 150  CysArgLysSerCysArgLeuArgTrpLeuAsnTyrLeuSerProArgIl
     SNP_4AA 150  CysArgLysSerCysArgLeuArgTrpLeuAsnTyrLeuSerProArgIl
     SNP_5AA 150  CysArgLysSerCysArgLeuArgTrpLeuAsnTyrLeuSerProArgIl
                  |---------|---------|---------|---------|---------
                  151       161       171       181       191
```

*FIG. 11*

```
RTPAP1_mrna    200 CAACAGGGAGAAATTTTCGGAGGAAGAAACAGATCTTATCATCAGGCTTC
     SNP_1     200 CAACAGGGAGAAATTTTCGGAGGAAGAAACAGATCTTATCATCAGGCTTC
     SNP_2     200 CAACAGGGAGAAATTTTCGGAGGAAGAAACAGATCTTATCATCAGGCTTC
     SNP_3     200 CAACAGGGAGAAATTTTCGGAGGAAGAAACAGATCTTATCATCAGGCTTC
     SNP_4     200 CAACAGGGAGAAATTTTCGGAGGAAGAAACAGATCTTATCATCAGGCTTC
     SNP_5     200 CAACAGGGAGAAATTTTCGGAGGAAGAAACAGATCTTATCATCAGGCTTC
RTPAP1_mrnaAA  200 eAsnArgGluLysPheSerGluGluGluThrAspLeuIleIleArgLeuH
     SNP_1AA   200 eAsnArgGluLysPheSerGluGluGluThrAspLeuIleIleArgLeuH
     SNP_2AA   200 eAsnArgGluLysPheSerGluGluGluThrAspLeuIleIleArgLeuH
     SNP_3AA   200 eAsnArgGluLysPheSerGluGluGluThrAspLeuIleIleArgLeuH
     SNP_4AA   200 eAsnArgGluLysPheSerGluGluGluThrAspLeuIleIleArgLeuH
     SNP_5AA   200 eAsnArgGluLysPheSerGluGluGluThrAspLeuIleIleArgLeuH
                   |---------|---------|---------|---------|---------
                   201       211       221       231       241

RTPAP1_mrna    250 ATAAGCTCTTGGGCAACAGGTGGTCATTAATTGCAGGTAGGCTTCCAGGC
     SNP_1     250 ATAAGCTCTTGGGCAACAGGTGGTCATTAATTGCAGGTAGGCTTCCAGGC
     SNP_2     250 ATAAGCTCTTGGGCAACAGGTGGTCATTAATTGCAGGTAGGCTTCCAGGC
     SNP_3     250 ATAAGCTCTTGGGCAACAGGTGGTCATTAATTGCAGGTAGGCTTCCAGGC
     SNP_4     250 ATAAGCTCTTGGGCAACAGGTGGTCATTAATTGCAGGTAGGCTTCCAGGC
     SNP_5     250 ATAAGCTCTTGGGCAACAGGTGGTCATTAATTGCAGGTAGGCTTCCAGGC
RTPAP1_mrnaAA  250 isLysLeuLeuGlyAsnArgTrpSerLeuIleAlaGlyArgLeuProGly
     SNP_1AA   250 isLysLeuLeuGlyAsnArgTrpSerLeuIleAlaGlyArgLeuProGly
     SNP_2AA   250 isLysLeuLeuGlyAsnArgTrpSerLeuIleAlaGlyArgLeuProGly
     SNP_3AA   250 isLysLeuLeuGlyAsnArgTrpSerLeuIleAlaGlyArgLeuProGly
     SNP_4AA   250 isLysLeuLeuGlyAsnArgTrpSerLeuIleAlaGlyArgLeuProGly
     SNP_5AA   250 isLysLeuLeuGlyAsnArgTrpSerLeuIleAlaGlyArgLeuProGly
                   |---------|---------|---------|---------|---------
                   251       261       271       281       291

RTPAP1_mrna    300 AGGACAGCAAATGACATCAAGAACTACTGGAACACTCACCTGGGCAAGAA
     SNP_1     300 AGGACAGCAAATGACATCAAGAACTACTGGAACACTCACCTGGGCAAGAA
     SNP_2     300 AGGACAGCAAATGACATCAAGAACTACTGGAACACTCACCTGGGCAAGAA
     SNP_3     300 AGGACAGCAAATGACATCAAGAACTACTGGAACACTCACCTGGGCAAGAA
     SNP_4     300 AGGACAGCAAATGACATCAAGAACTACTGGAACACTCACCTGGGCAAGAA
     SNP_5     300 AGGACAGCAAATGACATCAAGAACTACTGGAACACTCACCTGGGCAAGAA
RTPAP1_mrnaAA  300 ArgThrAlaAsnAspIleLysAsnTyrTrpAsnThrHisLeuGlyLysLy
     SNP_1AA   300 ArgThrAlaAsnAspIleLysAsnTyrTrpAsnThrHisLeuGlyLysLy
     SNP_2AA   300 ArgThrAlaAsnAspIleLysAsnTyrTrpAsnThrHisLeuGlyLysLy
     SNP_3AA   300 ArgThrAlaAsnAspIleLysAsnTyrTrpAsnThrHisLeuGlyLysLy
     SNP_4AA   300 ArgThrAlaAsnAspIleLysAsnTyrTrpAsnThrHisLeuGlyLysLy
     SNP_5AA   300 ArgThrAlaAsnAspIleLysAsnTyrTrpAsnThrHisLeuGlyLysLy
                   |---------|---------|---------|---------|---------
                   301       311       321       331       341

RTPAP1_mrna    350 AGTAGAAGTTGAAAACAAGAAGGCGGAGCCCAGTGCTGATGCCAAAGTAA
     SNP_1     350 AGTAGAAGTTGAAAACAAGAAGGCGGAGCCCAGTGCTGATGCCAAAGTAA
     SNP_2     350 AGTAGAAGTTGAAAACAAGAAGGCGGAGCCCAGTGCTGATGCCAAAGTAA
     SNP_3     350 AGTAGAAGTTGAAAACAAGAAGGCGGAGCCCAGTGCTGATGCCAAAGTAA
     SNP_4     350 AGTAGAAGTTGAAAACAAGAAGGCGGAGCCCAGTGCTGATGCCAAAGTAA
     SNP_5     350 AGTAGAAGTTGAAAACAAGAAGGCGGAGCCCAGTGCTGATGCCAAAGTAA
RTPAP1_mrnaAA  350 sValGluValGluAsnLysLysAlaGluProSerAlaAspAlaLysValI
     SNP_1AA   350 sValGluValGluAsnLysLysAlaGluProSerAlaAspAlaLysValI
     SNP_2AA   350 sValGluValGluAsnLysLysAlaGluProSerAlaAspAlaLysValI
     SNP_3AA   350 sValGluValGluAsnLysLysAlaGluProSerAlaAspAlaLysValI
     SNP_4AA   350 sValGluValGluAsnLysLysAlaGluProSerAlaAspAlaLysValI
     SNP_5AA   350 sValGluValGluAsnLysLysAlaGluProSerAlaAspAlaLysValI
                   |---------|---------|---------|---------|---------
                   351       361       371       381       391
```

*FIG. 11 (cont'd)*

```
RTPAP1_mrna    400 TTAAGCCACGGCCATGGAAAGTACCGTTGCAATGGTTATGGTCAGAAGAT
SNP_1          400 TTAAGCCACGGCCATGGAAAGTACCGTTGCAATGGTTATGGTCAGAAGAT
SNP_2          400 TTAAGCCACGGCCATGGAAAGTACCGTTGCAATGGTTATGGTCAGAAGAT
SNP_3          400 TTAAGCCACGGCCATGGAAAGTACCGTTGCAATGGTTATGGTCAGAAGAT
SNP_4          400 TTAAGCCACGGCCATGGAAAGTACCGTTGCAATGGTTATGGTCAGAAGAT
SNP_5          400 TTAAGCCACGGCCATGGAAAGTACCGTTGCAATGGTTATGGTCAGAAGAT
RTPAP1_mrnaAA  400 leLysProArgProTrpLysValProLeuGlnTrpLeuTrpSerGluAsp
SNP_1AA        400 leLysProArgProTrpLysValProLeuGlnTrpLeuTrpSerGluAsp
SNP_2AA        400 leLysProArgProTrpLysValProLeuGlnTrpLeuTrpSerGluAsp
SNP_3AA        400 leLysProArgProTrpLysValProLeuGlnTrpLeuTrpSerGluAsp
SNP_4AA        400 leLysProArgProTrpLysValProLeuGlnTrpLeuTrpSerGluAsp
SNP_5AA        400 leLysProArgProTrpLysValProLeuGlnTrpLeuTrpSerGluAsp
                   |---------|---------|---------|---------|------
                   401       411       421       431       441

RTPAP1_mrna    450 CAGCAATCATGTGGAAGCCAGCAGCCGCAAGAAAAGTTTGGGATACCAGA
SNP_1          450 CAGCAATCATGTGGAAGCCAGCAGCCGCAAGAAAAGTTTGGGATACCAGA
SNP_2          450 CAGCAATCATGTGGAAGCCAGCAGCCGCAAGAAAAGTTTGGGATACCAGA
SNP_3          450 CAGCAATCATGTGGAAGCCAGCAGCCGCAAGAAAAGTTTGGGATACCAGA
SNP_4          450 CAGCAATCATGTGGAAGCCAGCAGCCGCAAGAAAAGTTTGGGATACCAGA
SNP_5          450 CAGCAATCATGTGGAAGCCAGCAGCCGCAAGAA------------GAT---------
RTPAP1_mrnaAA  450 GlnGlnSerCysGlySerGlnGlnProGlnGluLysPheGlyIleProGl
SNP_1AA        450 GlnGlnSerCysGlySerGlnGlnProGlnGluLysPheGlyIleProGl
SNP_2AA        450 GlnGlnSerCysGlySerGlnGlnProGlnGluLysPheGlyIleProGl
SNP_3AA        450 GlnGlnSerCysGlySerGlnGlnProGlnGluLysPheGlyIleProGl
SNP_4AA        450 GlnGlnSerCysGlySerGlnGlnProGlnGluLysPheGlyIleProGl
SNP_5AA        450 GlnGlnSerCysGlySerGlnGlnProGlnGluAspTer
                   |---------|---------|---------|---------|------
                   451       461       471       481       491

RTPAP1_mrna    500 ACTACCGACAATCTCAGAGAACGATGAAGCGTGGCTGAATTGTATAATGA
SNP_1          500 ACTACCGACAATCTCAGAGAACGATGAAGCGTGGCTGAATTGTATAATGA
SNP_2          500 ACTACCGACAATCTCAGAGAACGATGAAGCGTGGCTGAATTGTATAATGA
SNP_3          500 ACTACCGACAATCTCAGAGAACGATGAAGCGTaGCTGAATTGTATAATGA
SNP_4          500 ACTACCGACAATCTCAGAGAACGATGAAGCGTGGCTGAATTGTA--ATGA
SNP_5          486 ------------------------------------------TAATG--
RTPAP1_mrnaAA  500 uLeuProThrIleSerGluAsnAspGluAlaTrpLeuAsnCysIleMetA
SNP_1AA        500 uLeuProThrIleSerGluAsnAspGluAlaTrpLeuAsnCysIleMetA
SNP_2AA        500 uLeuProThrIleSerGluAsnAspGluAlaTrpLeuAsnCysIleMetA
SNP_3AA        500 uLeuProThrIleSerGluAsnAspGluAlaTer
SNP_4AA        500 uLeuProThrIleSerGluAsnAspGluAlaTrpLeuAsnCys**Asn-Gl**
SNP_5AA        486
                   |---------|---------|---------|---------|------
                   501       511       521       531       541

RTPAP1_mrna    550 ATGGAGATAGAGAGAACAGTGCAGTGCCAGACGTTGGAAACGGGAGCACA
SNP_1          550 ATGGAGATAGAGAGAACAGTGCAGTGCCAGACGTTGGAAACGGGAGCACA
SNP_2          550 ATGGAGATAGAGAGAACAGTGCAGTGCCAGACGTTGGAAACGGGAGCACA
SNP_3          550 ATGGAGATAGAGAGAACAGTGCAGTGCCAGACGTTGGAAACGGGAGCACA
SNP_4          548 ATGGAGATAGAGAGAACAGTGCAGTGCCAGACGTTGGAAACGGGAGCACA
SNP_5          491 -------------------------------CtTTGGGC-------CACt
RTPAP1_mrnaAA  550 snGlyAspArgGluAsnSerAlaValProAspValGlyAsnGlySerThr
SNP_1AA        550 snGlyAspArgGluAsnSerAlaValProAspValGlyAsnGlySerThr
SNP_2AA        550 snGlyAspArgGluAsnSerAlaValProAspValGlyAsnGlySerThr
SNP_3AA        550
SNP_4AA        548 uTrpArgTer
SNP_5AA        491
                   |---------|---------|---------|---------|------
                   551       561       571       581       591
```

*FIG. 11 (cont'd)*

```
RTPAP1_mrna    600 ATGAACCTGCAGAATGAATTTGGAATCGGAGGCTTGGAGGAAAATAGAGA
      SNP_1    600 ATGAACCTGCAGAATGAATTTGGAATCGGAGGCTTGGAGGAAAATtGAGA
      SNP_2    600 ATGAACCTGCAGAATtAATTTGGAATCGGAGGCTTGGAGGAAAATAGAGA
      SNP_3    600 ATGAACCTGCAGAATGAATTTGGAATCGGAGGCTTGGAGGAAAATAGAGA
      SNP_4    598 ATGAACCTGCAGAATGAATTTGGAATCGGAGGCTTGGAGGAAAATAGAGA
      SNP_5    503 ATa-----------------------------------------------
RTPAP1_mrnaAA  600 MetAsnLeuGlnAsnGluPheGlyIleGlyGlyLeuGluGluAsnArgAs
     SNP_1AA   600 MetAsnLeuGlnAsnGluPheGlyIleGlyGlyLeuGluGluAsnTer
     SNP_2AA   600 MetAsnLeuGlnAsnTer
     SNP_3AA   600
     SNP_4AA   598
     SNP_5AA   503

|---------|---------|---------|---------|---------
                   601       611       621       631       641

RTPAP1_mrna    650 TGGGGCAGTGTTTCTGGAAGGAGTTCTAGGATGGGATGACTTGCTTTGGG
      SNP_1    650 TGGGGCAGTGTTTCTGGAAGGAGTTCTAGGATGGGATGACTTGCTTTGGG
      SNP_2    650 TGGGGCAGTGTTTCTGGAAGGAGTTCTAGGATGGGATGACTTGCTTTGGG
      SNP_3    650 TGGGGCAGTGTTTCTGGAAGGAGTTCTAGGATGGGATGACTTGCTTTGGG
      SNP_4    648 TGGGGCAGTGTTTCTGGAAGGAGTTCTAGGATGGGATGACTTGCTTTGGG
      SNP_5    506 --------tAGTGcTTaTatA-------------TGGGATGACTTGCTTTGGG
RTPAP1_mrnaAA  650 pGlyAlaValPheLeuGluGlyValLeuGlyTrpAspAspLeuLeuTrpA
     SNP_1AA   650
     SNP_2AA   650
     SNP_3AA   650
     SNP_4AA   648
     SNP_5AA   506

|---------|---------|---------|---------|---------
                   651       661       671       681       691

RTPAP1_mrna    700 CCACTATATAGTGCTCATATATGGTAGTGCAATAGTTGCCATTATAAGTT
      SNP_1    700 CCACTATATAGTGCTCATATATGGTAGTGCAATAGTTGCCATTATAAGTT
      SNP_2    700 CCACTATATAGTGCTCATATATGGTAGTGCAATAGTTGCCATTATAAGTT
      SNP_3    700 CCACTATATAGTGCTCATATATGGTAGTGCAATAGTTGCCATTATAAGTT
      SNP_4    698 CCACTATATAGTGCTCATATATGGTAGTGCAATAGTTGCCATTATAAGTT
      SNP_5    538 CCACTATATAGTGCTtATATATGGTAGTGCAATAGTTGCCATTATAAGTT
RTPAP1_mrnaAA  700 laThrIleTer
     SNP_1AA   700
     SNP_2AA   700
     SNP_3AA   700
     SNP_4AA   698
     SNP_5AA   538

|---------|---------|---------|---------|---------
                   701       711       721       731       741

RTPAP1_mrna    750 GTTTCGAACTTTAATGCTCCTGAAATTCCCATGCAAGTATTTAGAGCTTC
      SNP_1    750 GTTTCGAACTTTAATGCTCCTGAAATTCCCATGCAAGTATTTAGAGCTTC
      SNP_2    750 GTTTCGAACTTTAATGCTCCTGAAATTCCCATGCAAGTATTTAGAGCTTC
      SNP_3    750 GTTTCGAACTTTAATGCTCCTGAAATTCCCATGCAAGTATTTAGAGCTTC
      SNP_4    748 GTTTCGAACTTTAATGCTCCTGAAATTCCCATGCAAGTATTTAGAGCTTC
      SNP_5    588 GTTTCGAACTTTAATGCTCCTGAAATTCCCATGCAAGTATTTAGAGCTTC
RTPAP1_mrnaAA  750
     SNP_1AA   750
     SNP_2AA   750
     SNP_3AA   750
     SNP_4AA   748
     SNP_5AA   588

|---------|---------|---------|---------|---------
                   751       761       771       781       791
```

*FIG. 11 (cont'd)*

```
RTPAP1_mrna    800 ATATCCTACAAAAAGACAGGAAACGAGACCTTGAAAAAAGACTCAGTACC
      SNP_1    800 ATATCCTACAAAAAGACAGGAAACGAGACCTTGAAAAAAGACTCAGTACC
      SNP_2    800 ATATCCTACAAAAAGACAGGAAACGAGACCTTGAAAAAAGACTCAGTACC
      SNP_3    800 ATATCCTACAAAAAGACAGGAAACGAGACCTTGAAAAAAGACTCAGTACC
      SNP_4    798 ATATCCTACAAAAAGACAGGAAACGAGACCTTGAAAAAAGACTCAGTACC
      SNP_5    638 ATATCCTACAAAAAGACAGGAAACGAGACCTTGAAAAAAGACTCAGTACC
RTPAP1_mrnaAA  800
    SNP_1AA    800
    SNP_2AA    800
    SNP_3AA    800
    SNP_4AA    798
    SNP_5AA    638
                   |---------|---------|---------|---------|---------
                  801       811       821       831       841

RTPAP1_mrna    850 AGAAGGCATCCACTTATTGATTGCTTTTATACTTGCAACATGAAGGAAGC
      SNP_1    850 AGAAGGCATCCACTTATTGATTGCTTTTATACTTGCAACATGAAGGAAGC
      SNP_2    850 AGAAGGCATCCACTTATTGATTGCTTTTATACTTGCAACATGAAGGAAGC
      SNP_3    850 AGAAGGCATCCACTTATTGATTGCTTTTATACTTGCAACATGAAGGAAGC
      SNP_4    848 AGAAGGCATCCACTTATTGATTGCTTTTATACTTGCAACATGAAGGAAGC
      SNP_5    688 AGAAGGCATCCACTTATTGATTGCTTTTATACTTGCAACATGAAGGAAGC
RTPAP1_mrnaAA  850
    SNP_1AA    850
    SNP_2AA    850
    SNP_3AA    850
    SNP_4AA    848
    SNP_5AA    688
                   |---------|---------|---------|---------|---------
                  851       861       871       881       891

RTPAP1_mrna    900 ACGCTTTCTCACCAAAAAAAAAA
      SNP_1    900 ACGCTTTCTCACCAAAAAAAAAA
      SNP_2    900 ACGCTTTCTCACCAAAAAAAAAA
      SNP_3    900 ACGCTTTCTCACCAAAAAAAAAA
      SNP_4    898 ACGCTTTCTCACCAAAAAAAAAA
      SNP_5    738 ACGCTTTCTCACCAAAAAAAAAA
RTPAP1_mrnaAA  900
    SNP_1AA    900
    SNP_2AA    900
    SNP_3AA    900
    SNP_4AA    898
    SNP_5AA    738
                   |---------|---------|---------
                  901       911       921
```

*FIG. 11 (cont'd)* a.
5' AACTACCGACAATCTCTCAGAGAACGATGAAGCCGTgGCTGAATTGTATAATGAATGGAGATAGAGAGAACAG 3'
3' ←FAMC 5' b.
5' AACTACCGACAATCTCTCAGAGAACGATGAAGCCGTaGCTGAATTGTATAATGAATGGAGATAGAGAGAACAG 3'
3' ←TAMT 5'

*FIG. 15*

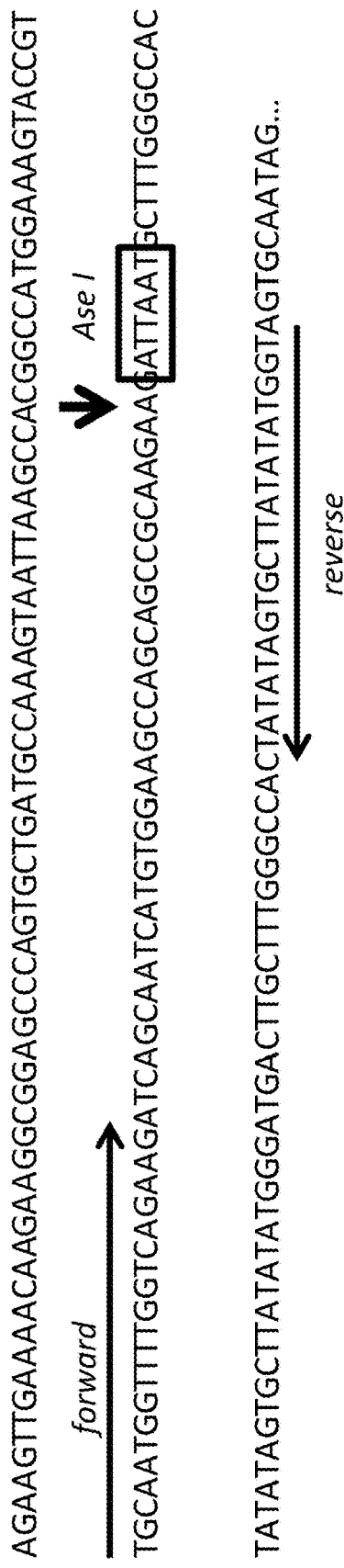
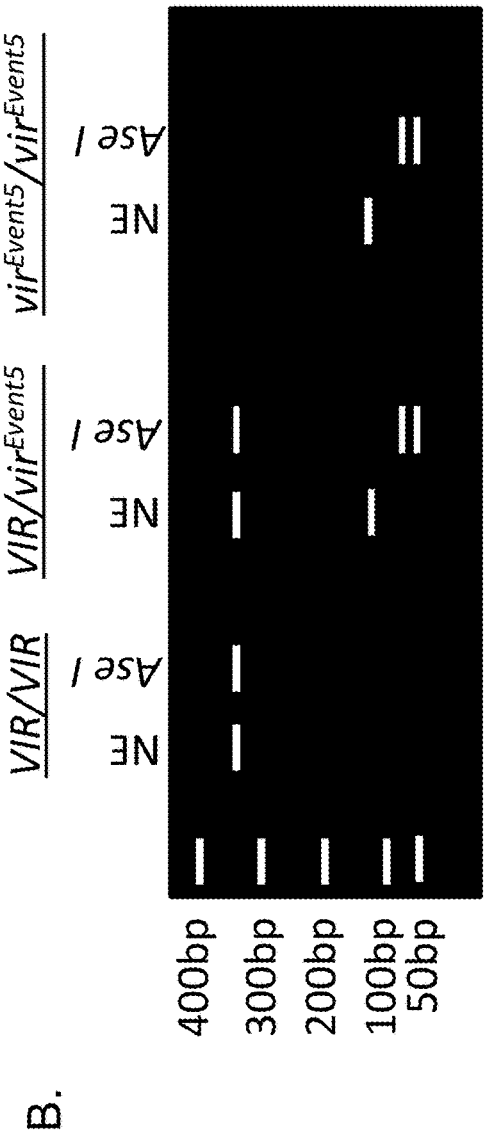
FIG. 16

GENE CONTROLLING FRUIT COLOR PHENOTYPE IN PALM

CROSS-REFERENCE TO RELATED APPLICATIONS

The present patent application claims benefit of priority to U.S. Provisional Patent Application No. 61/809,767, filed on Apr. 8, 2013, which is incorporated by reference.

BACKGROUND OF THE INVENTION

The oil palm (*Elaeis guineensis* Jacq.) is the main source of vegetable oil in the world and is currently one of the most important crops planted in South East Asia, Africa and South America. The demand for palm oil is high and it has risen steadily for the past decade. As such it is desirable to identify traits that can be exploited to improve palm oil yield. However, the long selection cycle (10-12 years) for oil palm makes traditional breeding programs inefficient at providing improved planting material within a reasonable time frame.

One important trait related to palm oil production is the skin colour of the fruit. The skin color of the fruit of the oil palm can vary considerably based on external appearance, (FIG. 1). By far the most common type of fruit is deep violet to black at the apex and whitish-yellow at the base when unripe. Such a fruit has been described as *nigrescens* (Hartley, C. In: *The Oil Palm*. 47-94 (Longman, 1988)). The color of the *nigrescens* fruit varies to some extent on ripening, to either entirely red, or black over the upper half but red at the base (Hartley, C. In: *The Oil Palm*. 47-94 (Longman, 1988)). Harvesters of *nigrescens* oil palm fruit have to rely solely on the presence of loose fruits on the ground, detached from the oil palm bunch, to determine that the bunch containing the fruits is ready for harvest. The collection of loose fruits is labor intensive and can occupy up to 28% of the total harvesting time (Hitam, A. et al. In: *Proceedings of the 1999 PORIM International Palm Oil Congress (PIPOC)*— Emerging technologies and opportunities in the next millennium, ed. A. Darus, C. K. Weng, and S. S. R. S. Alwee, pp 325-336, Palm Oil Research Institute of Malaysia (PORIM), Bangi, Malaysia.). Indeed, difficulty with loose fruit collection is considered a significant contributor to the decline of oil extraction rates (OER) observed in Malaysian Plantations (Corley and Law, Planter, 77: 507-524 (2001)).

The other major fruit type is known as *virescens*, which is green before ripening and changes at maturity to light-reddish-orange in colour. Inheritance studies indicate that the *virescens* trait is controlled by a single gene (monogenic) and dominant (Corley and Tinker. In: *The Oil Palm* 4$^{th}$ edn, 287-325 (Blackwell Science, 2003))). Generally, fresh fruit bunch (FFB) yields of more than 30 tons/ha, with oil/bunch ranging from 29-30%, have been reported in progeny testing involving *virescens* palms (Wahid and Rajanaidu. Oil Palm Breeding and Competitive approaches. Agriculture Biotechnology International Conference (ABIC), 12-15 September, 2004. Cologne, Germany.) and the yield profile is similar to *nigrescens* palms.

Both the *nigrescens* and *virescens* fruits occur in wild-type oil palm populations. However, although the *virescens* trait is dominant, the number of *virescens* palms found in natural populations is small, perhaps suggesting that they have been selected against by farmers or could have associated negative traits. In Nigeria for example only 50 of 10,000 bunches observed were *virescens*, while in Angola only 72 of 10,000 bunches observed were *virescens*, (Hartley, C. In: *The Oil Palm*. 47-94 (Longman, 1988)). However, as reported by Corley and Tinker (Corley and Tinker. In: *The Oil Palm* 4$^{th}$ edn, 287-325 (Blackwell Science, 200)3)), Rajanaidu found 6% *virescens* palms among his collections in Cameroon (Rajanaidu, N. In: ni Proc. Int. Workshop. "Oil palm germplasm and utilization". Palm Oil Res. Inst. Malaysia. 59-83 (1986)). Currently, commercial plantations primarily utilize *nigrescens* palms. However, *virescens*, palms can be more desirable to planters as the clear difference in colour between ripe and unripe bunches make it easier to identify ripe bunches, particularly in tall palms, where bunches can be obscured by fronds.

Traditional methods do not allow identification of the fruit type of a given plant until it has matured enough to produce a first batch of fruit, which typically takes approximately six years after germination. In plantations desirous of introducing *virescens* materials, significant land, labor, financial and energy resources are invested during the interval from germination to fruit production, some of which will ultimately be of the *nigrescens* fruit types. By the time *nigrescens* palms are identified, it is impractical to remove them from the field and replace them with *virescens* palms, and thus growers will have a mixture of both types of palm plants, which may affect yields for the 25 to 30 year production life of the plants due to inefficient identification of ripe *nigrescens* bunches. Similarly, the long selection cycle of 10-12 years from seed to seed makes it laborious to use traditional breeding methods to identify or develop true breeding strains of *virescens* palm oil.

BRIEF SUMMARY OF THE INVENTION

In some embodiments, the present invention provides method for determining a fruit color phenotype of a palm plant, the method comprising, providing a sample from a plant or seed; and detecting presence or absence of a VIR gene alteration in a genomic region corresponding to SEQ ID NO:1 that confers a *virescens* phenotype to fruit, or detecting a presence or absence of a genetic marker linked to the alteration within 2,000 kb of the genomic region, wherein the presence of the alteration or genetic marker predicts the presence of the *virescens* phenotype. In some cases, detection of the absence of the alteration or genetic marker predicts the presence of the *nigrescens* phenotype.

In some aspects the alteration comprises a nucleotide change that results in an encoded amino acid change, a splice site or other alteration resulting in a change in splicing, and/or a stop codon.

In some aspects the method comprises detecting the presence or absence of a VIR gene alteration in a genomic region corresponding to SEQ ID NO:1 that confers a *virescens* phenotype to fruit.

In some cases, the alteration comprises a premature stop codon so as to generate a truncated protein compared to SEQ ID) NO:4.

In some cases, alteration is a dominant negative mutation.

In some cases, the alteration is selected from the group corresponding to SEQ ID NOS:7, 9, 11, 13, or 15, or the alteration produces a VIR allele that encodes an amino acid sequence selected from the group consisting of SEQ ID NOS:5, 8, 10, 12, and 14.

In some aspects, the VIR gene encodes (i) a polypeptide substantially (e.g., at least 70, 75, 80, 85, 90, or 95%) identical or identical to SEQ ID NO:4 or (ii) a polypeptide comprising at least 100, 125, 150, 175, 200, or 225 contiguous amino acids that are substantially (e.g., at least 70, 75, 80, 85, 90, or 95%) identical or identical to to a corresponding fragment of the SEQ ID NO:4. For example, the polypeptide or polypeptide fragment could contain 0, 1, 2, 3, or 4 amino acid substitutions or deletions in comparison to SEQ ID NO:4.

In some aspects the method comprises detecting a presence or absence of a genetic marker linked to the alteration within 1, 10, 20, 50, 100, 200, 500, 1000 kb, or 2000 kb from the genomic region.

In some aspects, the plant is less than 5 years old, or less than one year old. In some aspects, the plant is an oil palm.

In some aspects, the method comprises selecting the plant or seed for cultivation if the plant is predicted to have the *virescens* phenotype.

In some aspects, the method comprises selecting the plant or seed for cultivation if the plant is predicted to have the *nigrescens* phenotype.

In some cases, the plant or seed is discarded if the plant or seed is not predicted to have the *virescens* phenotype.

In some cases, the plant or seed is discarded if the plant or seed is predicted to have the *virescens* phenotype.

In some cases, the method further comprises predicting a shell thickness phenotype by detecting the presence or absence of a nucleic acid sequence associated with a dura, *tenera*, or *pisifera* phenotype. In some cases, the shell thickness phenotype is predicted from the same sample as the fruit color phenotype. In some cases, the shell thickness phenotype is predicted by detecting the presence or absence of a polymorphism at or near the SHELL locus, or at or near the locus of a gene encoding a MADS box containing protein associated with a dura, *tenera*, or *pisifera* phenotype.

In some embodiments, the present invention provides a method for segregating a plurality of palm plants into different categories based on predicted fruit color phenotype, the method comprising, providing a sample from each plant in the plurality of plants; detecting a presence or absence of a VIR gene alteration in a genomic region corresponding to SEQ ID NO:1 that confers a *virescens* phenotype to fruit, or detecting a presence or absence of a genetic marker linked to the alteration within 2000 kb of the genomic region, wherein the presence of the alteration or genetic marker predicts the presence of the *virescens* phenotype; and segregating the plants into groups based on the predicted *virescens* phenotype of the plants. For example, plants can be segregated into one group predicted to have a *virescens* phenotype and segregated into a different group predicted to have a *nigrescens* phenotype.

In some aspects, the method comprises detecting the presence or absence of a VIR gene alteration in a genomic region corresponding to SEQ ID NO:1 that confers a *virescens* phenotype to fruit.

In some cases, the alteration comprises a premature stop codon so as to generate a truncated protein compared to SEQ ID NO:4.

In some cases, the alteration is a dominant negative mutation.

In some cases, the alteration produces a VIR allele that encodes an amino acid sequence selected from the group consisting of SEQ ID NOS:5, 8, 10, 12, and 14.

In some cases, VIR gene encodes (i) a polypeptide substantially (e.g., at least 70, 75, 80, 85, 90, or 95%) identical or identical to SEQ ID NO:4 or (ii) a polypeptide comprising at least 100, 125, 150, 175, 200, or 225 contiguous amino acids that are substantially (e.g., at least 70, 75, 80, 85, 90, or 95%) identical or identical to a corresponding fragment of SEQ ID NO:4. For example, the polypeptide or polypeptide fragment could contain 0, 1, 2, 3, or 4 amino acid substitutions or deletions in comparison to SEQ ID NO:4.

In some aspects, the method comprises detecting a presence or absence of a genetic marker linked to the alteration within 1, 10, 20, 50, 100, 200, 500, 1000, or 2000 kb from the genomic region.

In some aspects, the plant is less than 5 years old, or the plant is less than one year old.

In some aspects, the plant is an oil palm.

In some cases, the method further comprises predicting a shell thickness phenotype by detecting the presence or absence of a nucleic acid sequence associated with a dura, *tenera*, or *pisifera* phenotype. In some cases, the shell thickness phenotype is predicted from the same sample as the fruit color phenotype. In some cases, the shell thickness phenotype is predicted by detecting the presence or absence of a polymorphism at or near the SHELL locus, or at or near the locus of a gene encoding a MADS box containing protein associated with a dura, *tenera*, or *pisifera* phenotype.

In some embodiments, the present invention provides a method for determining a fruit color phenotype of a palm plant, the method comprising, providing a sample from a plant or seed; and detecting presence or absence of an alteration in a VIR polypeptide corresponding to SEQ ID NO:4 that confers a *virescens* phenotype to fruit, wherein the presence of the alteration predicts the presence of the *virescens* phenotype. In some cases, detection of the absence of the alteration predicts the presence of the *nigrescens* phenotype.

In some embodiments, the present invention provides a kit for determining the fruit color phenotype (e.g., *virescens* or *nigrescens*) of a palm plant, the kit comprising, one or more oligonucleotide primers or probes comprising: a sequence of at least 6 (or 8, 10, 12, 14, 16, 18, 20, 22, 24, or more) nucleotides of SEQ ID NO:17; and/or; a sequence 100% complementary to at least 6 (or 8, 10, 12, 14, 16, 18, 20, 22, 24, or more) nucleotides of SEQ ID NO:17.

In some aspects, the primer or probe specifically hybridizes to palm plant DNA and/or to SEQ ID NO:17.

In some aspects, the kit comprises one or more oligonucleotide primers or probes comprising: a sequence of at least 6 (or 8, 10, 12, 14, 16, 18, 20, 22, 24, or more) nucleotides of SEQ ID NO:1; and/or; a sequence 100% complementary to at least 6 (or 8, 10, 12, 14, 16, 18, 20, 22, 24, or more) nucleotides of SEQ ID NO:1.

In some aspects, the primer or probe specifically hybridizes to SEQ ID NO:1.

In some aspects, the primer or probe specifically hybridizes to an alteration in SEQ ID NO:1 indicating a *virescens* allele.

In some cases, the alteration is selected from the group corresponding to SEQ ID NOS:7, 9, 11, or 13, or the alteration produces a VIR allele that encodes an amino acid sequence selected from the group consisting of SEQ ID NOS:5, 8, 10, 12, and 14.

In some aspects, a detectable label is linked to the oligonucleotide.

In some cases, the detectable label is fluorescent.

In some aspects, the kit further comprises a polynucleotide comprising a sequence substantially (e.g., at least 70, 75, 80, 85, 90, 95, 97, 98, 99%) identical or identical to at least 100, 200, 300, 400, 500, 750, 1000 or more contiguous nucleotides of SEQ ID NO:17 or SEQ ID NO:1.

In some aspects, the kit further comprises palm genomic DINA.

In some cases, the kit further comprises one or more oligonucleotide primers or probes for predicting a shell thickness phenotype. In some cases, the kit further comprises one or more immunological binding reagents (e.g., peptides or peptide fragments) for predicting a shell thickness phenotype.

In some embodiments, the present invention provides isolated nucleic acid comprising a polynucleotide encoding a polypeptide comprising a sequence substantially (e.g., at least 70, 75, 80, 85, 90, 95, 97, 98, 99%) identical or identical to SEQ ID NO:4 or a polypeptide fragment comprising at least 100, 125, 150, 175, 200, or 225 contiguous amino acids that are substantially (e.g., at least 70, 75, 80, 85, 90, or 95%) identical or identical to a corresponding fragment of SEQ ID NO:4. For example, the polypeptide or polypeptide fragment could contain 0, 1, 2, 3, or 4 amino acid substitutions or deletions in comparison to SEQ ID NO:4.

In some embodiments, the present invention provides a plant comprising a heterologous expression cassette, the expression cassette comprising a heterologous promoter operably linked to a polynucleotide encoding (i) a polypeptide comprising a sequence substantially (e.g., at least 70, 75, 80, 85, 90, 95, 97, 98, 99%) identical or identical to SEQ ID NO:4 or (ii) a polypeptide comprising at least 100, 125, 150, 175, 200, or 225 contiguous amino acids that are substantially (e.g., at least 70, 75, 80, 85, 90, or 95%) identical to a corresponding fragment of SEQ ID NO:4.

For example, the polypeptide could contain 0, 1, 2, 3, or 4 amino acid substitutions or deletions in comparison to SEQ ID NO:4 or in comparison to at least 100, 125, 150, 175, 200, or 225 contiguous amino acids of SEQ ID NO:4.

In some aspects, the plant is a palm plant, or the plant is an oil palm plant.

In some aspects, the polypeptide comprises SEQ ID NO:4.

In some aspects, the plant is a *virescens* oil palm plant.

In some aspects, the plant is a *nigrescens* oil palm plant.

In some embodiments, the present invention provides an isolated nucleic acid comprising an expression cassette, the expression cassette comprising a heterologous promoter operably linked to a polynucleotide encoding a polypeptide comprising (i) a sequence substantially (e.g., at least 70, 75, 80, 85, 90, 95, 97, 98, 99%) identical or identical to SEQ ID NO:4 or (ii) a polypeptide comprising at least 100, 125, 150, 175, 200, or 225 contiguous amino acids that are substantially (e.g., at least 70, 75, 80, 85, 90, or 95%) identical or identical to a corresponding fragment of SEQ ID NO:4. For example, the polypeptide could contain 0, 1, 2, 3, or 4 amino acid substitutions or deletions in comparison to SEQ ID NO:4 or in comparison to at least 100, 125, 150, 175, 200, or 225 contiguous amino acids of SEQ ID NO:4.

In some embodiments, the present invention provides an isolated nucleic acid comprising an expression cassette comprising a promoter operably linked to a polynucleotide, which polynucleotide, when expressed in the plant, reduces expression of a VIR polypeptide in a plant (compared to a control plant lacking the expression cassette).

In some aspects, the polynucleotide comprises at least 20 contiguous nucleotides, or the complement thereof, of a nucleic acid encoding a VIR polypeptide (e.g., an endogenous nucleic acid) substantially (e.g., at least 70, 75, 80, 85, 90, 95, 97, 98, 99%) identical or identical to SEQ ID NO:4, such that expression of the polynucleotide in a plant inhibits expression of the endogenous VIR gene. In some aspects the polynucleotide has 0, 1, 2, 3, 4, 5 substitutions or deletions relative to at least 20 contiguous nucleotides of a nucleic acid (e.g., an endogenous nucleic acid) encoding SEQ ID NO:4, such that expression of the polynucleotide in a plant inhibits expression of the endogenous VIR gene.

In some aspects, the polynucleotide comprises at least 20, 30, 40, 50, 75, or 100 contiguous nucleotides, or the complement thereof, of SEQ ID NO:1 or SEQ ID NO:3.

In some cases, the polynucleotide encodes an siRNA, antisense polynucleotide, a microRNA, or a sense suppression nucleic acid, which when expressed in a plant suppresses expression of an endogenous VIR gene.

In some embodiments, the present invention provides a plant having a *virescens* phenotype, the plant comprising an expression cassette as described herein.

In some cases, the plant is a palm (e.g., oil palm) plant.

In some embodiments, the present invention provides an isolated nucleic acid comprising an expression cassette comprising a promoter operably linked to a polynucleotide encoding a polypeptide comprising an amino acid sequence substantially (e.g., at least 70, 75, 80, 85, 90, 95, 97, 98, 99%) identical or identical to at least 100, 125, 150, 175, 200, or 225 contiguous amino acids of SEQ ID NO:4 but lacking at least a corresponding 3' terminal portion (e.g., at least 10, 20, 30, 40, 50, 60, 70, 80, 90, 100, 110, 120, 130, 140, 150 carboxyl terminal amino acids) of SEQ ID NO:4.

In some aspects, the polypeptide comprises the polypeptide encoded by SEQ ID NOS:7, 9, 11, 13, or 15.

In some embodiments, the present invention provides a plant having a *virescens* phenotype, the plant comprising an expression cassette as described herein.

In some aspects, the plant is a palm (e.g., oil palm) plant.

In some embodiments, the present invention provides a method of making a plant as described herein, the method comprising introducing an expression cassette of the invention into a plant.

In some embodiments, the present invention provides a method of cultivating a plant of as described herein.

Other embodiments will be evident from reading the rest of the disclosure.

DEFINITIONS

A "polymorphic marker" refers to a genetic marker that distinguishes between at least two different alleles. Exemplary polymorphic markers include, but are not limited to, single nucleotide polymorphisms (SNPs), variable number of tandem repeat polymorphisms (VNTR), restriction fragment length polymorphisms, (RFLP), microsatellite markers, insertions or deletions in a DNA sequence (Indels) or simple sequence repeats of DNA sequence (SSRs).

A genomic region "corresponding to" a test sequence refers to a genomic DNA that aligns with the test sequence. It is generally expected that a plant genome will have only one genomic region (i.e., a locus represented by two alleles in a diploid plant) corresponding to the test sequence. To the extent more than one genomic region from a plant can be aligned to the test sequence, the "corresponding" genomic region is the genomic region with the highest percent of identical nucleotides. Sequence comparisons can be performed using any BLAST™ including BLAST™ 2.2 algorithm with default parameters, described in Altschul et al., *Nuc. Acids Res.* 25:3389-3402 (1977) and Altschul et al., *J. Mol. Biol.* 215:403-410 (1990), respectively.

As used herein, the terms "nucleic acid," "polynucleotide" and "oligonucleotide" refer to nucleic acid regions, nucleic acid segments, primers, probes, amplicons and oligomer fragments. The terms are not limited by length and are generic to linear polymers of polydeoxyribonucleotides (containing 2-deoxy-D-ribose), polyribonucleotides (containing D-ribose), and any other N-glycoside of a purine or pyrimidine base, or modified purine or pyrimidine bases.

These terms include double- and single-stranded DNA, as well as double- and single-stranded RNA.

A nucleic acid, polynucleotide or oligonucleotide can comprise, for example, phosphodiester linkages or modified linkages including, but not limited to phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone linkages, and combinations of such linkages.

A nucleic acid, polynucleotide or oligonucleotide can comprise the five biologically occurring bases (adenine, guanine, thymine, cytosine and uracil) and/or bases other than the five biologically occurring bases.

Optimal alignment of sequences for comparison may be conducted by the local homology algorithm of Smith and Waterman *Add. Apl. Math.* 2.482 (1981), by the homology alignment algorithm of Needleman and Wunsch *J. Mol. Biol.* 48:443 (1970), by the search for similarity method of Pearson and Lipman *Proc. Natl. Acad. Sci.* (*U.S.A.*) 85: 2444 (1988), by computerized implementations of these algorithms (GAP, BESTFIT, BLAST™, FASTA, and TFASTA in the Wisconsin Genetics Software Package, Genetics Computer Group (GCG), 575 Science Dr., Madison, Wis.), or by inspection.

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polypeptide sequences means that a polypeptide comprises a sequence that has at least 75% sequence identity. Alternatively, percent identity can be any integer from 75% to 100%. Exemplary embodiments include at least: 75%, 80%, 85%, 90%, 95%, or 99% compared to a reference sequence using the programs described herein; preferably BLAST™ using standard parameters, as described below. One of skill will recognize that these values can be appropriately adjusted to determine identity of proteins encoded by two nucleotide sequences by taking into account codon degeneracy, amino acid similarity, reading frame positioning and the like. Polypeptides which are "substantially similar" share sequences as noted above except that residue positions which are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, aspartic acid-glutamic acid, and asparagine-glutamine.

Another indication that nucleotide sequences are substantially identical is if two molecules hybridize to each other, or a third nucleic acid, under stringent conditions. Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is about 0.02 molar at pH 7 and the temperature is at least about 60° C.

A polypeptide region "corresponding to" a test sequence refers to an amino acid sequence that aligns with the test sequence. It is generally expected that a plant proteome will have only one polypeptide region (i.e., encoded by a locus represented by two alleles in a diploid plant) corresponding to the test sequence. To the extent more than one polypeptide region from a plant can be aligned to the test sequence, the "corresponding" polypeptide region is the polypeptide region with the highest percent of identical amino acids. Sequence comparisons can be performed using any BLAST™ including BLAST™ 2.2 algorithm with suitable parameters.

The term "promoter" or "regulatory element" refers to a region or sequence determinants located upstream or downstream from the start of transcription and which are involved in recognition and binding of RNA polymerase and other proteins to initiate transcription. Promoters need not be of plant origin, for example, promoters derived from plant viruses, such as the CaMV35S promoter, can be used.

The term "plant" includes whole plants, shoot vegetative organs/structures (e.g. leaves, stems and tubers), roots, flowers and floral organs/structures (e.g. bracts, sepals, petals, stamens, carpels, anthers and ovules), seed (including embryo, endosperm, and seed coat) and fruit (the mature ovary), plant tissue (e.g. vascular tissue, ground tissue, and the like) and cells (e.g. guard cells, egg cells, trichomes and the like), and progeny of same. The class of plants that can be used in the method of the invention is generally as broad as the class of higher and lower plants amenable to transformation techniques, including angiosperms (monocotyledonous and dicotyledonous plants), gymnosperms, ferns, and multicellular algae. It includes plants of a variety of ploidy levels, including aneuploid, polyploid, diploid, haploid and hemizygous.

An "expression cassette" refers to a nucleic acid construct, which when introduced into a host cell, results in transcription and/or translation of a RNA or polypeptide, respectively. Antisense constructs or sense constructs that are not or cannot be translated are expressly included by this definition.

The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

A polynucleotide sequence is "heterologous to" an organism or a second polynucleotide sequence if it originates from a foreign species, or, if from the same species, is modified from its original form. For example, a heterologous promoter operably linked to a coding sequence refers to a promoter from a species different from that from which the coding sequence was derived, or, if from the same species, a promoter which is different from any naturally occurring allelic variants.

BRIEF DESCRIPTION OF THE DRAWINGS

FIG. 5: VIR gene sequences. a, Full cDNA sequence of wild-type (*nigrescens*) VIR (SEQ ID NO:20). The sequence of exon 3, in which VIR mutation Events 1 through 5 occur, is bolded and underlined. b, Exon 3 sequence including the Event 1 mutation (SEQ ID NO:21). The A-to-T nonsense mutation (lower case, bold) introduces the boxed stop codon. c, Exon 3 sequence including the Event 2 mutation (SEQ ID NO:22). The G-to-T nonsense mutation (lower case, bold) introduces the boxed stop codon. d, Exon 3 sequence including the Event 3 mutation (SEQ ID NO:23). The G-to-A nonsense mutation (lower case, bold) introduces the boxed stop codon. e, Exon 3 sequence including the Event 4 mutation (SEQ ID NO:24). The two-bp deletion (dashes) introduces the downstream boxed top codon. f, Exon 3 sequence including the Event 5 rearrangement (SEQ ID NO:25). The rearrangement introduces the boxed premature stop codon.

FIG. 9: Alignment of R2R3 MYB domains of various related MYB genes from several species (SEQ ID NOS:32-61). R2 and R3 domains of closely related MYB proteins were used to construct the phylogenetic tree shown in FIG. 8. The bar graph represents level of conservation. Abbreviations are as described in the legend of FIG. 8.

FIG. 11: Sequence alignment of wild-type and mutant VIR alleles (nucleotide sequences=SEQ ID NOS:62-67; amino acid sequences=SEQ ID NOS:4, 5, 8, 10, 12 and 14, respectively).

FIG. 15: Single nucleotide primer extension-based assay for genotyping the vir$^{Event3}$ allele, a, Depicts an exemplary primer (SEQ ID NO:80) and primer extension product (SEQ ID NO:81) for detecting the wild-type VIR allele (template=SEQ ID NO:79). The primer extension product contains a 3' cytosine nucleotide linked to a detectable fluorescein derivative, denoted as $^{FAM}$C. b, Depicts an exemplary primer (SEQ ID NO:80) and primer extension product (SEQ ID NO:83) for detecting the vir$^{Event3}$ allele (template=SEQ ID NO:82). The primer extension product contains a 3' thymine nucleotide linked to a detectable rhodamine derivative, denoted as $^{TAM}$T (TAMRA). Thus plants containing a VIR/VIR, VIR/vir$^{Event3}$, or vir$^{Event3}$/vir$^{Event3}$ genotype can be differentially detected.

FIG. 16: Restriction enzyme-based assay for genotyping the vir$^{Event5}$ allele. a, Depicts the AseI cleavage site present in the vir$^{Event5}$ allele (SEQ ID NO:84) and binding sites for forward (SEQ ID NO:85) and reverse (SEQ ID NO:86) amplification primers. b, Depicts the results from amplifying the region flanked by the forward and reverse primers denoted in a to produce an amplicon, digesting a portion of the amplicon with AseI, and separating both the digested portion and an undigested portion by gel electrophoresis to differentially detect plants containing a VIR/VIR$^{Event5}$, VIR/vir$^{Event5}$, or vir$^{Event5}$/vir$^{Event5}$ genotype.

DETAILED DESCRIPTION OF THE INVENTION

I. Introduction

Figure 1:
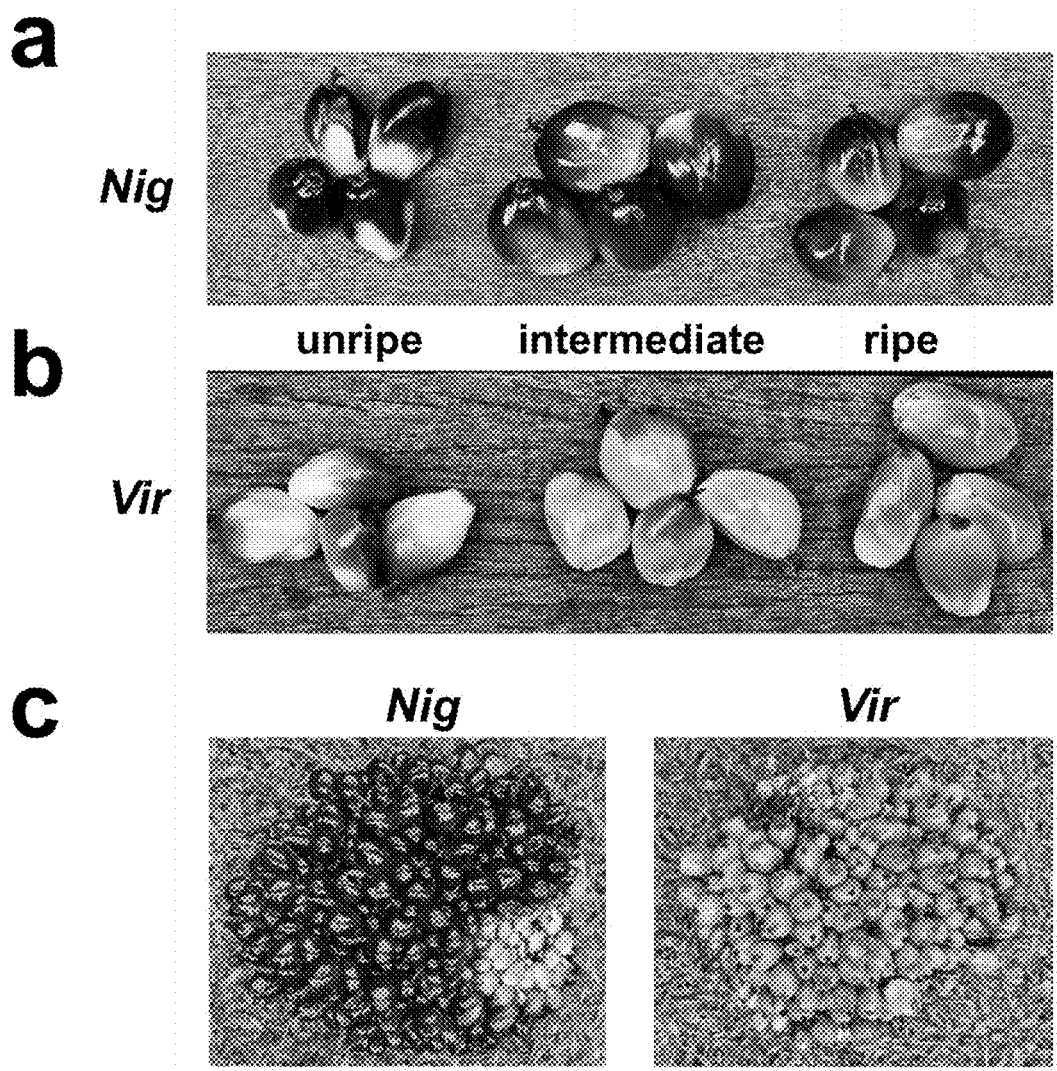
FIG. 1: Fruit exocarp colour phenotypes. a, Individual oil palm fruits from a *nigrescens* (Nig) fruit bunch. Unripe fruits are deep violet to black at the apex (visible in the bunch) and undergo minimal colour change upon ripening. b, Individual oil palm fruits from a *virescens* (Vir) fruit bunch. Unripe fruits are green at the apex and change to reddish orange upon ripening. c, ripe *nigrescens* and *virescens* fruit bunches.

The inventors have discovered the VIR gene, which is responsible for fruit color type and predicted to be a R2R3-Myb transcription factor. Truncations providing the *virescens* trait primarily deleted protein interaction domains and other regulatory domains, while leaving the DNA binding domain functionally intact. Thus, the truncated VIR genes can bind to, and sequester, transcription factor binding elements in the genome from wild-type VIR. These findings provide a genetic explanation for the monofactorial and dominant characteristics of the fruit color phenotype, and they have implications in oil palm breeding and commercial seed production.

The present disclosure describes the construction of a dense genetic map for a selfed palm, designated 1128 (0.151/128×0.151/128), from Malaysian Palm Oil Board's (MPOB) Nigerian germplasm collection (Rajanaidu, N. In: Proceedings of the 12th Plenary Meeting of Association for the Taxonomic Study of the flora of tropical Africa (AET-FAT), Mitteilingen Inst. Alig. Bet. Hamburg, Germany, pp 39-52 (1990); Chan, S. et al. In: Proceedings of the 1999 PORIM International Palm Oil Conference (eds Darus. K., Chan, K. W and Sharifah, S. R. S. A) Palm Oil Research Institute of Malaysia, pp 297-320 (1999)). A mapping population consisting of 240 palms was used for generating the genetic linkage map in this study. Six independent populations were also used to confirm the linkage of markers to the fruit color locus.

A polymorphic marker closely linked to the VIR gene, or the identification of the VIR gene itself and the use of a polymorphic marker located within the gene itself, is of significant use, as it can be used by seed producers as a quality control tool to i) reduce or eliminate *nigrescens* contamination of *virescens* seed or plantlets, and ii) positively identify *virescens* seeds or plantlets which are then selected as suitable planting material for commercial palm oil production. The identification of the VIR gene or a marker genetically linked to *virescens* trait is also of use in breeding programmes. The marker or the alleles of the gene responsible for the trait can be used to separate the *virescens*, and *nigrescens* plants in the nursery (e.g., at the seed or seedling stage); the advantage here being that they could be planted separately based on fruit color phenotype, and cross-pollination can be reduced or eliminated. Finally, due to the dominant negative nature of at least some of the *virescens* alleles described herein, homozygous *virescens* lines can provide *virescens* palms even if crossed to a *nigrescens* line, whether accidentally or deliberately.

Any marker that exists that is polymorphic between the parent *nigrescens* and *virescens* plant in a cross and is linked to the VIR locus has the potential to serve as a molecular signal to identify *virescens* plants in a cross. For example, if a *virescens* plant, which is homozygous for mutant and dominant "VIR" (i.e., V/V) at a given SNP position near the fruit color locus is crossed with a *nigrescens* plant that is homozygous for wildtype and recessive "vir" (i.e., v/v) at the same SNP position, then one could genotype seeds of the cross, or one could genotype plantlets arising from seeds of the cross, at the SNP position to track and identify contaminant seeds or plantlets. Seeds that are determined to be heterozygous at the SNP position, (i.e., V/v) or homozygous "V" at the SNP position (i.e., V/V) are very likely to be *virescens*, unless (an unlikely) recombination between the marker and the VR gene had occurred in the individual being genotyped. Similarly, seeds which are homozygous at the SNP position for "v", (i.e., v/v), are *nigrescens* contaminant plants and likely to produce fruit that does not change color significantly upon ripening. Markers that are in closer proximity to the VIR locus would have higher predictive accuracy than markers that are farther away from the locus, because the closer the marker is to the VIR gene, the less likely a recombination could occur which would break the linkage between the marker and the VIR gene. Consequently, polymorphic markers within the VIR gene itself are expected to have the strongest predictive power, and analysis of multiple markers closely linked to or within the VIR gene may be advantageous.

II. Determination of Fruit Color Phenotype

In view of the discovery that the VIR genotype segregates with the *virescens/nigrescens* fruit color phenotype, genotyping a plant or seed at the VIR locus or at adjacent genomic regions can be used to predict the fruit color phenotype of a palm plant.

SEQ ID NO:4 represents the predicted amino acid sequence of the protein expressed in oil palm of the *nigrescens* fruit type. In oil palm of the *nigrescens* fruit type, the proteins derived from *nigrescens* alleles of the VIR gene include multiple Myb-type transcription factor DNA binding domains as well as additional C-terminal amino acids.

SEQ ID NOs: 5, 8, 10, 12, and 14 represent the predicted amino acid sequence of proteins encoded by naturally occurring dominant negative alleles in oil palm of the *virescens* fruit type. In some embodiments, endogenous *virescens* protein is a truncation of SEQ ID NO: 4 caused by a premature stop codon. In some cases, the premature stop codon results from a frame shift mutation. In some cases, the premature stop codon results from a rearrangement within the gene. In still other cases, the premature stop codon results from a mutation in one, two, three or more nucleotides within the VIR gene. In other embodiments, the endogenous *virescens* protein is not truncated relative to SEQ ID NO: 4, yet is still dominant negative due to, e.g., a point mutation, insertion, deletion, or other alteration. In some cases, the dominant negative mutation is in exon3 of VIR. In some cases, the endogenous *virescens* allele is recessive. In such cases, the *virescens* phenotype is identified or detected in plants that are homozygous for the recessive *virescens* mutation. A recessive *virescens* mutation can include, for example, a premature stop codon that does not leave a functionally intact DNA binding domain. Alternatively, a recessive *virescens* mutation can contain a mutation that reduces transcription or translation of VIR, or reduces the stability of VIR.

Oil palm plants of the *nigrescens* fruit type can result from at least two possibilities: i) both alleles coding for the SEQ ID NO:4 protein sequence, or ii) one allele coding for a SEQ ID NO:4 protein sequence, and one allele coding for a different sequence that is not dominant negative over the SEQ ID NO:4 allele.

Oil palm plants of the *virescens* fruit type are the result of one of several possibilities, including, but not limited to: i) two VIR alleles, each of which encode for a dominant negative VIR protein such as a VIR protein containing an amino acid sequence selected from the group consisting of SEQ ID NO:5, SEQ 11D NO:8, SEQ ID NO:10, SEQ ID NO:12, and SEQ ID NO:14; ii) one allele coding for a dominant negative VIR protein, such as a VIR protein containing an amino acid sequence selected from the group consisting of SEQ ID NO:5, SEQ ID NO:8, SEQ ID NO:10, SEQ ID NO:12, and SEQ ID NO:14, and one allele coding for SEQ ID NO; 4 or a recessive mutation in SEQ ID NO: 4; or iii) two alleles coding for a recessive mutation in SEQ ID NO:4.

It will be appreciated that SEQ ID NOS:4, 5, 8, 10, 12, and 14 are representative sequences and that different individual palms may have VIR alleles encoding an amino acid sequence having one or more amino acid changes relative to SEQ ID NOS: 4, 5, 8, 10, 12, and 14 due, for example, to natural variation. It will also be appreciated that SEQ ID NOS: 5, 8, 10, 12, and 14, are representative dominant negative mutations and other possible dominant negative mutations are contemplated. For example, mutations that leave the DNA binding domain functionally intact but inactivate one or more interaction or activation domains can be dominant negative. In some cases, mutations in exon 3 of the VIR gene (FIG. 5*a*, bolded), including but not limited to those that introduce premature stop codons in exon 3 of the VIR gene, can be dominant negative.

In some embodiments, mutations upstream and/or downstream of SEQ ID NO:2, including mutations within SEQ ID NO:1 or mutations upstream and/or downstream of SEQ ID NO:1 can give rise to dominant negative or recessive negative VIR alleles. For example, mutations upstream and/or downstream of SEQ ID NO:2 can reduce transcription or translation of VIR. In such cases, *virescens* plants contain two copies of such recessive negative VIR alleles, or one copy of a recessive allele and one copy of a dominant negative allele.

One or more polymorphism(s) between *nigrescens* and *virescens* VIR alleles can be used to predict the fruit color phenotype of a palm or other plant, e.g., before the plant is at a developmental stage to produce fruit. For example, when the *virescens* polymorphism is dominant negative (e.g., a diploid plant with one functional and one non-functional allele has the same phenotype as a plant with two non-functional alleles) then:

the presence of only a *virescens* VIR allele indicates that the plant has or will have a *virescens* fruit color phenotype;

the presence of only a *nigrescens* VIR allele indicates that the plant has or will have a *nigrescens* fruit color phenotype; and the presence of a *nigrescens* VIR allele and a *virescens* VIR allele indicates that the plant has or will have a *virescens* fruit color phenotype.

SEQ ID NOS:6, 7, 9, 11, 13, and 15 represent coding sequences of various naturally occurring dominant negative *virescens* alleles identified.

Genomic regions adjacent to the VIR gene are also useful to determining whether a palm plant will likely manifest a particular fruit color phenotype. Because of genetic linkage to the VIR gene, polymorphisms adjacent to the VIR locus are predictive of fruit color phenotype, albeit with reduced accuracy as a function of increased distance from the VIR locus. SEQ ID NO:17 provides an approximately 2 MB genomic region of the palm genome that comprises the VIR gene. Single nucleotide polymorphisms within this region can be useful predictors of fruit color phenotype. Table 3 provides a listing of some SNPs identified within SEQ ID NO:17. A small selection of the SNPs in Table 3 have been genetically mapped relative to the VIR locus. Table 3 also provides an estimated predictive value for each SNP provided based on the selection of markers mapped.

For example, SNPM02708 and SNPM02400 represent SNPs that are accurate in predicting fruit color phenotype more than 90% of the time. Said another way, using SNPM02708 or SNPM02400 as a genetic marker, one can correctly predict fruit color phenotype of palm plants more than 90 out of 100 times. Thus, even outside of the VIR locus on the palm chromosome, polymorphic markers allow for relatively accurate prediction of fruit color phenotype of plants. In some embodiments, the polymorphic marker is within 1, 10, 20, 50, 100, 200, 500, 1000, 1500, 2000, 2500, 3000, 3500, 400, 4500, or 5000 kb of the VIR gene (e.g., the gene corresponding to SEQ ID NO:1).

Accordingly, methods of detecting one or more polymorphic markers within a region of the palm genome corresponding to SEQ ID) NO:17, or within a region corresponding to SEQ ID NO: 1 are provided. Such methods are useful for predicting fruit color phenotype of palm plants for example. While specific polymorphisms are provided, it should be appreciated that the polymorphisms provided are merely an example of polymorphisms within the genomic region corresponding to SEQ ID NO:17 or SEQ ID NO:1. Additional polymorphisms can be identified as desired and also be used to predict fruit color phenotype of a palm plant. Such additional polymorphisms are intended to be encompassed in the methods described herein. Moreover, it will be appreciated that SEQ ID NO:17 and SEQ ID NO:1 are representative sequences and that different individual palms may have a corresponding genomic region having one or more nucleotide changes relative to SEQ ID NO:17 or SEQ ID NO:1 due, for example, to natural variation. As noted elsewhere herein, nevertheless, identifying the region of a genome corresponding to SEQ ID NO:17 and SEQ ID NO:1 can be readily performed using alignment programs, sequence similarity searches, etc. . . . . .

The nucleic acid sequences provided herein were generated by nucleotide sequencing and on occasion, include one or more stretches of "N's." These stretches of N's represent gaps in assembly of sequences of an estimated size. The precise number of N's in a sequence is an estimate (for example, 100 N's may only represent 30 bases). N's can be any base, and are likely repetitive sequence in the genome.

In some embodiments, fruit color phenotype can be predicted and shell thickness phenotype (e.g., *dura, pisifera*, and *tenera*) can be predicted. In some cases, the fruit color and shell thickness phenotypes can be predicted at the same time, e.g., as part of a single-pass sampling, identification, and/or sorting method. In some cases, the fruit color and shell thickness phenotypes can be predicted using the same nucleic acid sample. For example, a nucleic acid sample can be extracted from a portion of a plant or a seed and teated for the presence or absence of a *viriscens* allele or a polymorphism in linkage disequilibrium with a *virescens* or *nigrescens* allele and tested to predict the shell thickness phenotype of the plant or seed. Methods for predicting SHELL thickness include, but are not limited to, determining the genotype at the SHELL locus, determining the genotype of a polymorphism in linkage disequilibrium with the SHELL locus, determining the genotype of a gene that controls the shell thickness phenotype (e.g., a gene encoding a MADS box protein), or identifying the presence or absence of a polymorphism in linkage disequilibrium with a gene that controls the shell thickness phenotype. Methods, compositions and kits for predicting shell thickness are described, e.g., in PCT Publication No. 2013/142187; U.S. Patent Application No. 61/612,885, filed on Mar. 19, 2012; U.S. Patent Application No. 61/847,853 filed on Jul. 18, 2013; and U.S. Application No. 61/856,433, filed on Jul. 19, 2013, the contents of which are hereby incorporated by reference in their entirety for all purposes.

A. Detection

Described herein are methods for predicting the fruit color phenotype an oil palm plant. Exemplary methods include, but are not limited to contacting oil palm plant nucleic acid containing the VIR gene with an endonuclease (e.g., AseI, or an isoschizomer thereof) that cuts the *nigrescens* VIR allele sequence (SEQ ID NO:1) or a portion thereof, but does not cut the dominant *virescens* allele SEQ ID NO:9 (VIR mutation event 2) or a corresponding portion thereof. Exemplary methods further include, but are not limited to contacting oil palm plant nucleic acid containing the VIR gene with an endonuclease (e.g., AluI, or an isoschizomer thereof) that cleaves the dominant *virescens* allele SEQ ID NO:11 (VIR mutation event 3) or a portion thereof, but does not cleave the *nigrescens* VIR allele SEQ ID NO:1 or a corresponding portion thereof. Exemplary methods further include, but are not limited to contacting oil palm plant nucleic acid containing the VIR gene with an endonuclease (e.g., AseI, or an isoschizomer thereof) that cleaves the dominant *virescens* allele SEQ ID NO:15 (VIR mutation event 5) or a portion thereof, but does not cleave the *nigrescens* VIR allele SEQ ID NO:1 or a corresponding portion thereof. In some cases, the portion thereof in the wild-type sequence or the corresponding portion thereof in the non wild-type sequence is provided as an amplified product (amplicon) or obtained by contacting genomic wild-type or mutated nucleic acid with flanking primers and amplifying.

Exemplary methods also include contacting a portion of oil palm plant nucleic acid with a first endonuclease (e.g., AseI) and a portion of oil palm plant nucleic acid with a second endonuclease (e.g., AluI). In some cases, a portion of the oil palm plant nucleic acid is contacted with additional endonucleases (e.g., contacted with 1, 2, 3, 4, 5, 6, 7, 8, 9, 10, 11, or 12 additional endonucleases). The resulting cleavage patterns can be analyzed to determine the presence or absence of one or more VIR genotypes and thus predict the fruit color phenotype. In some cases, each endonuclease is contacted with oil palm nucleic acid in a separate reaction mixture. In other cases, two or more endonucleases (e.g., 2, 3, 4, 5, 6, 7, 8, 9, 10, 11, or 12 or more endonucleases) are contacted with oil palm nucleic acid in a single reaction mixture. The oil palm plant nucleic acid can be amplified before contact with endonuclease and/or amplified after contact with endonuclease.

More generally, methods for predicting the fruit color phenotype of an oil palm plant include contacting nucleic acid containing the VIR gene with a protein or oligonucleotide that recognizes the VIR gene or a sequence linked to the VIR gene and then detecting recognition (e.g., binding or cleavage). The detection reagent (e.g., protein or oligonucleotide) can be specific for one or more naturally occurring VIR alleles (e.g., SEQ ID NOS:1, 2, 3, 7, 9, 11, 13, or 15). In some cases, the method includes amplifying a VIR gene sequence or a sequence linked to the VIR gene, or a portion of the gene or linked sequence, and detecting the amplification. In some embodiments, the method includes a combination of contacting with a detection reagent and amplification. For example, nucleic acid containing, or linked to, the VIR gene, or a portion thereof, can be amplified, and an oligonucleotide or protein detection reagent (e.g., a restriction enzyme such as Ase I, or Alu I, or an isoschizomer thereof) can be contacted with the amplified nucleic acid. In some cases, further amplification can then be performed. Alternatively, the protein detection reagent can be contacted with nucleic acid containing or linked to the VIR gene, or a portion thereof, then amplified. In some embodiments, alleles, or portions thereof, that are recognized by the detection reagent (e.g., protein or oligonucleotide) are amplified, whereas alleles or portions thereof that are not recognized (e.g., not bound to or cleaved) are not amplified. In other embodiments, alleles that are not recognized by the detection reagent, or portions thereof, are amplified and recognized by the detection agent (e.g., bound to or cleaved) alleles, or portions thereof, are not amplified.

In some embodiments, the methods include amplifying oil palm plant nucleic acid and contacting the amplified nucleic acid with a detection reagent (e.g., an oligonucleotide or a protein). The presence or activity of the detection reagent (e.g., binding or cleavage) can then be assayed as described herein. Alternatively, the nucleic acid can be contacted with the detection reagent, and then amplification can be performed. In some cases, VIR alleles that are not recognized by the detection reagent can be amplified while VIR alleles that are recognized by the detection reagent are not substantially amplified or are not amplified. In some cases, VIR alleles that are recognized by the detection reagent can be amplified while VIR alleles that are not recognized by the detection reagent are not substantially amplified or are not amplified.

1. Endonuclease Detection

In some embodiments, contacting the oil palm nucleic acid (or an amplified portion thereof comprising at least a portion of the VIR gene, or a sequence linked to the VIR gene) with a detection reagent includes contacting the oil palm nucleic acid with an endonuclease that specifically recognizes one or more VIR alleles under conditions that allow for sequence specific cleavage of the one or more recognized alleles. Such conditions will be dependent on the endonuclease employed, but generally include an aqueous buffer, salt (e.g., NaCl), and a divalent cation (e.g., $Mg^2$, $Ca^{2+}$, etc.). The cleavage can be performed at any temperature at which the endonuclease is active, e.g., at least about 5, 7.5, 10, 15, 20, 25, 30, 35, 37, 40, 42, 45, 50, 55, or 65° C. The cleavage can be performed for any length of time such as about 1, 2, 3, 4, 5, 6, 7, 8, 9, 10, 12, 15, 17, 20, 25, 30, 35, 40, 45, 50, 60, 70, 90, 100, 120 minutes; about 2, 3, 4, 5, 6, 7, 8, 10, 12, 14, 16, 18, 20 hours, or about 1, 2, 3, or 4 days. In some cases, the oil palm nucleic acid, or a portion thereof (e.g., the VIR locus, a portion thereof, or sequence linked to the VIR locus) is amplified and then contacted with an endonuclease. Alternatively, the oil palm nucleic acid, or a portion thereof (e.g., the VIR locus, a portion thereof, or sequence linked to the VIR locus) is contacted with an endonuclease and then amplified.

In some cases, cleavage of the nucleic acid prevents substantial amplification; therefore, lack of amplification indicates successful cleavage and thus presence of the allele or alleles recognized by the endonuclease detection reagent. For example, in some cases, amplification can require a primer pair and cleavage can disrupt the sequence of template nucleotides between the primer pair. Thus, in this case, a cleaved sequence will not be amplified, while the uncleaved sequence will be amplified. As another example, cleavage can disrupt a primer binding site thus preventing amplification of the cleaved sequence and allowing amplification of the uncleaved sequence.

Cleavage can be complete (e.g., all, substantially all or greater than 50% of the VIR locus is cleaved or cleavable) or partial (e.g., less than 50% of the VIR locus is cleaved or cleavable). In some cases, complete cleavage can indicate the presence of a recognized VIR allele and the absence of VIR alleles that are not recognized. For example, complete cleavage can indicate that the plant is homozygous for an allele that is recognized by the detection reagent. Similarly, partial cleavage can indicate the presence of both a recognized VIR allele and a VIR allele that is not recognized. For example, partial cleavage can indicate heterozygosity at the VIR locus or heterozygosity at a genomic position linked to the VIR locus.

In some embodiments, two or more endonucleases with differing specificities for one or more VIR alleles are contacted with oil palm nucleic acid. In some cases, the oil palm nucleic acid is, optionally amplified, divided into separate reactions, optionally amplified, and each of the two or more endonucleases added to a separate reaction. One or more control reactions that include, e.g., no endonuclease, no nucleic acid, no amplification, or control nucleic acid can also be included.

After contact with an endonuclease that recognizes one or more alleles but does not recognize one or more other alleles, cleavage can then be detected. Detection of complete cleavage indicates the presence of the allele(s) recognized by the endonuclease. Detection of partial cleavage in the reaction indicates that the nucleic acid is heterozygous for a recognized allele and an allele that is not recognized. Detection of no cleavage in the reaction indicates the absence of the one or more alleles recognized by the endonuclease. Thus, the genotypes and their corresponding fruit color phenotypes (*nigrescens* and *virescens* respectively) can be predicted based on comparing the cleavage pattern of the one or more endonuclease reactions.

Cleavage can be detected by assaying for a change in the relative sizes of oil palm nucleic acid or a portion thereof (e.g., the VIR locus, a portion thereof, or a sequence linked to the VIR locus). For example, oil palm nucleic acid or a portion thereof (e.g., the VIR locus, a portion thereof, or a sequence linked to the VIR locus) can be contacted with one or more endonucleases in a reaction mixture, optionally amplified, the reaction mixture loaded onto an agarose or acrylamide gel, electrophoresed, and the relative sizes of the nucleic acids visualized or otherwise detected. The electrophoresis can be slab gel electrophoresis or capillary electrophoresis. Cleavage can also be detected by assaying for successful amplification of the oil palm nucleic acid or a portion thereof (e.g., the VIR locus, a portion thereof, or a sequence linked to the VIR locus). For example, oil palm nucleic acid or a portion thereof (e.g., the VIR locus, a portion thereof, or a sequence linked to the VIR locus) can be contacted with one or more endonucleases in a reaction mixture, amplified, the reaction mixture loaded onto an agarose or acrylamide gel, electrophoresed, and the presence or absence of one or more amplicons, or the relative sizes of amplicons visualized or otherwise detected.

Detection of cleavage products can be quantitative or semi-quantitative. For example, visualization or other detection can include detection of fluorescent dyes intercalated into double stranded DNA. In such cases, the fluorescent signal is proportional to both the size of the fluorescent DNA molecule and the molar quantity. Thus, after correction for the size of the DNA molecule, the relative molar quantities of cleavage products can be compared. In some cases, quantitative detection provides discrimination between partial and complete cleavage or discrimination between a plant that is homozygous at the VIR locus or heterozygous at the VIR locus.

2. Oligonucleotide Detection

In other embodiments, contacting the oil palm nucleic acid with a detection reagent includes contacting the oil palm nucleic acid or a portion thereof (e.g., the VIR locus, a portion thereof, or a sequence linked to the VIR locus) with an oligonucleotide specific for one or more VIR alleles under conditions which allow for specific hybridization to one or more of the one or more VIR alleles or specific cleavage of one or more of the one or more VIR alleles. Such conditions can include stringent conditions as described herein. Such conditions can also include conditions that allow specific priming of polymerization by the hybridized oligonucleotide at the VIR locus or at a sequence linked to the VIR locus. Detection of hybridization, cleavage, or polymerization can then indicate the presence of the one or more VIR alleles that the oligonucleotide is specific for. Hybridization can be detected by assaying for the presence of the oligonucleotide, the presence of a label linked to the oligonucleotide, or assaying for polymerization of the oligonucleotide. Polymerization of the oligonucleotide can be detected by assaying for amplification as described herein. Polymerization of the oligonucleotide can also be detected by assaying for the incorporation of a detectable label during the polymerization process.

In some embodiments, one or more VIR allies can be detected by annealing one or more primers to template nucleic acid, extending the one or more primers, and then detecting incorporation of one or more nucleotides. For example, a primer extension assay can be performed. Primer extension is a two-step process that first involves the hybridization of a probe to the bases immediately upstream of a nucleotide polymorphism, such as the polymorphisms that give rise to the *nigrescens* or *virescens* phenotypes, followed by a mini-sequencing reaction, in which DNA polymerase extends the hybridized primer by adding one or more bases that are complementary to one or more of the polymorphic sequences. At each position, incorporated bases are detected and the identity of the allele is determined. Because primer extension is based on the highly accurate DNA polymerase enzyme, the method is generally very reliable. Primer extension is able to genotype most polymorphisms under very similar reaction conditions making it also highly flexible. The primer extension method is used in a number of assay formats. These formats use a wide range of detection techniques that include fluorescence, chemiluminescence, directly sensing the ions produced by template-directed DNA polymerase synthesis, MALDI-TOF Mass spectrometry and ELISA-like methods.

Primer extension reactions can, e.g., be performed with either fluorescently labeled dideoxynucleotides (ddNTP) or fluorescently labeled deoxynucleotides (dNTP). With ddNTPs, probes hybridize to the target DNA immediately upstream of polymorphism, and a single, ddNTP complementary to at least one of alleles is added to the 3' end of the probe (the missing 3'-hydroxyl in didioxynucleotide prevents further nucleotides from being added). Each ddNTP is labeled with a different fluorescent signal allowing for the detection of all four possible single nucleotide variations in the same reaction. The reaction can be performed in a multiplex reaction (for simultaneous detection of multiple polymorphisms) by using primers of different lengths and detecting fluorescent signal and length. With dNTPs, allele-specific probes have 3' bases which are complementary to each of the possible nucleotides to be detected. If the target DNA contains a nucleotide complementary to the probe's 3' base, the target DNA will completely hybridize to the probe, allowing DNA polymerase to extend from the 3' end of the probe. This is detected by the incorporation of the fluorescently labeled dNTPs onto the end of the probe. If the target DNA does not contain a nucleotide complementary to the probe's 3' base, the target DNA will produce a mismatch at the 3' end of the probe and DNA polymerase will not be able to extend from the 3' end of the probe. In this case, several labeled dNTPs may get incorporated into the growing strand, allowing for increased signal. Exemplary primer extension methods and compositions include the SNaPshot method. Primer extension reactions can also be performed using a mass spectrometer. The extension reaction can use ddNTPs as above, but the detection of the allele is dependent on the actual mass of the extension product and not on a fluorescent molecule.

In some cases, two or more oligonucleotides with differing specificities for one or more VIR alleles are contacted with oil palm nucleic acid or a portion thereof (e.g., the VIR locus, a portion thereof, or a sequence linked to the VIR locus). In some cases, the two or more oligonucleotides are differentially labeled. In such cases, the contacting can be performed in a single reaction, and hybridization can be differentially detected. Alternatively, the two or more oligonucleotides can be contacted with oil palm nucleic acid that has been separated into two or more reactions, such that each reaction can be contacted with a different oligonucleotide. As yet another alternative, the two or more oligonucleotides can be hybridized to oil palm nucleic in a single reaction, polymerization or amplification performed at the VIR locus, or a sequence linked to the VIR locus, and amplification or polymerization of the template nucleic acid can be differentially detected. For example, one or more of the oligonucleotides can be blocking oligonucleotides such that amplification does not substantially occur when the oligonucleotide is bound. As another example, the two or more oligonucleotides can contain a fluorophore and a quencher, such that amplification of the specifically bound oligonucleotide degrades the oligonucleotide and provides an increase in fluorescent signal. As yet another example, polymerization or amplification can provide polymerization/amplification products of a size that is allele specific. In some cases, one or more control reactions are also included, such as a no-oligonucleotide control, or a positive control containing one or more VIR allele nucleic acid(s).

For example, an oligonucleotide specific for the a *nigrescens* VIR allele, and an oligonucleotide specific for a *virescens* allele can be contacted with oil palm nucleic acid under stringent conditions. Unbound oligonucleotide and/or nucleic acid can then be washed away. Hybridization can then be detected. Hybridization of only the first oligonucleotide would indicate the presence of the *nigrescens* allele, and thus predict a *nigrescens* phenotype. Hybridization of one or more oligonucleotides specific for a dominant *virescens* VIR allele would predict a *virescens* phenotype. Hybridization of an oligonucleotide specific for a recessive *virescens* VIR allele and an oligonucleotide specific for the *nigrescens* VIR allele would predict a *nigrescens* phenotype. Hybridization of an oligonucleotide specific for a recessive *virescens* VIR allele but not an oligonucleotide specific for the *nigrescens* VIR allele would predict a *virescens* phenotype.

As another example, oil palm nucleic acid can be contacted with three oligonucleotides in three different reaction mixtures. The first oligonucleotide can be capable of specifically hybridizing to the wild-type or *nigrescens* allele (e.g., SEQ ID NO:1). The second oligonucleotide can be capable of specifically hybridizing to a dominant *virescens* allele. The third oligonucleotide can be capable of specifically hybridizing to a different dominant *virescens* allele. Additional allele specific oligonucleotides can optionally be utilized. The reaction mixtures can optionally contain another oligonucleotide that specifically hybridizes to the a sequence in the oil palm genome and in combination with any of the first, second, third or more oligonucleotide primers flanks a region, e.g., about 10, 25, 50, 100, 150, 200, 250, 300, 350, 500, 600, 750, 1000, 2000, 5000, 7500, 10000 or more continuous nucleotides, of the oil palm genome at or near the VIR locus. The allele specific oligonucleotides can then be polymerized and the presence or absence of polymerization product detected. For example, PCR can be performed. In some cases, the presence or absence of polymerization product is detected by detection of amplification. In some cases, the presence or absence of polymerization product is detected by detection of a label incorporated during the polymerization.

Differential detection of a polymerization product of each allele specific oligonucleotide would indicate the presence of the corresponding VIR allele. Thus, VIR genotypes can be detected and the resulting phenotypes predicted. In some cases, the polymerization and/or detection can be quantitative or semi-quantitative such that homozygous and heterozygous plants can be distinguished.

As some allele-specific differences in the VIR gene are SNPs, methods useful for SNP detection can also be used to detect the VIR alleles. The amount and/or presence of an allele of a SNP in a sample from an individual can be determined using many detection methods that are well known in the art. A number of SNP assay formats entail one of several general protocols: hybridization using allele-specific oligonucleotides, primer extension, allele-specific ligation, sequencing, or electrophoretic separation techniques, e.g., singled-stranded conformational polymorphism (SSCP) and heteroduplex analysis. Exemplary assays include 5' nuclease assays, template-directed dye-terminator incorporation, molecular beacon allele-specific oligonucleotide assays, single-base extension assays, and SNP scoring by real-time pyrophosphate sequences. Analysis of amplified sequences can be performed using various technologies such as microchips, fluorescence polarization assays, and matrix-assisted laser desorption ionization (MALDI) mass spectrometry. Two methods that can also be used are assays based on invasive cleavage with Flap nucleases and methodologies employing padlock probes.

Determining the presence or absence of a particular SNP allele is generally performed by analyzing a nucleic acid sample that is obtained from a biological sample from the individual to be analyzed. While the amount and/or presence of a SNP allele can be directly measured using RNA from the sample, often times the RNA in a sample will be reverse transcribed, optionally amplified, and then the SNP allele will be detected in the resulting cDNA.

Frequently used methodologies for analysis of nucleic acid samples to measure the amount and/or presence of an allele of a SNP are briefly described. However, any method known in the art can be used in the invention to measure the amount and/or presence of single nucleotide polymorphisms.

3. Allele Specific Hybridization

This technique, also commonly referred to as allele specific oligonucleotide hybridization (ASO) (e.g., Stoneking et al., *Am. J. Hum. Genet.* 48:70-382, 1991; Saiki et al., *Nature* 324, 163-166, 1986; EP 235,726; and WO 89/11548), relies on distinguishing between two DNA molecules differing by one base by hybridizing an oligonucleotide probe that is specific for one of the variants to an amplified product obtained from amplifying the nucleic acid sample. In some embodiments, this method employs short oligonucleotides, e.g., 15-20 bases in length. The probes are designed to differentially hybridize to one variant versus another. Principles and guidance for designing such probe is available in the art, e.g., in the references cited herein. Hybridization conditions should be sufficiently stringent that there is a significant difference in hybridization intensity between alleles, and preferably an essentially binary response, whereby a probe hybridizes to only one of the alleles. Some probes are designed to hybridize to a segment of target DNA or cDNA such that the polymorphic site aligns with a central position (e.g., within 4 bases of the center of the oligonucleotide, for example, in a 15-base oligonucleotide at the 7 position; in a 16-based oligonucleotide at either the 8 or 9 position) of the probe (e.g., a polynucleotide of the invention distinguishes between two SNP alleles as set forth herein), but this design is not required.

The amount and/or presence of an allele is determined by measuring the amount of allele-specific oligonucleotide that is hybridized to the sample. Typically, the oligonucleotide is labeled with a label such as a fluorescent label. For example, an allele-specific oligonucleotide is applied to immobilized oligonucleotides representing potential SNP sequences. After stringent hybridization and washing conditions, fluorescence intensity is measured for each SNP oligonucleotide.

In one embodiment, the nucleotide present at the polymorphic site is identified by hybridization under sequence-specific hybridization conditions with an oligonucleotide probe exactly complementary to one of the polymorphic alleles in a region encompassing the polymorphic site. The probe hybridizing sequence and sequence-specific hybridization conditions are selected such that a single mismatch at the polymorphic site destabilizes the hybridization duplex sufficiently so that it is effectively not formed. Thus, under sequence-specific hybridization conditions, stable duplexes will form only between the probe and the exactly complementary allelic sequence. Thus, oligonucleotides from about 10 to about 35 nucleotides in length, e.g., from about 15 to about 35 nucleotides in length, which are exactly complementary to an allele sequence in a region which encompasses the polymorphic site (e.g., the polymorphisms outlined in SEQ ID NOS:7, 9, 11, 13, 15, 21, 22, 23, or 24) are within the scope of the invention.

In an alternative embodiment, the amount and/or presence of the nucleotide at the polymorphic site is identified by hybridization under sufficiently stringent hybridization conditions with an oligonucleotide substantially complementary to one of the SNP alleles in a region encompassing the polymorphic site, and exactly complementary to the allele at the polymorphic site. Because mismatches that occur at non-polymorphic sites are mismatches with both allele sequences, the difference in the number of mismatches in a duplex formed with the target allele sequence and in a duplex formed with the corresponding non-target allele sequence is the same as when an oligonucleotide exactly complementary to the target allele sequence is used. In this embodiment, the hybridization conditions are relaxed sufficiently to allow the formation of stable duplexes with the target sequence, while maintaining sufficient stringency to preclude the formation of stable duplexes with non-target sequences. Under such sufficiently stringent hybridization conditions, stable duplexes will form only between the probe and the target allele. Thus, oligonucleotides from about 10 to about 35 nucleotides in length, preferably from about 15 to about 35 nucleotides in length, which are substantially complementary to an allele sequence in a region which encompasses the polymorphic site, and are exactly complementary to the allele sequence at the polymorphic site, are within the scope of the invention.

The use of substantially, rather than exactly, complementary oligonucleotides may be desirable in assay formats in which optimization of hybridization conditions is limited. For example, in a typical multi-target immobilized-probe assay format, probes for each target are immobilized on a single solid support. Hybridizations are carried out simultaneously by contacting the solid support with a solution containing target DNA or cDNA. As all hybridizations are carried out under identical conditions, the hybridization conditions cannot be separately optimized for each probe. The incorporation of mismatches into a probe can be used to adjust duplex stability when the assay format precludes adjusting the hybridization conditions. The effect of a particular introduced mismatch on duplex stability is well known, and the duplex stability can be routinely both estimated and empirically determined, as described above. Suitable hybridization conditions, which depend on the exact size and sequence of the probe, can be selected empirically using the guidance provided herein and well known in the art. The use of oligonucleotide probes to detect single base pair differences in sequence is described in, for example, Conner et al., 1983, *Proc. Natl. Acad. Sci. USA* 80:278-282, and U.S. Pat. Nos. 5,468,613 and 5,604,099, each incorporated herein by reference.

The proportional change in stability between a perfectly matched and a single-base mismatched hybridization duplex depends on the length of the hybridized oligonucleotides. Duplexes formed with shorter probe sequences are destabilized proportionally more by the presence of a mismatch. In practice, oligonucleotides between about 15 and about 35 nucleotides in length are preferred for sequence-specific detection. Furthermore, because the ends of a hybridized oligonucleotide undergo continuous random dissociation and re-annealing due to thermal energy, a mismatch at either end destabilizes the hybridization duplex less than a mismatch occurring internally. Preferably, for discrimination of a single base pair change in target sequence, the probe sequence is selected which hybridizes to the target sequence such that the polymorphic site occurs in the interior region of the probe.

The above criteria for selecting a probe sequence that hybridizes to a particular SNP apply to the hybridizing region of the probe, i.e., that part of the probe which is involved in hybridization with the target sequence. A probe may be bound to an additional nucleic acid sequence, such as a poly-T tail used to immobilize the probe, without significantly altering the hybridization characteristics of the probe. One of skill in the art will recognize that for use in the present methods, a probe bound to an additional nucleic acid sequence which is not complementary to the target sequence and, thus, is not involved in the hybridization, is essentially equivalent to the unbound probe.

Suitable assay formats for detecting hybrids formed between probes and target nucleic acid sequences in a sample are known in the art and include the immobilized target (dot-blot) format and immobilized probe (reverse dot-blot or line-blot) assay formats. Dot blot and reverse dot blot assay formats are described in U.S. Pat. Nos. 5,310,893; 5,451,512; 5,468,613; and 5,604,099; each incorporated herein by reference.

In a dot-blot format, amplified target DNA or cDNA is immobilized on a solid support, such as a nylon membrane. The membrane-target complex is incubated with labeled probe under suitable hybridization conditions, unhybridized probe is removed by washing under suitably stringent conditions, and the membrane is monitored for the presence of bound probe.

In the reverse dot-blot (or line-blot) format, the probes are immobilized on a solid support, such as a nylon membrane or a microtiter plate. The target DNA or cDNA is labeled, typically during amplification by the incorporation of labeled primers. One or both of the primers can be labeled. The membrane-probe complex is incubated with the labeled amplified target DNA or cDNA under suitable hybridization conditions, unhybridized target DNA or cDNA is removed by washing under suitably stringent conditions, and the membrane is monitored for the presence of bound target DNA or cDNA.

An allele-specific probe that is specific for one of the polymorphism variants is often used in conjunction with the allele-specific probe for the other polymorphism variant. In some embodiments, the probes are immobilized on a solid support and the target sequence in an individual is analyzed using both probes simultaneously. Examples of nucleic acid arrays are described by WO 95/11995. The same array or a different array can be used for analysis of characterized polymorphisms. WO 95/11995 also describes sub-arrays that are optimized for detection of variant forms of a pre-characterized polymorphism.

In some embodiments, allele-specific oligonucleotide probes can be utilized in a branched DNA assay to differentially detect VIR alleles. For example, allele-specific oligonucleotide probes can be used as capture extender probes that hybridize to a capture probe and VIR in an allele specific manner. Label extenders can then be utilized to hybridize to VIR in a non allele-specific manner and to an amplifier (e.g., alkaline phosphatase). In some cases, a pre-amplifier molecule can further increase signal by binding to the label extender and a plurality of amplifiers. As another example, non allele-specific capture extender probes can be used to capture VIR, and allele-specific label extenders can be used to differentially detect VIR alleles. In some cases, the capture extender probes and/or label extenders hybridize to allele specific VIR cleavage sites (e.g., hybridize to an AseI, or AluI site). In some cases, the probes do not hybridize to VIR DNA that has been cleaved with an allele specific endonuclease (e.g., AseI, or AluI, or an isoschizomer thereof).

4. Allele-Specific Primers

The amount and/or presence of an allele is also commonly detected using allele-specific amplification or primer extension methods. These reactions typically involve use of primers that are designed to specifically target a polymorphism via a mismatch at the 3' end of a primer. The presence of a mismatch affects the ability of a polymerase to extend a primer when the polymerase lacks error-correcting activity. For example, to detect an allele sequence using an allele-specific amplification- or extension-based method, a primer complementary to the polymorphic nucleotide of a SNP is designed such that the 3' terminal nucleotide hybridizes at the polymorphic position. The presence of the particular allele can be determined by the ability of the primer to initiate extension. If the 3' terminus is mismatched, the extension is impeded. If a primer matches the polymorphic nucleotide at the 3' end, the primer will be efficiently extended.

The primer can be used in conjunction with a second primer in an amplification reaction. The second primer hybridizes at a site unrelated to the polymorphic position.

Amplification proceeds from the two primers leading to a detectable product signifying the particular allelic form is present. Allele-specific amplification- or extension-based methods are described in, for example, WO 93/22456; U.S. Pat. Nos. 5,137,806; 5,595,890; 5,639,611; and U.S. Pat. No. 4,851,331.

Using allele-specific amplification-based methods, identification and/or quantification of the alleles require detection of the presence or absence of amplified target sequences. Methods for the detection of amplified target sequences are well known in the art. For example, gel electrophoresis and probe hybridization assays described are often used to detect the presence of nucleic acids.

In an alternative probe-less method, the amplified nucleic acid is detected by monitoring the increase in the total amount of double-stranded DNA in the reaction mixture, is described, e.g., in U.S. Pat. No. 5,994,056; and European Patent Publication Nos. 487,218 and 512,334. The detection of double-stranded target DNA or cDNA relies on the increased fluorescence various DNA-binding dyes, e.g., SYBR Green, exhibit when bound to double-stranded DNA.

Allele-specific amplification methods can be performed in reactions that employ multiple allele-specific primers to target particular alleles. Primers for such multiplex applications are generally labeled with distinguishable labels or are selected such that the amplification products produced from the alleles are distinguishable by size. Thus, for example, both alleles in a single sample can be identified and/or quantified using a single amplification by various methods.

As in the case of allele-specific probes, an allele-specific oligonucleotide primer may be exactly complementary to one of the polymorphic alleles in the hybridizing region or may have some mismatches at positions other than the 3' terminus of the oligonucleotide, which mismatches occur at non-polymorphic sites in both allele sequences.

5. Amplification

Amplification includes any method in which nucleic acid is reproduced, copied, or amplified. In some cases, the amplification produces a copy of the template nucleic acid. In other cases, the amplification produces a copy of a portion of the template nucleic acid (e.g., a copy of the VIR locus, a portion thereof, or a sequence linked to the VIR locus). Amplification methods include the polymerase chain reaction (PCR), the ligase chain reaction (LCR), self-sustained sequence replication (3SR), the transcription based amplification system (TAS), nucleic acid sequence-based amplification (NASBA), strand displacement amplification (SDA), rolling circle amplification (RCA), hyper-branched RCA (HRCA), helicase-dependent DNA amplification (HDA), single primer isothermal amplification, signal-mediated amplification of RNA technology (SMART), loop-mediated isothermal amplification (LAMP), isothermal multiple displacement amplification (IMDA), and circular helicase-dependent amplification (cHDA). The amplification reaction can be isothermal, or can require thermal cycling. Isothermal amplification methods, include but are not limited to, TAS, NASBA, 3SR, SMART, SDA, RCA, LAMP, IMDA, HDA, SPIA, and cHDA. Methods and compositions for isothermal amplification are provided in, e.g., Gill and Ghaemi, *Nucleosides, Nucleotides, and Nucleic Acids,* 27: 224-43 (2008).

Loop-mediated isothermal amplification (LAMP) is described in, e.g., Notomi, et al., *Nucleic Acids Research,* 28(12), e63 i-vii, (2000). The method produces large amounts of amplified DNA in a short period of time. In some cases, successful LAMP amplification can produce pyrophosphate ions in sufficient amount to alter the turbidity, or color of the reaction solution. Thus, amplification can be assayed by observing an increase in turbidity, or a change in the color of the sample. Alternatively, amplified DNA can be observed using any amplification detection method including detecting intercalation of a fluorescent dye and/or gel or capillary electrophoresis.

In some cases, the loop-mediated isothermal amplification (LAMP) is performed with four primers or three or more sets of four primers for amplification of the VIR gene, a portion thereof, or a sequence linked to the VIR gene, including a forward inner primer, a forward outer primer, a backward inner primer, and a backward outer primer. In some cases, one, two, or more additional primers can be used to identify multiple regions or alleles in the same reaction. In some cases, LAMP can be performed with one or more of the following primer sets: a set of wild-type VIR specific primers; a set of primers specific for VIR mutant #1 (e.g., specific for SEQ ID NO:7, or a portion thereof); a set of primers specific for VIR mutant #2 (e.g., specific for SEQ ID NO:9, or a portion thereof); a set of primers specific for VIR mutant #3 (e.g., specific for SEQ ID NO:11, or a portion thereof); a set of primers specific for VIR mutant #4 (e.g., specific for SEQ ID NO:13); and/or a a set of primers specific for VIR mutant #5 (e.g., specific for SEQ ID NO:15, or a portion thereof). In some cases, the oil palm plant DNA is analyzed in two or more separate reaction mixtures. For example, one reaction mixture can be used to amplify wild-type VIR containing oil palm plant nucleic acid, and a second reaction mixture to amplify oil palm plant nucleic acid that contains known dominant VIR mutants (e.g., contains any one of SEQ ID NOS:7, 9, 11, 13, or 15, or a portion thereof).

Amplification detection can include end-point detection or real-time detection. End-point detection can include agarose or acrylamide gel electrophoresis and visualization. For example, amplification can be performed on template nucleic acid that has been contacted with one or more detection reagents (e.g., one or more endonucleases), and then the reaction mixture (or a portion thereof) can be loaded onto an acrylamide or agarose gel, electrophoresed, and the relative sizes of amplicons or the presence or absence of amplicons detected. Alternatively, amplification can be performed, amplicons contacted with one or more detection reagents (e.g., one or more endonucleases), and then the reaction mixture (or a portion thereof) can be loaded onto an acrylamide or agarose gel, electrophoresed, and the relative sizes of amplicons or the presence or absence of amplicons detected. Electrophoresis can include slab gel electrophoresis and capillary electrophoresis.

Real-time detection of amplification can include detection of the incorporation of intercalating dyes into accumulating amplicons, detection of fluorogenic nuclease activity, or detection of structured probes. The use of intercalating dyes utilizes fluorogenic compounds that only bind to double stranded DNA. In this type of approach, amplification product (which in some cases is double stranded) binds dye molecules in solution to form a complex. With the appropriate dyes, it is possible to distinguish between dye molecules remaining free in solution and dye molecules bound to amplification product. For example, certain dyes fluoresce efficiently only when bound to double stranded DNA, such as amplification product. Examples of such dyes include, but are not limited to, SYI3R Green and Pico Green (from Molecular Probes, Inc., Eugene, Oreg.), ethidium bromide, propidium iodide, chromomycin, acridine orange, Hoechst 33258, TOTO-1, YOYO-1, and DAPI (4',6-diamidino-2-phenylindole hydrochloride). Additional discussion regarding the use of intercalation dyes is provided, e.g., by Zhu et al., *Anal. Chem.* 66:1941-1948 (1994).

Fluorogenic nuclease assays are another example of a product quantification method that can be used successfully with the devices and methods described herein. The basis for this method of monitoring the formation of amplification product is to measure PCR product accumulation using a dual-labeled fluorogenic oligonucleotide probe, an approach frequently referred to in the literature as the "TaqMan" method.

The probe used in such assays can be a short (e.g., approximately 20-25 bases in length) polynucleotide that is labeled with two different fluorescent dyes. In some cases, the 5' terminus of the probe can be attached to a reporter dye and the 3' terminus attached to a quenching moiety. In other cases, the dyes can be attached at other locations on the probe. The probe can be designed to have at least substantial sequence complementarity with the probe-binding site on the target nucleic acid. Upstream and downstream PCR primers that bind to regions that flank the probe binding site can also be included in the reaction mixture. When the fluorogenic probe is intact, energy transfer between the fluorophore and quencher moiety occurs and quenches emission from the fluorophore. During the extension phase of PCR, the probe is cleaved, e.g., by the 5' nuclease activity of a nucleic acid polymerase such as Taq polymerase, or by a separately provided nuclease activity that cleaves bound probe, thereby separating the fluorophore and quencher moieties. This results in an increase of reporter emission intensity that can be measured by an appropriate detector. Additional details regarding fluorogenic methods for detecting PCR products are described, for example, in U.S. Pat. No. 5,210,015 to Gelfand, U.S. Pat. No. 5,538,848 to Livak, et al, and U.S. Pat. No. 5,863,736 to Haaland, each of which is incorporated by reference in its entirety, as well as Heid, C. A., et al., *Genome Research,* 6:986-994 (1996); Gibson, U. E. M, et al., *Genome Research* 6:995-1001 (1996); Holland, P. M., et al., *Proc. Natl. Acad. Sci. USA* 4 88:7276-7280, (1991): and Livak, K. J., et al., *PCR Methods and Applications* 357-362 (1995).

Structured probes (e.g., "molecular beacons") provide another method of detecting accumulated amplification product. With molecular beacons, a change in conformation of the probe as it hybridizes to a complementary region of the amplified product results in the formation of a detectable signal. In addition to the target-specific portion, the probe includes additional sections, generally one section at the 5' end and another section at the 3' end, that are complementary to each other. One end section is typically attached to a reporter dye and the other end section is usually attached to a quencher dye. In solution, the two end sections can hybridize with each other to form a stem loop structure. In this conformation, the reporter dye and quencher are in sufficiently close proximity that fluorescence from the reporter dye is effectively quenched by the quencher. Hybridized probe, in contrast, results in a linearized conformation in which the extent of quenching is decreased. Thus, by monitoring emission changes for the reporter dye, it is possible to indirectly monitor the formation of amplification product. Probes of this type and methods of their use is described further, for example, by Piatek, A. S., et al., *Nat. Biotechnol.* 16:359-63 (1998); Tyagi, S, and Kramer, F. R., *Nat. Biotechnol.* 14:303-308 (1996); and Tyagi, S. et al., *Nat. Biotechnol.* 16:49-53 (1998).

Detection of amplicons can be quantitative or semi-quantitative whether performed as a real-time analysis or as an end-point analysis. In general, the detection signal (e.g., fluorescence) is proportional to the molar quantity of the amplicon. Thus, the relative molar quantities of amplicons can be compared. In some cases, quantitative detection provides discrimination between a plant that is homozygous at the VIR locus or heterozygous at the VIR locus.

As described herein, hybridization, cleavage, and amplification methods can be combined. For example, oil palm plant nucleic acid can be hybridized to one or more oligonucleotides, cleaved and then amplified. Alternatively, oil palm plant nucleic acid can be amplified, cleaved, and then amplified again, or the cleavage products detected by hybridization with an oligonucleotide detection reagent.

In certain embodiments, polymorphic markers are detected by sequencing technologies. Obtaining sequence information about an individual plant identifies particular nucleotides in the context of a sequence. For SNPs, sequence information about a single unique sequence site is sufficient to identify alleles at that particular SNP. For markers comprising more than one nucleotide, sequence information about the nucleotides of the individual that contain the polymorphic site identifies the alleles of the individual for the particular site.

Various methods for obtaining nucleic acid sequence are known to the skilled person, and all such methods are useful for practicing the invention. Sanger sequencing is a well-known method for generating nucleic acid sequence information. Recent methods for obtaining large amounts of sequence data have been developed, and such methods are also contemplated to be useful for obtaining sequence information of a plant, if desired. These include pyrosequencing technology (Ronaghi, M. et al. *Anal Biochem* 267:65-71 (1999); Ronaghi, et al., *Biotechniques* 25:876-878 (1998)), e.g. 454 pyrosequencing (Nyren, P., et al. *Anal Biochem* 208:171-175 (1993)), Illumina/Solexa sequencing technology (available one the world wide web at illumina.com; see also Strausberg, R L, et al. *Drug Disc Today* 13:569-577 (2008)), and Supported Oligonucleotide Ligation and Detection Platform (SOLiD) technology (Applied Biosystems, available on the world wide web at appliedbiosystems.com); Strausberg, R L, et al. *Drug Disc Today* 13:569-577 (2008).

B. Sampling and Sorting

Oil palm nucleic acid can be obtained from any suitable tissue of an oil palm plant. For example, oil palm nucleic acid can be obtained from a leaf, a stem, a root or a seed. In some cases, the oil palm nucleic acid is obtained from endosperm tissue of a seed. In some cases, the oil palm nucleic acid is obtained in such a manner that the oil palm plant or seed is not reduced in viability or is not substantially reduced in viability. For example, in some cases, sample extraction can reduce the number of viable plants or seeds in a population by less than about 20%, 15%, 10%, 5%, 2.5%, 1%, or less. In some cases, the sample is obtained from the embryo free region of an oil palm seed.

In some embodiments, endosperm material can be extracted from a sampling zone of a seed with a needle or probe that penetrates the seed shell and enters a sampling zone and avoids an embryo containing zone. The sampled material or fluid can further be purified from contaminating maternal DNA by removing fragments of the seed shell that might be present in the endosperm sample. In some cases, endosperm DNA can then be extracted from the endosperm material or fluid. Alternatively, oil palm nucleic acid can be obtained from a seedling, an immature (e.g. non fruit bearing) plant, or a mature plant.

Samples can be extracted by grinding, cutting, slicing, piercing, needle coring, needle aspiration or the like. Sampling can be automated. For example, a machine can be used to take samples from a plant or seed, or to take samples from a plurality of plants or seeds. Sampling can also be performed manually. Further sampling methodologies are described herein.

In some embodiments, the sampling is controlled to deter contamination of the sample. For example, washing steps can be employed between sample processing steps. Alternatively, disposable or removable sample handling elements can be utilized, e.g., disposable pipetting tips, disposable receptacles or containers, or disposable blades or grinders.

In some cases, samples are purified prior to detection of VIR genotype or prediction of fruit color phenotype. For example, samples can be centrifuged, extracted, or precipitated. Additional methods for purification of plant nucleic acids are known by those of skill in the art.

In some embodiments, a seed or plant fruit color phenotype is predicted, and the seed or plant is sorted based on the predicted phenotype. For example, the seed or plant can be sorted into *nigrescens* or *virescens* seeds or plants based on their predicted phenotype. *Nigrescens* and *virescens* seeds or plants can be sorted and stored separately as breeding stock for the generation of plants with the desired fruit form phenotype. *Virescens* seeds or plants can also be planted and cultivated for the enhanced oil yield they provide. In some cases, the plant is a seed and the sorting is performed on the seed. Alternatively, the plant is a seedling and the sorting is performed on the seedling before it is planted in the field or before its use in breeding. As yet another alternative, oil palm plants that have been planted in the field for optimal palm oil yield, but are not mature enough to verify fruit color phenotype can be assayed and *nigrescens* plants can be removed from the field.

In some embodiments, a seed or plant fruit color and shell thickness phenotype is predicted, and the seed or plant is sorted based on one or both of the predicted phenotypes. For example, the seed or plant can be sorted into *nigrescens* or *virescens* seeds or plants and *dura, tenera,* or *pisifera* seeds or plants based on their predicted phenotypes. *Nigrescens* and *virescens* versions of *dura, tenera,* or *pisifera* seeds or plants can be sorted and stored separately as breeding stock for the generation of plants with the desired fruit form phenotype. Seeds or plants having, e.g., a *viriscens* and a *tenera* predicted phenotype can also be planted and cultivated for the enhanced oil yield they provide. Other combinations of fruit color and shell thickness predicted phenotypes can also be stored, separated, planted, or discarded based on their predicted phenotypes. In some cases, the plant is a seed and the sorting is performed on the seed. Alternatively, the plant is a seedling and the sorting is performed on the seedling before it is planted in the field or before its use in breeding. As yet another alternative, oil palm plants that have been planted in the field for optimal palm oil yield, but are not mature enough to verify fruit color phenotype can be assayed and *nigrescens* and/or *dura* or *pisifera* plants can be removed from the field.

Methods of polymorphism detection can be performed on any type of biological sample from the plant that contains nucleic acids (e.g., DNA, or RNA). One particular advantage of the methods is to predict the fruit color phenotype of young plants before cultivation in the field. Therefore, in some embodiments, the samples are obtained from a plant that has been germinated and then cultivated less than 1, 2, 4, 6, months or less than 1, 2, 3, 4, or 5 years. In some embodiments, the samples are obtained before the plant has been germinated (e.g., from a seed) or shortly thereafter (e.g. less than about 1, 2, 3, 4, or 5 weeks after germination).

In some embodiments, the plants are generated from i) a cross between *nigrescens* and *virescens* palms ii) the selfing of a *virescens* palm, iii) a cross between two plants having the *virescens* fruit color phenotype, iv) selfing of a *nigrescens* palm, or v) a cross between two *nigrescens* palms. Because such crosses are not 100% efficient, parent plants are not necessarily true breeding (e.g., heterozygote parents), and VIR alleles can be dominant, dominant negative, or recessive, such crosses can result in an unpredictable percentage of seeds or plants with the *virescens* fruit color phenotype. By testing seeds or plants resulting from the attempted crosses, one can reduce or eliminate non-*virescens* contaminant seeds or plants from material planted for cultivation (optionally discarding those plants that are predicted to be *nigrescens*). Alternatively, one can identify and segregate plants based on their predicted fruit color phenotype, allowing for selection and cultivation of fields of pure *nigrescens* or *virescens* plants, if desired, e.g., for later breeding purposes.

I. Systems and Machine for Sampling and/or Sorting

Machines can be utilized to carry out one or more methods described herein, prepare plant samples for one or more methods described herein, or facilitate high throughput sorting of oil palm plants.

In some cases, a machine can sort and orient seeds such that the seed are all oriented in a similar manner. The seeds for example, can be oriented such that embryo region of the seed is down and the embryo free region is oriented up. In some cases, the seeds can be placed into an ordered array or into a single line.

In some embodiments, the seed is held in pre-determined orientation to facilitate efficient and accurate sampling. For example, the machine can orient the seeds by seed shape or visual appearance. In some cases, the seed is oriented to facilitate sampling from the 'Crown' of each respective seed, containing the cotyledon and/or endosperm tissue of the seed, so that the germination viability of each seed is preserved.

In some cases, the machine can separately store plants or seeds and their extracted samples without reducing, or without substantially reducing the viability of the seeds. In some cases, the extracted samples and stored plants or seeds are organized, labeled, or catalogued in such a way that the sample and the seed from which it is derived can be determined. In some cases, the extracted samples and stored plants or seeds are tracked so that each can be accessed after data is collected. For example, a sample can be extracted from a seed and the VIR genotype determined for the sample, and thus the seed. The seed can then be accessed and planted, stored, or destroyed based on the predicted fruit color phenotype.

In some cases, the extraction and storing are performed automatically by the machine, but the genotype analysis and/or treatment of analyzed seeds performed manually or performed by another machine. As such, in some embodiments, a system is provided consisting of two or more machines for extraction of seed samples, seed sorting and storing, and prediction of fruit color phenotype.

In some cases, the plants or seed are stored in an array by the machine, such as individually in an array of tubes or wells. The plants can be sampled and/or interrogated in or from each well. The results of the sampling or interrogating can be correlated with the position of the plant in the array.

Sampling can include extraction and/or analysis of nucleic acid (e.g., DNA or RNA), magnetic resonance imaging, optical dispersion, optical absorption, ELISA, enzymatic assay, or the like.

Systems, machines, methods and compositions for seed sampling and/or sorting are further described in, e.g., U.S. Pat. Nos. 6,307,123; 6,646,264; 7,367,155; 8,312.672; 7,685,768; 7,673,572; 8,443,545; 7,998.669; 8,362,317; 8,076,076; 7,402,731; 7,600,642; 8,237,016; 8,401,271; 8,281,935; 8,241,914; 6,880,771; 7,909,276; 8,221,968; and 7,454,989. Systems, machines, methods and compositions for seed sampling and/or sorting are also further described in, e.g., U.S. Patent Application Publication NOs: 2012/180386; 2009/070891; 2013/104454, 2012/117865, 2008/289061; 2008/000815; 2011/132721; 2011/195866; 2011/0079544; 2010/0143906; and 2013/079917. Additional systems, machines, methods, and compositions for seed sampling are further described in international patent application publications WO2011/119390; and WO2011/119394.

Also provided herein are methods for using the systems, machines, methods, and compositions described herein for seed sampling or sorting. For example, a seed or set of seeds can be loaded into a seed sampler, and a sample obtained. In some cases, the seed can be stored, e.g., in an array. In some cases, the storage is performed by the machine that samples the seed. In other cases, the seed is stored by another machine, or stored manually. In some cases, DNA can be extracted from the sample. In some cases, sample can be obtained and DNA extracted by the same machine. In other cases, the DNA is extracted by another machine, or manually. The extracted DNA can be analyzed and the VIR genotype determined. In some cases, the extracted DNA is analyzed by the same machine, by another machine, or manually. In some cases, fruit color phenotype is predicted from the VIR genotype by the machine, a different machine, or manually. In some cases, stored seeds can be disposed of (e.g., cultivated or destroyed) based on the VIR genotype or predicted fruit color phenotype. In some cases, stored seeds can be disposed of based on the VIR genotype or predicted fruit color phenotype and based on their predicted shell thickness phenotype. In some cases, the seed is disposed of by the machine, a different machine, or manually.

In some cases, the seed or seeds are shipped from a customer to a service provider, analyzed, and returned. In some cases, only seeds with a predicted phenotype or phenotypes are returned. For example, only *virescens* or only *nigrescens*, or a combination thereof are returned. In other cases, seeds are sampled, and the samples are shipped from a customer to a service provider for analysis. The customer can then utilize information provided by the analysis to dispose of the seeds.

In some cases, reagents, such as the compositions described herein are provided for sampling of seeds manually or automatically. For example, endonucleases, oligonucleotide primers or probes, or a combination thereof as described herein can be provided. As another example, reaction mixtures containing reagents necessary for analysis of nucleic acid from an oil palm plant can be provided.

IV. Transgenic Plants

As discussed above, the VIR gene of palm has been discovered to control fruit color phenotype. Thus in some embodiments, plants having modulated expression of a VIR polypeptide are provided. One desirable fruit color phenotype (*virescens*, having fruit color that changes from green to reddish orange upon ripening) occurs naturally as either a homozygote (e.g., two recessive mutations of the wild-type VIR allele), or as a heterozygote (e.g., at least one dominant negative mutation of wild-type the VIR allele).

*virescens*-type VIR alleles can result in plants that do not express sufficient functional VIR. Accordingly, in some embodiments, plants having reduced level of functional VIR protein compared to a *nigrescens* plant are provided. Such plants can be generated, for example, using gene inhibition technology, including but not limited to siRNA technology, to reduce, or eliminate, endogenous VIR gene expression of an active VIR protein (e.g., in a *nigrescens* background).

Alternatively, a heterologous expression cassette (i.e., a transgene) can be introduced into a *nigrescens* background where the expression cassette promotes expression of a dominant negative VIR allele. This can be achieved, for example, by operably linking a suitable promoter to mutated VIR gene, such as those provided in SEQ ID NOS:6, 7, 9, 11, 13, or 15, or a fragment thereof that contains a Myb-like DNA binding domain. In some cases, the VIR gene or fragment utilized may contain additional sequence encoding for additional C-terminal amino acids. Alternatively, a fragment of the wild-type VIR gene (e.g., a fragment of SEQ ID NO:1) may be utilized. In yet other embodiments, a VIR gene substantially similar to the wild-type may be utilized as a dominant negative as long as it contains a mutation, such as a point mutation, that renders the C-terminal domain inactive or substantially inactive, but does not substantially interfere with one or more of the DNA binding domains. Suitable promoters that can be operably linked to the genes or gene fragments provided above include, but are not limited to strong promoters like CaMV 35S, and native promoters like the native VIR gene promoter.

A. Inhibition or Suppression of Gene Expression

Methods for controlling the fruit color trait in a palm (e.g., oil palm, coconut, or date palm) or other plant are provided by reducing expression of an endogenous nucleic acid molecule encoding a VIR polypeptide. For example, in a transgenic plant, a nucleic acid molecule, or antisense, siRNA, microRNA, or dsRNA constructs thereof, targeting a VIR gene product, or fragment thereof, or a VIR mRNA, or fragment thereof can be operatively linked to an exogenous regulatory element, wherein expression of the construct suppresses endogenous VIR expression.

A number of methods can be used to inhibit gene expression in plants. For instance, antisense technology can be conveniently used. To accomplish this, a nucleic acid segment from the desired gene is cloned and operably linked to a promoter such that the antisense strand of RNA will be transcribed. The expression cassette is then transformed into plants and the antisense strand of RNA is produced. In plant cells, it has been suggested that antisense RNA inhibits gene expression by preventing the accumulation of mRNA which encodes the protein of interest, see, e.g., Sheehy et al., *Proc. Nat. Acad. Sci. USA,* 85:8805-8809 (1988); Pnueli et al., *The Plant Cell* 6:175-186 (1994); and Hiatt et al., U.S. Pat. No. 4,801,340.

The antisense nucleic acid sequence transformed into plants will be substantially identical to at least a portion of the endogenous gene or genes to be repressed. The sequence, however, does not have to be perfectly identical to inhibit expression. For example, an antisense or sense nucleic acid molecule encoding only a portion of a VIR-encoding sequence can be useful for producing a plant in which VIR expression is suppressed. The vectors of the present invention can be designed such that the inhibitory effect applies to other proteins within a family of genes exhibiting homology or substantial homology to the target gene, or alternatively such that other family members are not substantially inhibited.

For antisense suppression, the introduced sequence also need not be full length relative to either the primary transcription product or mature mRNA (e.g., SEQ ID NO:3 or polyadenylated SEQ ID NO:3). Generally, higher homology can be used to compensate for the use of a shorter sequence. Furthermore, the introduced sequence need not have the same intron or exon pattern, and homology of non-coding segments may be equally effective. In some embodiments, a sequence of at least, e.g., 15, 20, 25 30, 50, 100, 200, or more continuous nucleotides (up to mRNA full length) substantially identical to an endogenous VIR mRNA, or a complement or reverse complement thereof, can be used.

Catalytic RNA molecules or ribozymes can also be used to inhibit expression of VIR genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs.

A number of classes of ribozymes have been identified. One class of ribozymes is derived from a number of small circular RNAs that are capable of self-cleavage and replication in plants. The RNAs replicate either alone (viroid RNAs) or with a helper virus (satellite RNAs). Examples include RNAs from avocado sunblotch viroid and the satellite RNAs from tobacco ringspot virus, lucerne transient streak virus, velvet tobacco mottle virus. *Solanum nodiflorum* mottle virus and subterranean clover mottle virus. The design and use of target RNA-specific ribozymes is described in Haseloff et al. *Nature,* 334:585-591 (1988).

Another method of suppression is sense suppression (also known as co-suppression). Introduction of expression cassettes in which a nucleic acid is configured in the sense orientation with respect to the promoter has been shown to be an effective means by which to block the transcription of target genes. For an example of the use of this method to modulate expression of endogenous genes see, Napoli et al., *The Plant Cell* 2:279-289 (1990); Flavell, *Proc. Natl. Acad. Sci., USA* 91:3490-3496 (1994); Kooter and Mol, *Current Opin. Biol.* 4:166-171 (1993); and U.S. Pat. Nos. 5,034,323, 5,231,020, and 5,283.184.

Generally, where inhibition of expression is desired, some transcription of the introduced sequence occurs. The effect may occur where the introduced sequence contains no coding sequence per se, but only intron or untranslated sequences homologous to sequences present in the primary transcript of the endogenous sequence. The introduced sequence generally will be substantially identical to the endogenous sequence intended to be repressed. This minimal identity will typically be greater than about 65%, but a higher identity might exert a more effective repression of expression of the endogenous sequences. In some embodiments, the level of identity is more than about 80% or about 95%. As with antisense regulation, the effect can apply to any other proteins within a similar family of genes exhibiting homology or substantial homology and thus which area of the endogenous gene is targeted will depend whether one wished to inhibit, or avoid inhibition, of other gene family members.

For sense suppression, the introduced sequence in the expression cassette, needing less than absolute identity, also need not be full length, relative to either the primary transcription product or fully processed mRNA. This may be preferred to avoid concurrent production of some plants that are overexpressers. A higher identity in a shorter than full length sequence compensates for a longer, less identical sequence. Furthermore, the introduced sequence need not have the same intron or exon pattern, and identity of non-coding segments will be equally effective. Normally, a sequence of the size ranges noted above for antisense regulation is used.

Endogenous gene expression may also be suppressed by way of RNA interference (RNAi), which uses a double-stranded RNA having a sequence identical or similar to the sequence of the target gene. RNAi is the phenomenon in which when a double-stranded RNA having a sequence identical or similar to that of the target gene is introduced into a cell, the expressions of both the inserted exogenous gene and target endogenous gene are suppressed. The double-stranded RNA may be formed from two separate complementary RNAs or may be a single RNA with internally complementary sequences that form a double-stranded RNA. Although details of the mechanism of RNAi are still unknown, it is considered that the introduced double-stranded RNA is initially cleaved into small fragments, which then serve as indexes of the target gene in some manner, thereby degrading the target gene. RNAi is known to be also effective in plants (see. e.g., Chuang, C. F. & Meyerowitz, E. M., *Proc. Natl. Acad. Sci.* (*USA* 97: 4985 (2000); Waterhouse et al., *Proc. Natl. Acad. Sci. USA* 95:13959-13964 (1998); Tabara et al. *Science* 282:430-431 (1998)). For example, to achieve suppression of the expression of a DNA encoding a protein using RNAi, a double-stranded RNA having the sequence of a DNA encoding the protein, or a substantially similar sequence thereof (including those engineered not to translate the protein) or fragment thereof, is introduced into a plant of interest. The resulting plants may then be screened for a phenotype associated with the target protein and/or by monitoring steady-state RNA levels for transcripts encoding the protein. Although the genes used for RNAi need not be completely identical to the target gene, they may be at least 70%, 80%, 90%, 95% or more identical to the target gene sequence. See, e.g., U.S. Patent Publication No. 2004/0029283. The construct encoding an RNA molecule with a stem-loop structure that is unrelated to the target gene and that is positioned distally to a sequence specific for the gene of interest may also be used to inhibit target gene expression. See, e.g., U.S. Patent Publication No. 2003/0221211.

The RNAi polynucleotides may encompass the full-length target RNA or may correspond to a fragment of the target RNA. In some cases, the fragment will have fewer than 100, 200, 300, 400, 500 600, 700, 800, 900 or 1,000 nucleotides corresponding to the target sequence. In addition, in some embodiments, these fragments are at least, e.g., 50, 100, 150, 200, or more nucleotides in length. In some cases, fragments for use in RNAi will be at least substantially similar to regions of a target protein that do not occur in other proteins in the organism or may be selected to have as little similarity to other organism transcripts as possible, e.g., selected by comparison to sequences in analyzing publicly-available sequence databases.

Expression vectors that continually express siRNA in transiently- and stably-transfected plants have been engineered to express small hairpin RNAs, which get processed in vivo into siRNAs molecules capable of carrying out gene-specific silencing (Brummelkamp et al., *Science* 296: 550-553 (2002), and Paddison, et al., *Genes & Dev.* 16:948-958 (2002)). Post-transcriptional gene silencing by double-stranded RNA is discussed in further detail by Hammond et al. *Nature Rev Gen* 2: 110-119 (2001), Fire et al. *Nature* 391: 806-811 and Timmons and Fire *Nature* 395: 854 (1998).

One of skill in the art will recognize that using technology based on specific nucleotide sequences (e.g., antisense or sense suppression, siRNA, microRNA technology, etc.), families of homologous genes can be suppressed with a single sense or antisense transcript. For instance, if a sense or antisense transcript is designed to have a sequence that is conserved among a family of genes, then multiple members of a gene family can be suppressed. Conversely, if the goal is to only suppress one member of a homologous gene family, then the sense or antisense transcript should be targeted to sequences with the most variance between family members.

Yet another way to suppress expression of an endogenous plant gene is by recombinant expression of a microRNA that suppresses a target (e.g., a VIR gene). Artificial microRNAs are single-stranded RNAs (e.g., between 18-25 mers, generally 21 mers), that are not normally found in plants and that are processed from endogenous miRNA precursors. Their sequences are designed according to the determinants of plant miRNA target selection, such that the artificial microRNA specifically silences its intended target gene(s) and are generally described in Schwab et al., *The Plant Cell* 18:1121-1133 (2006) as well as the internet-based methods of designing such microRNAs as described therein. See also, US Patent Publication No. 2008/0313773.

B. Use of Nucleic Acids of the Invention to Enhance Gene Expression

Nucleic acid sequences encoding all or an active part of a VIR polypeptide (including but not limited to polypeptides substantially identical to SEQ ID NOS:5, 8, 10, 12, or 14, or VIR polypeptides having a functional DNA binding domain and one or more non-functional domains (e.g., a VIR polypeptide truncated C-terminal to one or more DNA binding domains), which when expressed control fruit color) can be used to prepare expression cassettes that enhance, or increase expression of dominant negative VIR alleles. Alternatively, nucleotide sequences encoding all or an active part of a VIR polypeptide (including but not limited to polypeptides substantially identical to SEQ ID NO:4) can be used to prepare expression cassettes that enhance or increase expression of VIR. Where overexpression of a gene is desired in a background that contains a copy of the same gene or a copy of a gene substantially similar, the desired VIR gene from a different species may be used to decrease potential sense suppression effects. Alternatively, co-suppression may be reduced by introducing silent mutations into the VIR gene of the expression cassette that do not alter the amino acid coding sequence, but reduce the similarity to the endogenous gene.

Any of a number of means well known in the art can be used to increase VIR activity in plants. Any organ can be targeted, such as shoot vegetative organs/structures (e.g. leaves, stems and tubers), roots, flowers and floral organs/structures (e.g. bracts, sepals, petals, stamens, carpels, anthers and ovules), seed (including embryo, endosperm, and seed coat) and fruit. Alternatively, a VIR gene can be expressed constitutively (e.g., using the CaMV 35S promoter).

One of skill will recognize that the polypeptides encoded by the genes of the invention, like other proteins, have different domains which perform different functions. Thus, the gene sequences need not be full length, so long as the desired functional domain of the protein is expressed.

V. Preparation of Recombinant Vectors

In some embodiments, to use isolated sequences in the above techniques, recombinant DNA vectors suitable for transformation of plant cells are prepared. Techniques for transforming a wide variety of higher plant species are well known and described in the technical and scientific literature. See, for example. Weising et al. *Ann. Rev. Genet.* 22:421-477 (1988). A DNA sequence coding for the desired polypeptide, for example a cDNA sequence encoding a full length protein, will preferably be combined with transcriptional and translational initiation regulatory sequences which will direct the transcription of the sequence from the gene in the intended tissues of the transformed plant.

For example, for overexpression, a plant promoter fragment may be employed which will direct expression of the gene in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumefaciens*, and other transcription initiation regions from various plant genes known to those of skill.

Alternatively, the plant promoter may direct expression of the polynucleotide of the invention in a specific tissue (tissue-specific promoters) or may be otherwise under more precise environmental control (inducible promoters). Examples of tissue-specific promoters under developmental control include promoters that initiate transcription only in certain tissues, such as fruit, seeds, or flowers. Examples of environmental conditions that may affect transcription by inducible promoters include anaerobic conditions, elevated temperature, or the presence of light.

If proper polypeptide expression is desired, a polyadenylation region at the 3'-end of the coding region should be included. The polyadenylation region can be derived from the natural gene, from a variety of other plant genes, or from T-DNA.

The vector comprising the sequences (e.g., promoters or coding regions) from genes of the invention can optionally comprise a marker gene that confers a selectable phenotype on plant cells. For example, the marker may encode biocide resistance, particularly antibiotic resistance, such as resistance to kanamycin, G418, bleomycin, hygromycin, or herbicide resistance, such as resistance to chlorosluforon or Basta.

VIR nucleic acid operably linked to a promoter is provided that, in some embodiments, is capable of driving the transcription of the VIR coding sequence in plants, such as a wild-type VIR coding sequence or a dominant negative VIR coding sequence. The promoter can be, e.g., derived from plant or viral sources. The promoter can be, e.g., constitutively active, inducible, or tissue specific. In construction of recombinant expression cassettes, vectors, transgenics, of the invention, a different promoters can be chosen and employed to differentially direct gene expression, e.g., in some or all tissues of a plant or animal. In some embodiments, as discussed above, desired promoters are identified by analyzing the 5' sequences of a genomic clone corresponding to a VIR gene as described here. For examples, desired promoters may be found in the region of SEQ ID NOS:1 or 17 that are 5' of the VIR gene.

VI. Production of Transgenic Plants

DNA constructs of the invention may be introduced into the genome of the desired plant host by a variety of conventional techniques. For example, the DNA construct may be introduced directly into the genomic DNA of the plant cell using techniques such as electroporation and microinjection of plant cell protoplasts, or the DNA constructs can be introduced directly to plant tissue using ballistic methods, such as DNA particle bombardment. Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria.

Various palm transformation methods have been described. See, e.g., Masani and Parveez, *Electronic Journal of Biotechnology* Vol. 11 No. 3, Jul. 15, 2008; Chowdury et al., *Plant Cell Reports*, Volume 16, Number 5, 277-281 (1997).

Microinjection techniques are known in the art and well described in the scientific and patent literature. The introduction of DNA constructs using polyethylene glycol precipitation is described in Paszkowski et al. *EMBO J.* 3:2717-2722 (1984). Electroporation techniques are described in Fromm et al. *Proc. Natl. Acad. Sci. USA* 82:5824 (1985). Ballistic transformation techniques are described in Klein et al. *Nature* 327:70-73 (1987).

*Agrobacterium tumefaciens*-mediated transformation techniques, including disarming and use of binary vectors, are well described in the scientific literature. See, for example Horsch et al. *Science* 233:496-498 (1984), and Fraley et al. *Proc. Natl. Acad. Sci. USA* 80:4803 (1983).

Transformed plant cells that are derived from any transformation technique can be cultured to regenerate a whole plant that possesses the transformed genotype and thus the desired phenotype. Such regeneration techniques rely on manipulation of certain phytohormones in a tissue culture growth medium, optionally relying on a biocide and/or herbicide marker that has been introduced together with the desired nucleotide sequences. Plant regeneration from cultured protoplasts is described in Evans et al., *Protoplasts Isolation and Culture, Handbook of Plant Cell Culture*, pp. 124-176, MacMillilan Publishing Company, New York, 1983; and *Binding, Regeneration of Plants, Plant Protoplasts*, pp. 21-73, CRC Press, Boca Raton, 1985. Regeneration can also be obtained from plant callus, explants, organs, or parts thereof. Such regeneration techniques are described generally in Klee et al. *Ann. Rev. of Plant Phys.* 38:467-486 (1987).

The nucleic acids of the invention can be used to confer desired traits on essentially any plant. Thus, the invention has use over a broad range of plants, including species from the genera *Asparagus, Atropa, Avena, Brassica, Citrus, Citrullus, Capsicum, Cucumis, Cucurbita, Daucus, Fragaria, Glycine, Gossypium, Itelianthus, Ileterocallis, Ilordeum, Hysocyamus, Lactuca, Linum, Lolium, Lycopersicon, Malus, Manihot, Majorana, Medicago, Nicotiana, Oryza, Panieum, Pannesetum, Persea, Pisum, Pvrus, Prunus, Raphanus. Secale, Senecio, Sinapis, Solanum, Sorghum, Trigonella, Triticum, Vitis, Vigna,* and, *Zea*. Plants that fruit, and have use in the present invention, include but are not limited to dicotyledons and monocotyledons including but not limited to palm, such as oil palm.

VII. Kits

Described herein are kits for the prediction of fruit color phenotype of an oil palm plant. The kit can contain one or more endonucleases. In some cases, each endonuclease is specific for one or more VIR alleles. For example, each endonuclease can recognize and cleave a sequence at or near one or more VIR alleles or a portion thereof, but does not recognize or cleave a sequence at or near at least one other VIR allele or a portion thereof. In some cases, the one or more endonucleases is AseI, AluI, or an isoschizomer thereof.

The kit can contain one or more oligonucleotide primers for amplification at or near the VIR locus. For instance, the kit can include at least one primer that primes amplification of at least a portion of one or more of the following VIR alleles: SEQ ID NOS:1, 3, 7, 9, 11, 13, or 15, or a primer pair that generates an amplicon comprising at least a portion of SEQ ID NOS:1, 3, 7, 9, 11, 13, or 15.

In some cases, the primer is specific for one or more VIR alleles. For example, the primer can hybridize to, and prime polymerization of, a region at or near one or more VIR alleles but does not hybridize to, or primer polymerization of, a region at or near one or more other VIR alleles. In other cases, the primer can hybridize to, or prime polymerization of, a region at or near (e.g., within less than about 10,000 bp; 5,100 bp; 1,000 bp; 500 bp; 250 bp; 100 bp; 50 bp; 25 bp: 15 bp; or fewer) a AseI, AluI, or ApoI site of a VIR allele. In some cases, the oligonucleotide primer contains at least 10, 12, 15 or more contiguous nucleotides comprising a portion of SEQ ID NOS:1, 3, 7, 9, 11, 13, 15, or 17 or a reverse complement thereof. In some cases, the primer can provide, e.g. alone or in combination with other primers, for amplification such as isothermal amplification or PCR.

In some cases, the kit can include a primer pair for amplification by, e.g. PCR or an isothermal amplification method. In some cases, the primer pair can specifically hybridize to the oil palm genome and flank at least about 8, 10, 12, 15, 20, 25, 30, 40, 50, 60, 70, 80, 90, 100, 125, 150, 175, 200, 250, 300, 350, 400, 450, 500, 600, 700, 800, 1000, 1500, 2000, 2500, 3000, 5000, 7500, or 10000 or more continuous nucleotides at or near the VIR locus. The primer pair can specifically amplify one or more VIR alleles and not amplify one or more VIR alleles, or the primer pair can amplify all naturally occurring VIR alleles.

The kit can also include control polynucleotides as described herein. For example, the kit can include a polynucleotide containing wild-type VIR nucleic acid or a portion thereof (e.g., a nucleic acids that contains SEQ ID NO:1 or 3 or a portion thereof). As another example, the kit can include one or more polynucleotides containing mutant VIR nucleic acid or a portion thereof (e.g., one or more nucleic acids encoding SEQ ID NOS:7, 9, 11, 13, or 15, or portions thereof) The kit can also include any of the reagents, proteins, oligonucleotides, etc. described herein. For instance, the control polynucleotides can be identical to expected amplicons based on the amplification primers described above (e.g., spanning the target sequence including at least a portion of one or more of SEQ ID NOS:1, 7, 9, 11, 13, 15, or 17), and/or portions of such amplicons that would occur upon cleavage with the endonucleases as described above.

In some embodiments, a kit can include compositions for prediction of fruit color phenotype and shell thickness phenotype (e.g., *dura, pisifera*, and *tenera*). In some cases, the fruit color and shell thickness phenotypes can be predicted at the same time, e.g., as part of a single-pass sampling, identification, and/or sorting method. In some cases, the fruit color and shell thickness phenotypes can be predicted using the same nucleic acid sample. For example, a nucleic acid sample can be extracted from a portion of a plant or a seed and teated for the presence or absence of a *viriscens* allele or a polymorphism in linkage disequilibrium with a *virescens* or *nigrescens* allele and tested to predict the shell thickness phenotype of the plant or seed. Methods, compositions, and kits for predicting SHELL thickness include, but are not limited to, determining the genotype at the SHELL locus, determining the genotype of a polymorphism in linkage disequilibrium with the SHELL locus, determining the genotype of a gene that controls the shell thickness phenotype (e.g., a gene encoding a MADS box protein), or identifying the presence or absence of a polymorphism in linkage disequilibrium with a gene that controls the shell thickness phenotype. Methods, compositions and kits for predicting shell thickness are described, e.g., in PCT Publication No. 2013/142187; U.S. Patent Application No. 61/612,885, filed on Mar. 19, 2012; U.S. Patent Application No. 61/847,853 filed on Jul. 18, 2013; and U.S. Application No. 61/856,433, filed on Jul. 19, 2013, the contents of which are hereby incorporated by reference in their entirety for all purposes.

EXAMPLES

The following examples are offered to illustrate, but not to limit the claimed invention.

Example 1

Identification and Characterization of the Gene Controlling the Fruit Color Phenotype in Oil Palm Introduction Commercially grown oil palm (*Elaeis guineensis*) is an outbreeding diploid species (2n=32) of West African origin (Zeven, A. C. J. Niger. Inst. Oil Palm Res. 4, 218-225 (1965); Hartley, C. In: *The Oil Palm*. 47-94 (Longman, 1988); Singh, R. et al. Nature 500, 335-339 (2013)). We recently reported the genome sequences of *F. guineensis* and the South American oil palm, *E. oleifera* (Singh, R. et al. Nature 500, 335-339 (2013)), as well as the discovery of the oil palm SHELL gene, a homologue of SEEDSTICK (STK), responsible for oil palm fruit forms (Singh, R. et al. Nature 500, 340-344 (2013)). We next sought to identify the genetic basis of oil palm fruit colour.

Fruit colour is an important trait in terms of fruit harvesting and, therefore, oil yield. The majority of oil palms produce either *nigrescens* or *virescens* fruit type (Hartley, C. In: *The Oil Palm*. 47-94 (Longman, 1988)). *Nigrescens* fruits are usually deep violet to black at the apex and yellow at the base when unripe, with minimal change in colour upon ripening (FIG. 1*a, c*). *Virescens* fruits are green when unripe, and change to orange when the bunch matures (FIG. 1*b, c*). For *nigrescens* palms, harvesters rely on the presence of detached fruits on the ground to determine that bunches are ripe. However, as *virescens* fruits undergo a more profound colour change upon ripening, it is easier to identify ripe bunches, particularly in tall palms where they can be obscured by fronds, thus minimizing yield loss due to fallen fruits or harvesting of unripe bunches. Both *nigrescens* and *virescens* palms occur in natural groves. Although the *virescens* trait is dominant, the number of *virescens* palms found in natural populations is small, with frequencies ranging from below 1% in Nigeria and Angola (Hartley, C. In: *The Oil Palm*. 47-94 (Longman, 1988)) to up to 50% in one location in Congo (Rajanaidu, N. In: *Proc. Int. Workshop. "Oil palm germplasm and utilization". Palm Oil Res. Inst. Malaysia*, 59-83 (1986)). *Virescens* palms were used in ancient ceremonial rites (Zeven, A. C. J. Niger. Inst. Oil Palm Res. 4, 218-225 (1965)), explaining their occurrence among wild-type *nigrescens* palms, and "Ojuku" plants matching the description of *virescens* palms were reportedly used in tribal sacrificial ceremonies in West Africa (ANON. Bulletin of Miscellaneous Information, Royal Botanic Gardens, Kew, 33-49 (1909); Farquhar, J. H. J. In: *The oil palm and its varieties*. 1-11 (Whitehall Gardens, S. W., 1913)).

Methods

Plant Materials and Germplasm Collection

The mapping family used was derived from the self pollination of a high iodine value *virescens tenera* palm T128 (accession number MPOB 371) which has been described in detail in Singh, R. et al. Nature 500, 340-344 (2013). An additional 108 palms derived from six families of different genetic backgrounds (Table 1) were available, part of which (81 palms) were used to confirm marker-trait association, while 96 of these palms were used to sequence the entire *virescens* gene. Similarly, an additional collection of advanced breeding lines (AVROS) (43 *nigrescens*) and germplasm material (87 *virescens* and 353 *nigrescens*) collected from seven countries in Africa were also sequenced to confirm the identity of the *virescens* gene and identify additional mutations within VIR. All germplasm materials were collected under bilateral agreements with the respective countries and followed closely the Convention on Biological Diversity (1992). The processing of leaf samples and DNA extraction were carried out as previously described in Singh, R. et al. Nature 5(00, 340-344 (2013).

Genetic Mapping

A total of 240 palms of the mapping family were available for DNA extraction at the start of this study. Of these, 32 palms could not be phenotyped with confidence, as the palms had been cut down or succumbed to disease before the fruit exocarp colour could be determined or re-confirmed. Of the 208 palms that were successfully phenotyped, 160 were identified as *virescens* palms and 48 as *nigrescens* palms. However, all 240 available palms were genotyped with 4,451 SNP markers using the Illumina iSelect assay (Illumina), 3 RFLP and 197 SSR markers. The genetic map was constructed essentially as described in Singh, R. et al. *Nature* 500, 340-344 (2013), using JoinMap4.0.

Forward and reverse primers included M13 Forward or M13 Reverse sequence tags, respectively. Amplicons were treated with exonuclease 1 (New England Biolabs) and shrimp alkaline phosphatase (Affymetrix) under standard conditions. Amplicons were sequenced using a combination of M13 primers and internal primers (internal primer sequences available upon request). Sequencing was performed on an ABI 3730 capillary DNA sequencer using big dye terminator VS 3.1 chemistry (LIFE Technologies). Local assemblies of each amplicon were constructed with PHRAP and reviewed

TABLE 1

| No. | Cross Type | Trial No. | Location | No. Palms Tested | Genetic Background |
|---|---|---|---|---|---|
| 1 | Tenera (T) × Tenera (T) | MKPOB PK575 | MPOB-UKM Station, Bangi, Selangor | 21 | [0.151/128] × [AAR 0.127/13] |
| 2 | Tenera (T) × Tenera (T) | TT132 | United Plantations, Teluk Intan, Perak | 12 | [Yangambi] × [Jenderata TT-Yocoboue] |
| 3 | Tenera (T) × Tenera (T) | TT108 | United Plantations, Teluk Intan, Perak | 12 | [Jenderata TT-Yocoboue] × [Nigerian Tenera] |
| 4 | Dura (D) × Tenera (T) | DT35 | United Plantations, Teluk Intan, Perak | 22 | [Ulu-Bernam-Klanang Baru Deli Dura] × [Nigerian Tenera] |
| 5 | Dura (D) × Tenera (T) | DT38 | United Plantations, Teluk Intan, Perak | 20 | [Klanang Baru-Ulu Remis Deli Dura] × [Nigerian Tenera] |
| 6 | Dura (D) × Pisifera (P) | DP454 | United Plantations, Teluk Intan, Perak | 21 | [Ulu Remis Deli Dura] × [Yangambi Nifor] |

[1]Parenthesis preceding the symbol 'x' denotes the female parent..
[2]In the populations listed above, the female parent of MPOB PK575 is palm T128, which was self-pollinated to generate the population used for map construction in this study.
[3]The family TT132 was used to verify marker-trait linkage, but not used to amplify the virescens gene for confirmation via sequencing.

Fruit Colour Phenotyping

The fruit exocarp colour was determined on ripe bunches, following the ripeness criteria described in Corley and Tinker. In: *The Oil Palm* 4th edn, 287-325 (Blackwell Science, 2003), at least one loose fruit per bunch (irrespective of plant height). The bunch was harvested from the plant and a minimum of five fruitlets were stripped from the bunch. Visual observation was made of the exocarp, and fruits were classified as *nigrescens* (black at upper half and red at bottom) or *virescens* (orange with a greenish top). In this study at least two independent attempts were made to determine fruit colour of the mapping family as well as the breeding populations. With respect to the germplasm collection, fruit colour observations were made only once.

Genome and Transcriptome Sequencing

Twelve independent T128 progeny palms (5 *nigrescens* and 7 *virescens*) were sequenced to 20× raw sequence coverage by HISEQ 2000 (Illumina). Library construction, sequencing and assemblies were performed as described in Singh, R. et al. *Nature* 500, 335-339 (2013). For transcriptome sequencing, RNA was extracted from 10-20 fruits from two plants (1 *nigrescens* and 1 *virescens*) at 8 WAA. Three replicate RNA extractions were performed for each fruit pool. TrueSeq (Illumina) libraries were constructed and sequenced by HISEQ 2000 as described in Singh, R. et al. *Nature* 500, 340-344 (2013).

VIR Sanger Sequencing

The entirety of the VIR gene was amplified by PCR from oil palm genomic DNA using forward primer sequence, (SEQ ID NO:18) GCGTACGTGGAACCACAA, and reverse primer sequence, (SEQ ID NO:19) CTCCATCCTGGTGAGAAAGCGT, generating a single ~2.9 Kb amplicon.

in CONSED. Consensus sequence for each palm was aligned to the reference *pisifera* genome sequence (Singh, R. et al. *Nature* 500, 335-339 (2013)). Data were analyzed to determine the integrity of the coding sequence and resulting putative translated polypeptide of the PAP1-like gene for each palm. A large percentage of the palms analyzed were part of the 110,000 diverse germplasm collection available at MPOB.

Phylogenetic Analysis

A collection of R2R3 MYBs from previously studied plant species were selected based on their similarity to the VIR protein. These sequences were aligned using the ClustalX program, and the highly conserved R2R3 domains were then processed using the promlk program from the phylip package.

Pigment Extraction and Spectrophotometric Analysis

Acidified methanol (1% HCl, v/v) was added to ground exocarp slices of *E. guineensis* (15 WAA *nigrescens* and *virescens* fruits) and stirred to ensure efficient extraction of pigments. The extracts were centrifuged at 3,000×g in an Eppendorf 5810R centrifuge to remove debris. The supernatants were removed and filtered prior to further analysis. UV-Visible absorption spectra were recorded from 230-780 nm at 10 nm intervals using a U-2800 double beam scanning UV-Visible spectrophotometer (Hitachi, Japan) to determine the presence, if any, of anthocyanins.

High Performance Liquid Chromatography (HPLC)

HPLC was performed on a Waters 250× 4.6 mm i.d., 5 μm, Atlantis dC18 column using a Waters Alliance W 2695 Separation Module (Waters. Assoc., Milford, USA) equipped with a 2996 photodiode array detector. A gradient mobile phase comprising Solvent (A), 9% acetonitrile, 10% formic acid, 90% water (v/v/v) and Solvent (B) 36% acetonitrile, 10% formic acid, 54% water (v/v/v) was used. The elution gradient was 0-3 min, 100% A., 3-30 min 71.5% A., 28.5% B., 30-45 min, 71.5% A., 28.5% B. The flow rate was 1.0 mL per min and injection volume was 20 μL. Absorbance spectra were collected for all peaks.

Results

Oil palm is an out-breeding species, and as such, a high degree of heterozygosity is expected. A population of 240 palms derived from the self-pollination of the *tenera* palm, T128 (0.151/128×0.151/128), from Malaysian Palm Oil Board's (MPOB) Nigerian germplasm collection (Rajanaidu, N. In: Proceedings of the 12th Plenary Meeting of Association for the Taxonomic Study of the flora of tropical Africa (AETFAT), Mitteilingen Inst. Allg. Bot. Hamburg, Germany, pp 39-52 (1990); Cheah. S. et al. In: Proceedings of the 1999 PORIM International Palm Oil Conference (eds Darus, K., Chan, K. W and Sharithh, S. R. S. A) Palm Oil Research Institute of Malaysia, pp 297-320 (1999); Singh, R. et al. *Asia Pac. J. Mol. Biol. Biotechnol.* 16, 53-63 (2008)) was used to generate a genetic linkage map (Singh, R. et al. *Nature* 500, 335-339 (2013); Singh, R. et al. *Nature* 500, 340-344 (2013)). In addition, a subset of 81 palms from six independent crosses (Table 1) was used to confirm marker linkage. Markers were scored as co-dominant, segregating in a 1:2:1 ratio in most cases, while the *virescens* phenotype also showed the expected 3:1 segregation ratio in the mapping population (Table 2).

TABLE 2

Analysis of palms for fruit-colour

| Number of palms genotyped# | Expected Ratio | | Observed Numbers | | | |
|---|---|---|---|---|---|---|
| | *Nigrescens* | *Virescens* | *Nigrescens* | *Virescens* | Total# | $\chi^2$ |
| 240 | 1 | 3 | 48 | 160 | 208 | 0.41 |

There was a discrepancy between the total number of palms genotyped and the number observed for fruit-colour because some of the palms could not be phenotyped for various reasons.

Figure 2:
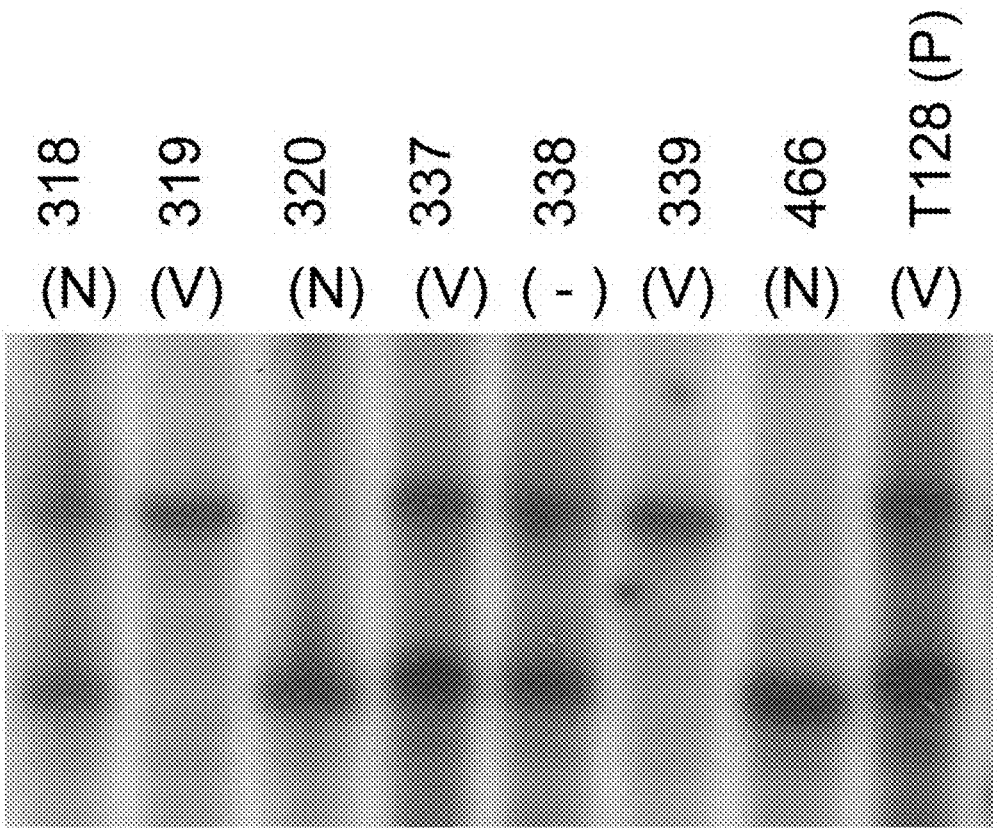
FIG. 2: Segregation of the RFLP marker, MET16, compared to that of the fruit color gene in the mapping population. DNA from a subset of the mapping population was digested with BamHI and analyzed by Southern blotting with the MET16 probe. The majority of the *virescens* fruit (93%) matched with the homozygous (top segregating band present) or heterozygous (both the segregating bands present) profile of the probe. At the same time, a very large proportion of the *nigrescens* fruits showed a profile consistent with only the bottom segregating band being present (homozygous for the wild type allele). N, *nigrescens* fruits. V, *virescens* fruits. Palm identification numbers are indicated above. Symbol "–" indicates a palm for which fruit colour could not be determined in the field.

Three informative RFLP markers were genotyped on the entire mapping population, and 197 SSR loci that were polymorphic in the mapping population were identified. Of 4,451 SNPs screened, 711 were used in map construction. The locus for the *virescens* gene (VIR) was located on linkage group 1 (Chromosome 1), with the RFLP marker MET 16 being the most tightly linked (Tables 3 and 4, FIG. 2).

TABLE 3

Linkage of SNP markers to the VIR gene locus in the mapping family and to Scaffolds in the Reference Genome Sequence

| Marker | No. of Palms with Genotype and Phenotype | No. of Palms Matching Expected Profile | No. of Recombinants | % Predictability | Scaffold |
|---|---|---|---|---|---|
| SNPM01649y | 205 | 146 | 59 | 71% | sc00408 |
| SNPM04083x | 207 | 162 | 45 | 78% | sc01152 |
| SNPM02176x | 207 | 166 | 41 | 80% | sc00231 |
| SNPM03563x | 207 | 164 | 43 | 79% | sc00015 |
| SNPM00066x | 206 | 175 | 31 | 85% | sc00015 |
| SNPM00257_1y | 208 | 177 | 31 | 85% | co228588 |
| SNPM02655y | 207 | 183 | 24 | 88% | sc00125 |
| SNPM00387x | 206 | 185 | 21 | 90% | sc00007 |
| SNPM04941x | 206 | 191 | 15 | 93% | sc00007 |
| SNPM00572y | 205 | 190 | 15 | 93% | sc00007 |
| SNPM02867y | 206 | 192 | 14 | 93% | sc00007 |
| SNPM02708y | 206 | 192 | 14 | 93% | sc00007 |
| SNPM03010y | 206 | 196 | 10 | 95% | sc00007 |
| SNPM01250x | 206 | 197 | 10 | 95% | sc00007 |
| SNPM01237x | 207 | 197 | 10 | 95% | sc00007 |
| MET16x | 200 | 191 | 9 | 96% | sc00007 |
| VIR | | | | | |
| sOleiSc00009x | 204 | 193 | 11 | 95% | sc00007 |
| sMg00228x | 205 | 193 | 12 | 94% | sc00327 |
| SNPM00383x | 204 | 190 | 14 | 93% | sc00327 |
| SNPM02400x | 202 | 189 | 13 | 94% | sc00942 |
| SNPM04251x | 207 | 187 | 20 | 90% | sc00031 |
| SNPM00013y | 208 | 186 | 22 | 89% | sc00031 |
| SNPM00012y | 208 | 186 | 22 | 89% | sc00031 |
| sEg00164x | 204 | 179 | 25 | 88% | sc00031 |
| SNPM04365y | 207 | 179 | 28 | 86% | sc00031 |
| SNPM04665y | 206 | 178 | 28 | 86% | sc00102 |

TABLE 3-continued

Linkage of SNP markers to the VIR gene locus in the mapping family and to Scaffolds in the Reference Genome Sequence

| Marker | No. of Palms with Genotype and Phenotype | No. of Palms Matching Expected Profile | No. of Recombinants | % Predictability | Scaffold |
|---|---|---|---|---|---|
| SNPM04690x | 207 | 175 | 32 | 85% | sc00102 |
| SNPM00498x | 206 | 167 | 39 | 81% | sc00093 |
| SNPM01470x | 206 | 164 | 42 | 80% | sc00144 |
| SNPM04247x | 205 | 160 | 45 | 78% | sc00101 |
| SNPM01475y | 205 | 156 | 49 | 76% | sc00101 |
| SNPM00224y | 207 | 156 | 51 | 75% | co413678 |
| SNPM04284x | 206 | 149 | 57 | 72% | sc19981 |
| SNPM02318x | 205 | 148 | 57 | 72% | sc00069 |
| SNPM00461y | 206 | 147 | 59 | 71% | sc00069 |
| SNPM02596x | 206 | 149 | 57 | 72% | sc00363 |
| SNPM00197_1y | 208 | 145 | 63 | 70% | sc00069 |
| SNPM04508x | 206 | 141 | 65 | 68% | sc00019 |
| SNPM01129y | 205 | 138 | 67 | 67% | sc00019 |
| SNPM03276y | 205 | 136 | 69 | 66% | sc00019 |
| SNPM00368y | 208 | 131 | 77 | 63% | sc00080 |
| SNPM00340x | 202 | 135 | 67 | 67% | sc00080 |

TABLE 4

Correlation of *virescens* and *nigrescens* palms with the banding profile for probe MET16 in a subset of the T128 mapping population

| No. of palms with field data | V (1) | V — N (2) | N (3) | $\chi^2$ | No. of palms with fruit-colour-not matching banding patterns Vir | Nig |
|---|---|---|---|---|---|---|
| 125 | 28 | 62 | 21 | 2.40 | 1 | 4 |

*No. of palms for which the RFLP profile was not clear/missing data: 9

Linkage of MET16 to the *virescens* trait was further tested in the 81 plants, resulting in 95% accuracy for distinguishing between *nigrescens* and *virescens* fruit traits (Table 5).

TABLE 5

Linkage of RFLP marker MET16 to the fruit-colour locus in six different families

| Probe | Trait | No. of Palms Tested | No of Palms matching expected profiles | No. of Recombinants |
|---|---|---|---|---|
| MET16 | Fruit-colour (vir) | 81 | 77 | 4 |

Figure 3:
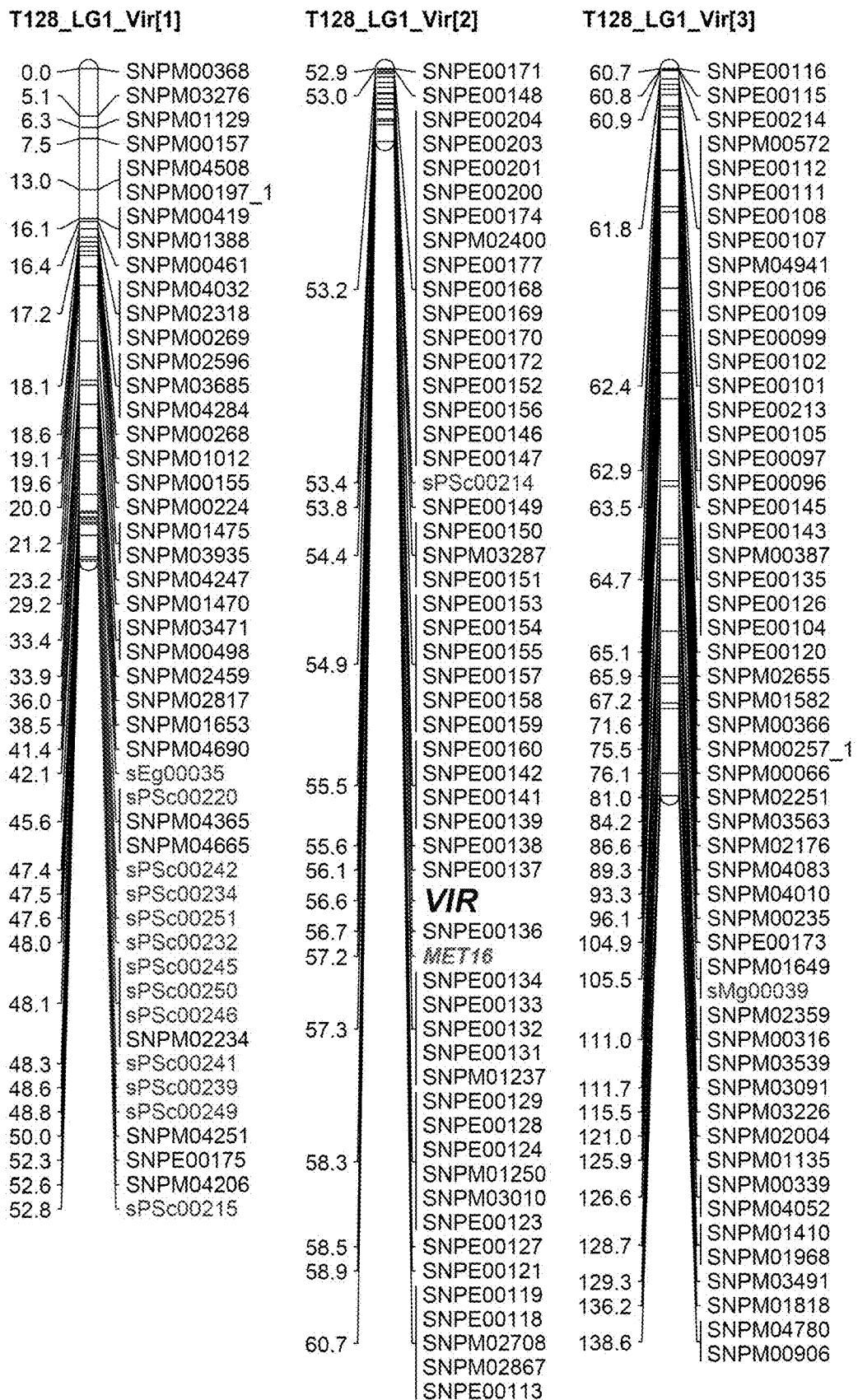
FIG. 3: Linkage group 1 of the genetic linkage map of the VIR locus. The VIR locus is shown as "VIR," SNP markers are designated "SNPM#," where "#" denotes a number, the RFLP marker is designated "MET16," and the simple sequence repeat (SSR) markers are designated with a lower case "s" followed by "Eg," "PSc," or "Mg," followed by a number.

Markers flanking the VIR candidate locus were mapped by sequence similarity to the *E. guineensis* (*pisifera*) reference genome assembly and localized to assembly scaffold 7 (p3-sc00007). A tiling path of BAC contigs corresponding to scaffold 7 was selected from a high-information content physical map of *pisifera* and sequenced. Additional SNP assays were designed from an improved assembly corresponding to scaffold 7 and genotyped. Markers mapping close to the VIR locus were identified (FIG. 3) and markers SNPM02708 and SNPM02400 were positioned on each side of the VIR locus. The interval contained 4 potential candidate genes that impact fruit pigmentation in other species: a gene with significant homology to both *Arabidopsis* PRODUCTION OF ANTHOCYANIN PIGMENT 1 (PAP1) and AtMYB113, and homologues of *Arabidopsis* TRANSPARENT TESTA 12 (7TI2), PURPLE ACID PHOSPHA TASE 18 (PAP18) and the BHLH gene, ILR3.

Figure 4:
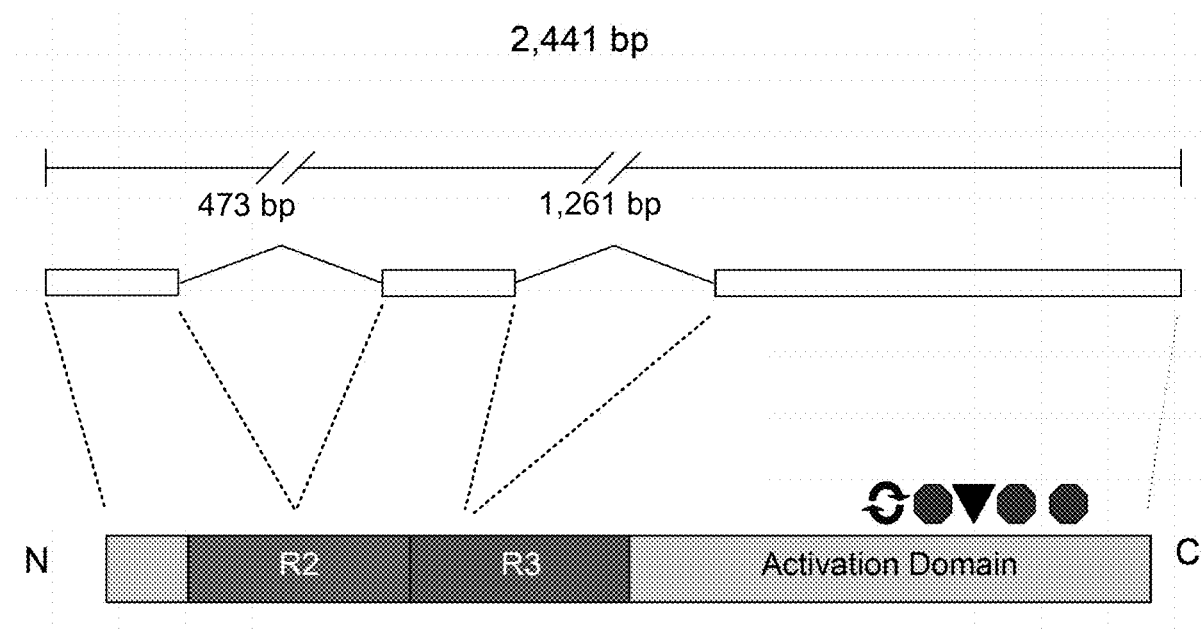
FIG. 4: Structure of the VIR gene and diagram of the five mutation events accounting for the *virescens* fruit colour phenotype. The 2,441 bp VIR gene codes for a 236 amino acid homolog of OsMYB113, which is an R2R3 class transcription factor. The R2 and R3 domains are intact in both wild type and sequenced mutants. However, the five observed mutations in sequenced *virescens* palms each caused a truncation in the activation domain of the protein. The relative locations of early stop codons (octagon), frame shift introducing deletions (triangle) and rearrangement with small duplication (arrow loop) are shown.
Figure 6:
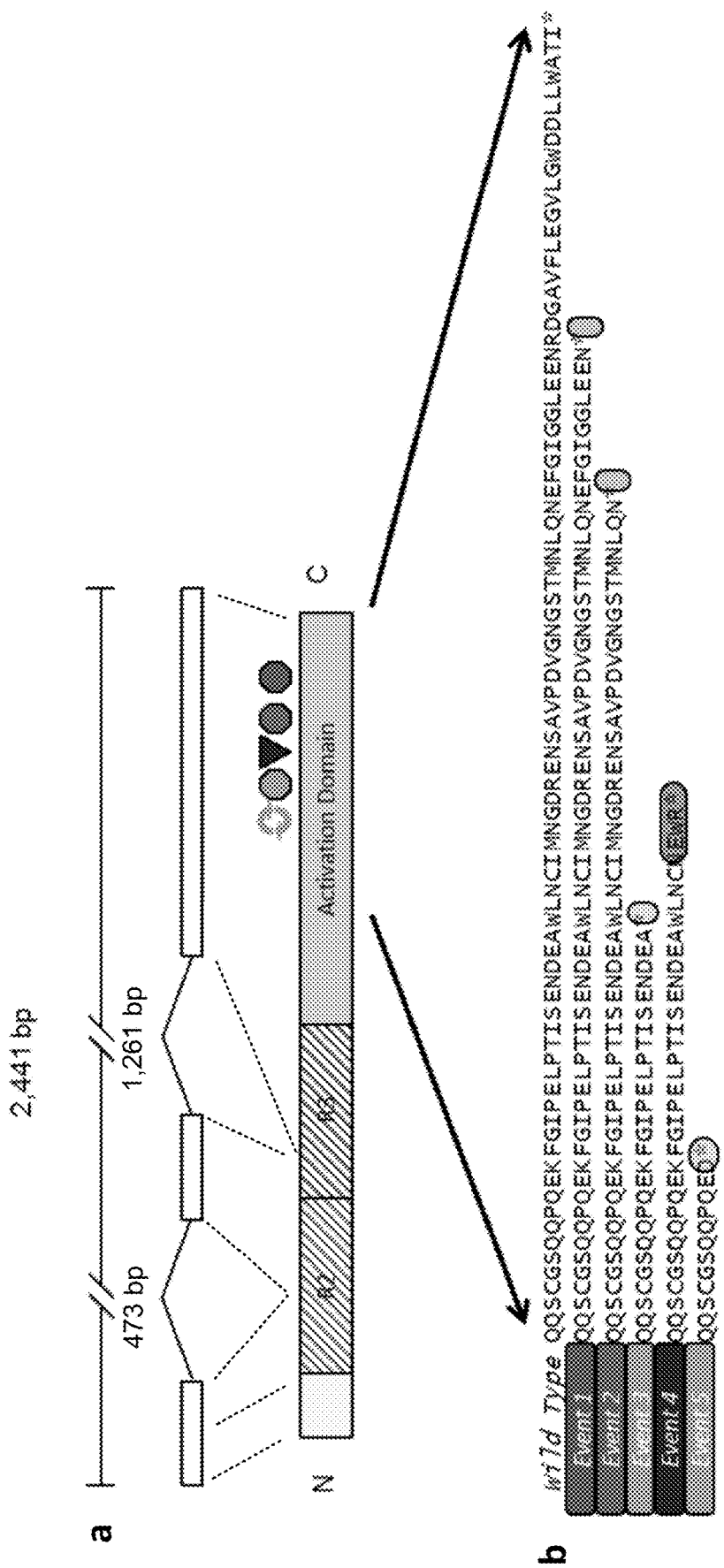
FIG. 6: Five independent VIR mutations account for *virescens* fruit exocarp colour phenotype. a, Diagram of the VIR gene. The 2.4 Kb locus (top line) includes three exons (open boxes) encoding the regions of the R2R3-MYB protein, as indicated by dashed lines. The protein (bottom diagram) includes two helix-loop-helix motifs, R2 and R3, followed by a transcriptional activation domain (grey box). Symbols above the activation domain represent relative positions of the Event 1-5 mutations. Symbol colours indicate the specific mutational event as shown in panel b. b, Protein sequence of the carboxy-terminal region of VIR encoded by wild-type (SEQ ID NO:26) and mutant VIR alleles. Nonsense point mutations (Events 1-3; SEQ ID) NOS:27-29), a two bp frameshift deletion (Event 4: SEQ ID NO:30) and a rearrangement (Event 5; SEQ ID NO:31) each results in premature termination of the activation domain at the indicated amino acid position. DNA sequences and details of the Event 5 rearrangement are provided in FIGS. 4 and 5.

Identification of the VIR Gene and Mutations Responsible for *Virescens* Fruit Colour To extend beyond the *E. guineensis* reference genome sequence, we queried genome sequence assemblies of 12 independent T128 progeny palms (5 *nigrescens* and 7 *virescens*) derived from 20-fold raw sequence coverage (HISEQ2000) per genome. Contigs from each assembly were mapped to the scaffolds which had been linked to genetic markers in the *virescens* genetic interval. In addition, the candidate genes above were each amplified by PCR, including exons and introns, and sequenced (AB13730). The entire open reading frame of the gene homologous to PAP1 and AtMYB113 was intact in all 5 *nigrescens* palms. However, all 7 *virescens* palms were either heterozygous (n=4) or homozygous (n=3) for an A-to-T nonsense mutation in exon 3 of the identified candidate VIR gene (FIGS. 4 and 5). The exon 3 mutation results in a predicted truncation of the 21 carboxy-terminal amino acids within the transcriptional activation domain of the R2R3-MYB transcription factor (FIG. 6).

Subsequently, the entirety of the gene was amplified and sequenced in 208 plants from the T128 cross (48 *nigrescens* and 160 *virescens*). In all, 158 plants were either heterozygous (n=99) or homozygous (n=0.59) for the nonsense mutation in exon 3, and 50 plants were homozygous wild-type, for an overall concordance of this nonsense mutation (Event 1) with fruit colour phenotype of 99% (Table 6). It is noted that a 1% discordance rate is well within the norms of phenotyping accuracy of breeding populations (Singh, R. et al. *Nature* 500, 340-344 (2013)). Although SNPs were identified in the other three candidate genes, the polymorphisms observed were not consistent with a functional mechanism affecting fruit colour phenotype of the twelve plants, and independent mutant alleles (see below) were not identified.

TABLE 6

Summary of VIR genotypes

| | Phenotype | | | Genotype | | | | | | Gen/Phen |
|---|---|---|---|---|---|---|---|---|---|---|
| | Nig[a] | Vir[b] | Total | Nig[c] | Event 1 | Event 2 | Event 3 | Event 4 | Event 5 | Concordance[d] |
| Mapping population | | | | | | | | | | |
| T128 | 48 | 160 | 208 | 50 | 158 | — | — | — | — | 99.0% |
| Breeding Populations | | | | | | | | | | |
| DT35 | 11 | 11 | 22 | 11 | 11 | — | — | — | — | 100.0% |
| DT38 | 8 | 12 | 20 | 8 | 12 | — | — | — | — | 100.0% |
| DP454 | 9 | 12 | 21 | 9 | 12 | — | — | — | — | 100.0% |
| TT108 | 6 | 6 | 12 | 6 | 6 | — | — | — | — | 100.0% |
| AVROS | 43 | — | 43 | 43 | — | — | — | — | — | 100.0% |
| MPOB PK575 | 10 | 11 | 21 | 10 | 11 | — | — | — | — | 100.0% |
| Total | 87 | 52 | 139 | 87 | 52 | 0 | 0 | 0 | 0 | 100.0% |
| Germplasm Collections | | | | | | | | | | |
| Angola | 261 | 48 | 309 | 262 | — | 45 | 1 | 1 | — | 99.7% |
| Madagascar | 27 | — | 27 | 27 | — | — | — | — | — | 100.0% |
| Tanzania | 47 | 12 | 59 | 45 | — | 14 | — | — | — | 96.6% |
| Ghana | 8 | 15 | 23 | 8 | 3 | 4 | 8 | — | — | 100.0% |
| Congo | 3 | 7 | 10 | 2 | — | 5 | 1 | 2 | — | 90.0% |
| Cameroon | 5 | 3 | 8 | 5 | — | — | — | — | 3 | 100.0% |
| Nigeria | 2 | 2 | 4 | 2 | 2 | — | — | — | — | 100.0% |
| Total | 353 | 87 | 440 | 351 | 5 | 68 | 10 | 3 | 3 | 99.1% |
| Overall Total | 488 | 299 | 787 | 488 | 215 | 68 | 10 | 3 | 3 | 99.2% |

[a]Nigrescens fruit exocarp colour phenotype
[b]Virescens fruit exocarp colour phenotype
[c]Wild-type (nigrescens) genotype
[d]Genotype/Phenotype Concordance calculated as ((Number of virescens phenotyped plants genotyped as either heterozygous or homozygous for Event 1, 2, 3, 4, or 5) + (Number of nigrescens phenotyped plants genotyped as wild-type)) divided by the total number of plants sequenced.

To further support the discovery of the VIR gene, we sequenced the entire gene in 6 independent breeding populations, as well as samples from germplasm collections (Table 6). The breeding populations included 139 plants where the fruit colour phenotype was known (DT35, DT38, DP454, TT108, MPOBPK575 and a collection of palms from the AVROS background). In addition, 440 plants from Angola, Madagascar, Tanzania, Ghana, Congo, Cameroon and Nigeria were analyzed. In the breeding populations, all 52 virescens, but none of the 87 nigrescens plants were found to be either heterozygous or homozygous for the Event 1 nonsense mutation in exon 3 (Table 6).

Figure 7:
FIG. 7: Geographic sources of VIR mutant alleles. Palms were genotyped by sequencing to identify homozygosity or heterozygosity for each of the five identified VIR mutations (Events 1-5). The location(s) of palms harbouring each of the mutation events in Africa is shown.

However, among the germplasm collections, the Event 1 mutation was detected in only 5 of 87 virescens plants, all of which were from either the Ghana or Nigeria collections. Instead, four independent, but closely related, mutations were identified in the other germplasm collections from sub-Saharan Africa. First, a G-to-T nonsense mutation (Event 2) was detected in exon 3, 30 base pairs (bp) 5' to Event 1 (FIGS. 4-6). This mutation results in a predicted truncation of the 31 carboxy-terminal amino acids within the transcriptional activation domain. Event 2 was heterozygous or homozygous in 68 plants from the Angola (n=45), Tanzania (n=14), Ghana (n=4) or Congo (n=5) collections (Table 6, FIG. 7). Next, a G-to-A nonsense mutation (Event 3) was detected in exon 3, 113 bp 5' to Event 1 (FIGS. 4-6). This mutation results in a predicted truncation of the 59 carboxy-terminal amino acids. The Event 3 mutation was heterozygous in 10 plants from Angola (n=1), Ghana (n=8) or Congo (n=1) (Table 6, FIG. 7). A fourth mutation (Event 4) is a two bp deletion beginning 11 bp 3' to Event 3, resulting in translation frameshift at the 55th carboxy-terminal amino acid (FIGS. 4-6), and was heterozygous in 3 plants from Angola and Congo (Table 6, FIG. 7).

Finally, a heterozygous rearrangement (Event 5) resulting in a translational frameshift and premature truncation was detected in 3 of 3 virescens plants from Cameroon (Table 6, FIGS. 4-7). The mutation is a 195 bp deletion with a 21 bp duplication which results in the truncation of 75 carboxy-terminal amino acids and a single amino acid conversion before reading a new stop codon. Considering all five single gene mutations, the concordance between genotype and fruit colour is 99.2% (Table 6).

The identification of 5 independent genetic mutations, each resulting in remarkably similar premature truncation within the activation domain, provides strong evidence for the identification of the VIR gene. C-terminal truncations of related genes in the R2R3-Myb family, most notably the maize C1 gene, have similarly dominant negative allelic forms (McClintock, B. Cold Spring Harb. Symp. Quant. Biol. 16, 13-47 (1951)). Furthermore, sequence similarity searches (BLAST™) of the genome of the South American oil palm, E. oleifera (Singh, R. et al. Nature 500, 335-339 (2013)), which does not produce the deep violet coloured fruits similar to wild-type E. guineensis, do not identify an intact VIR gene.

Phylogeny, Expression and Function of VIR

The R2R3-MYB family includes more than 100 genes in Arabidopsis (Kranz, H. D. et al. Plant J. 16, 263-276 (1998); Romero, I. et al. Plant J. 14, 273-284 (1998)) and more than 80 genes in maize (Rabinowicz, P. D. et al. Genetics 153, 427-444 (1999)). The family includes two sets of imperfect repeats (R2 and R3), each including three alpha-helices forming a helix-turn-helix motif (Du, H. et al. Biochemistry 74, 1-1 (2009)). The R2R3 proteins are members of regulatory networks controlling development, metabolism and responses to biotic and abiotic stresses (Dubos, C. et al.

Figure 8:
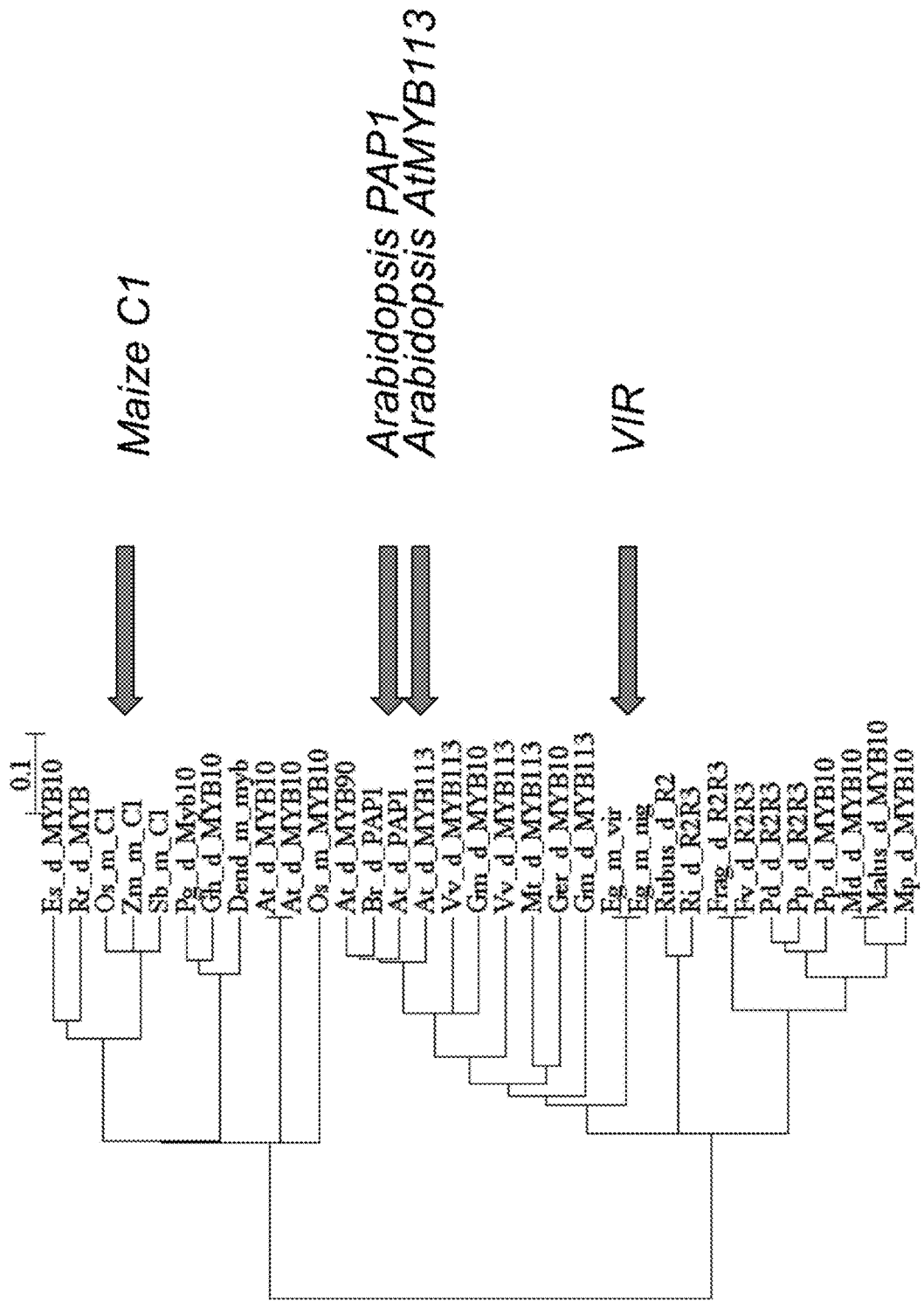
FIG. 8: Phylogenetic analysis of VIR and various R2R3-MYB family members. Species abbreviations are *Arabidopsis thaliana* (At), *Zea mays* (Zm), *Sorghum bicolor* (Sb), *Oryza saliva* (Os), *Epimedium sagiatum* (Es), *Rosa rugosa* (Rr), *Rubus idaeus* (Ri), *Rubus* hybrid (*Rubus*), *Prunus persica* (Pp). *Prunus dulcis* (Pd). *Malus×domestica* (Md), *Malus* hybrid (*Malus*), *Malus pumila* (Mp), *Fragaria×ananassa* (Frag), *Fragaria vesca* (Fv), *Gerbera hybrida* (Ger), *Medicago truncatula* (Mt), *Vitis vinifera* (Vv), *Brassica rapa* (Br), *Glycine max* (Gm), *Elaeis guineensis* (Eg), *Picea glauca* (Pg), *Dendrobium* sp. XMW-2002-10 (Dend), and *Gossypium hirsutum* (Gh). Monocots and dicots are designated with "in" and "d" respectively.
Figure 9:
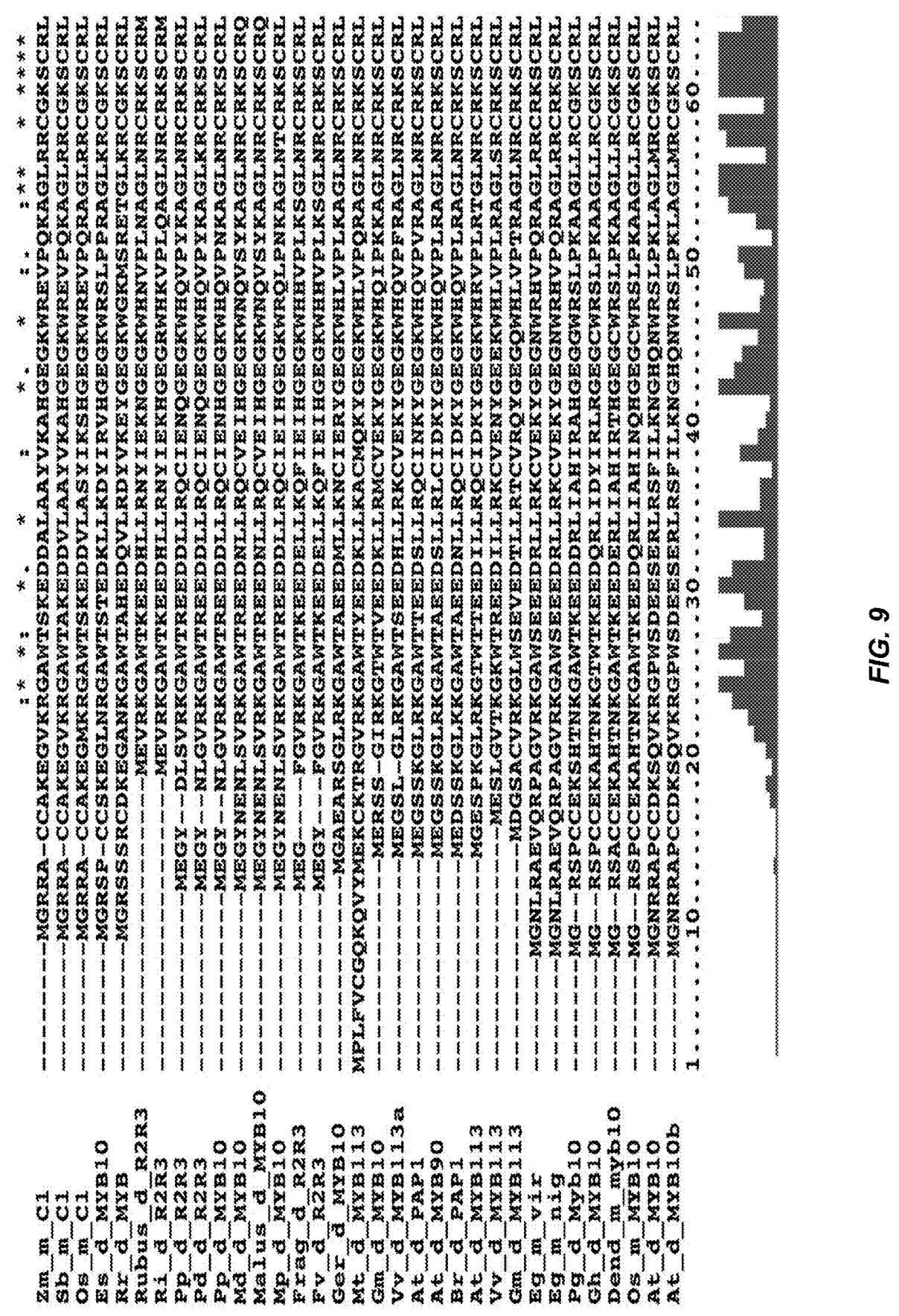
Figure 9:
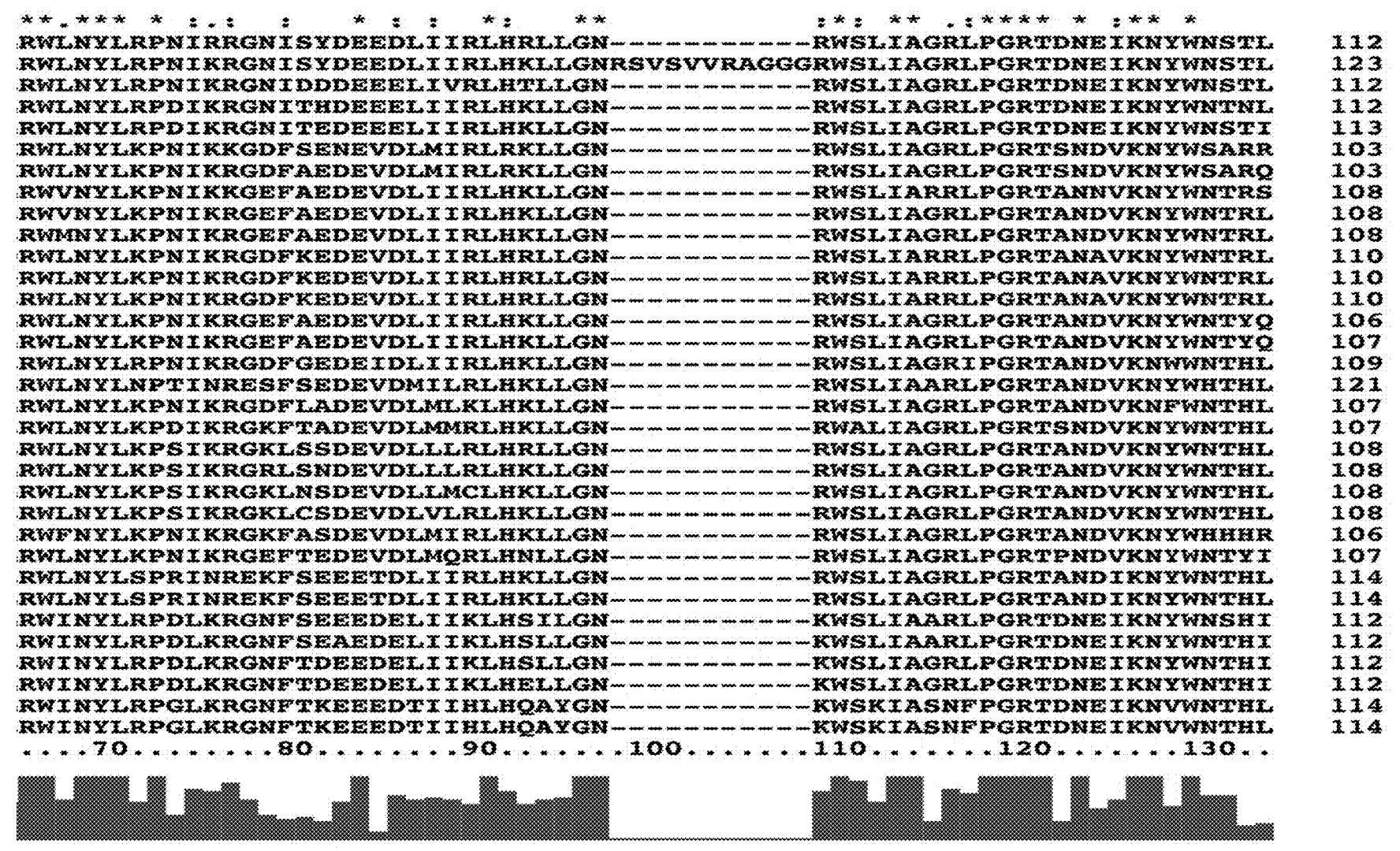

Trends Plant Sci. 15, 573-581 (2010)). We performed a phylogenetic analysis of the R2R3-MYB domain of VIR relative to other family members from various plant species, and the resulting phylogenetic tree suggests that it is related to MYB113/PAP1 (FIGS. 8, and 9). PAP1 and AtMYBI 13 belong to the phylogenetic branch of R2R3 proteins controlling accumulation of anthocyanins by regulation of biosynthetic gene expression (Borevitz, J. O. et al. *The Plant Cell* 12, 2383-2394 (2000); Gonzales, A. et al. *Plant. J.* 53, 814-827 (2008)). Overexpression of *Arabidopsis* PAP1 results in intense purple pigmentation in many vegetative organs throughout development, and ectopic expression of *Arabidopsis* PAP1 in tobacco results in purple pigmented plants (Borevitz, J. O. et al. *The Plant Cell* 12, 2383-2394 (2000)). Overexpression of AtMYB113 in *Arabidopsis* results in elevated pigment production, and down-regulation of AIMYB113, AtMYB114, PAP1 and PAP2 results in anthocyanin deficiency (Gonzales, A. et al. *Plant J.* 53, 814-827 (2008)). Furthermore, similar to the VIR mutations reported here, frameshift mutations in the carboxy-terminal region of C1 generates a dominant-negative inhibitory protein in maize, C1-1 (Goff, S. A. et al. *Genes Dev.* 5, 298-309 (1991)). Ectopic expression of another allele of maize C1-I that lacks only four carboxy-terminal amino acids (c1-1-2K1) results in severe reduction of pigmentation in tobacco (Chen, B. et al. *Mol. Biotechnol.* 26, 187-192 (2004)). Finally, overexpression of *Arabidopsis* Mv1114 lacking the transactivation domain results in dominant anthocyanin deficiency (Gonzales, A. et al. Plant J. 53, 814-827 (2008)).

Figure 10A:
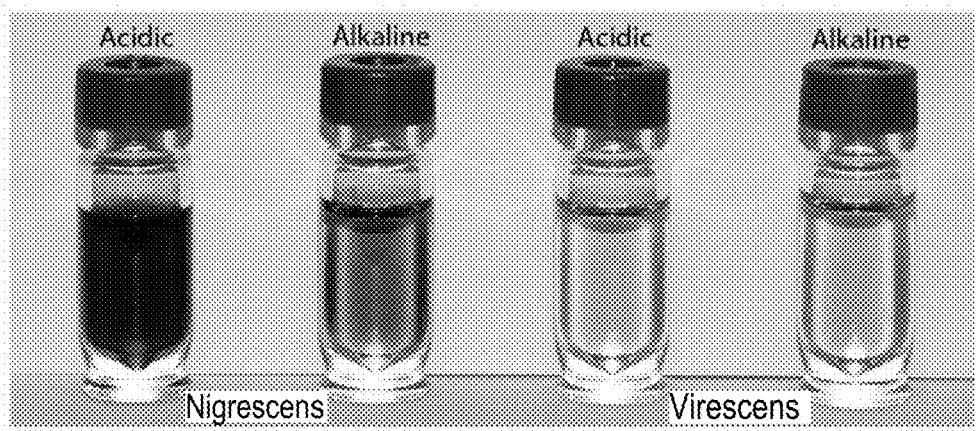
FIG. 10: Anthocyanin profiles in the *virescens* and *nigrescens* exocarp. a, Exocarp extracts in acidic and alkaline conditions. The *nigrescens* extract was brilliant red in acid and turned green under alkaline conditions. The *virescens* extract, however, was light orange and did not change under alkaline conditions. b, UV-VIS spectrophotometric profile of the extracts at pH 1. *Nigrescens* exhibited a maximum absorbance peak at about 520 nm. This peak was not observed in *virescens*. Anthocyanins are known to absorb strongly around this wavelength. c, HPLC profile at 520 nm. The *nigrescens* extract had at least 3 major anthocyanin peaks at 520 nm, which were absent in *virescens*. d, Transcriptome analyses of *nigrescens* and *virescens* whole fruit at 8 WAA. The average expression measured as $\log_{10}$ fragments per thousand mapped (FPKM) for all transcript reads matching each gene in the anthocyanin phenylpropanoid pathway was calculated, and the values obtained from *virescens* fruits was subtracted from those obtained from *nigrescens* fruits. Gene groups are plotted in pathway order, suggesting that *virescens* fruits display impaired Myb/bHLH/WD-repeat regulated gene expression beginning at the CHS step of the pathway.
Figure 10B:
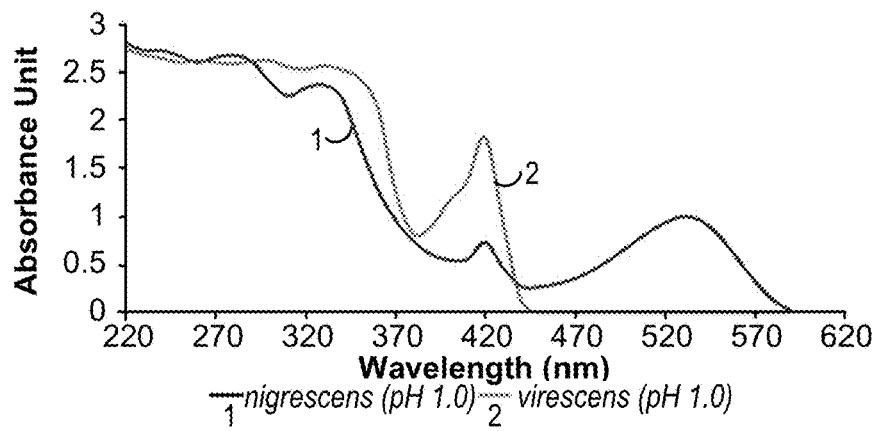
Figure 10C:
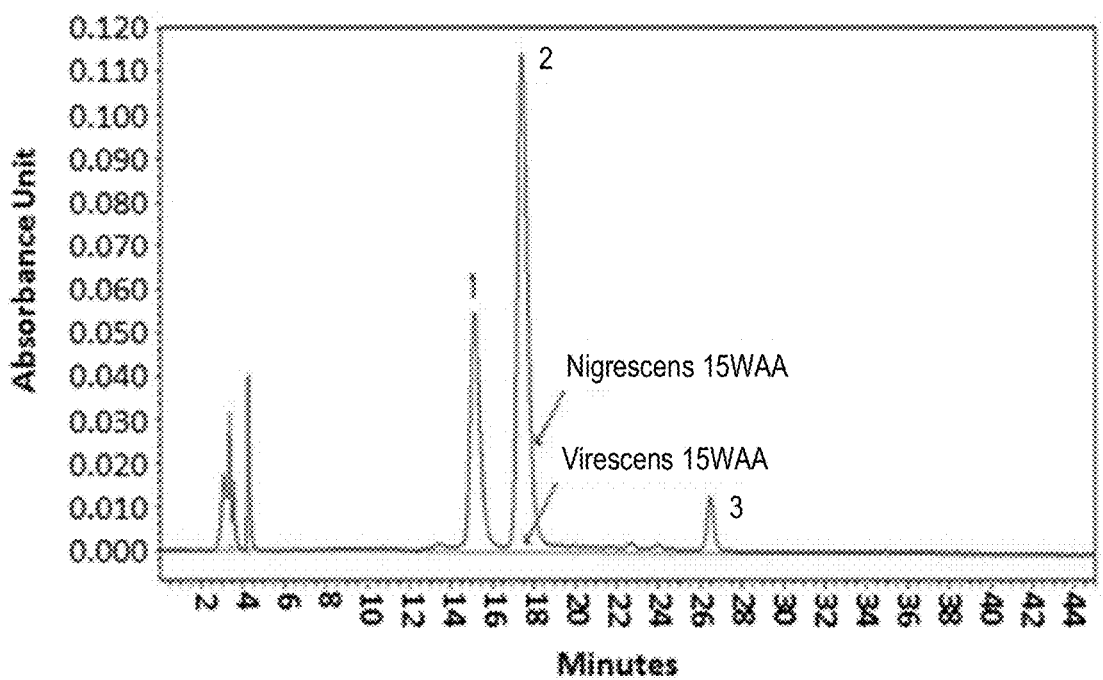

In order to examine anthocyanin deficiency in *virescens* fruits, we performed a combination of metabolic and gene expression analyses. Spectrophotometric and chromatographic (HPLC) analyses of acidified methanol extracts of exocarp confirmed the presence of anthocyanins in *nigrescens*, but absence in *virescens* fruit (FIG. 10*a-c*). Gene expression in *nigrescens* and *virescens* whole fruits at 8 weeks after anthesis (WAA) was analyzed by transcriptome sequencing (Table 7). The oil palm fruit typically exhibits biphasic growth with an initial growth spurt between approximately 4 to 9 WAA. Further, significant biochemical changes are observed starting at 8 WAA and up to 10 WAA during the transition phase between a metabolic sink and a storage sink (Kok, S. Y. et al. *J. Plant Res.* 126, 539-547 (2013)). Therefore, 8 WAA was chosen to examine expression of anthocyanin biosynthetic genes, avoiding later stages when expression of other mesocarp genes occurs that share the phenylpropanoid pathway, such as those involved in polyphenol biosynthesis.

TABLE 7

Samples used for transcriptome sequencing

| Plant ID | Fruit Colour Phenotype | Stage | Tissue Type |
| --- | --- | --- | --- |
| 0.482/6 | Nigrescens | 8WAA | Whole Fruit |
| 0.482/6 | Nigrescens | 8WAA | Whole Fruit |
| 0.482/6 | Nigrescens | 8WAA | Whole Fruit |
| 0.482/8 | Nigrescens | 8WAA | Whole Fruit |
| 0.482/8 | Nigrescens | 8WAA | Whole Fruit |
| 0.482/8 | Nigrescens | 8WAA | Whole Fruit |
| 0.481/350 | Virescens | 8WAA | Whole Fruit |
| 0.481/350 | Virescens | 8WAA | Whole Fruit |
| 0.481/350 | Virescens | 8WAA | Whole Fruit |

Figure 10D:
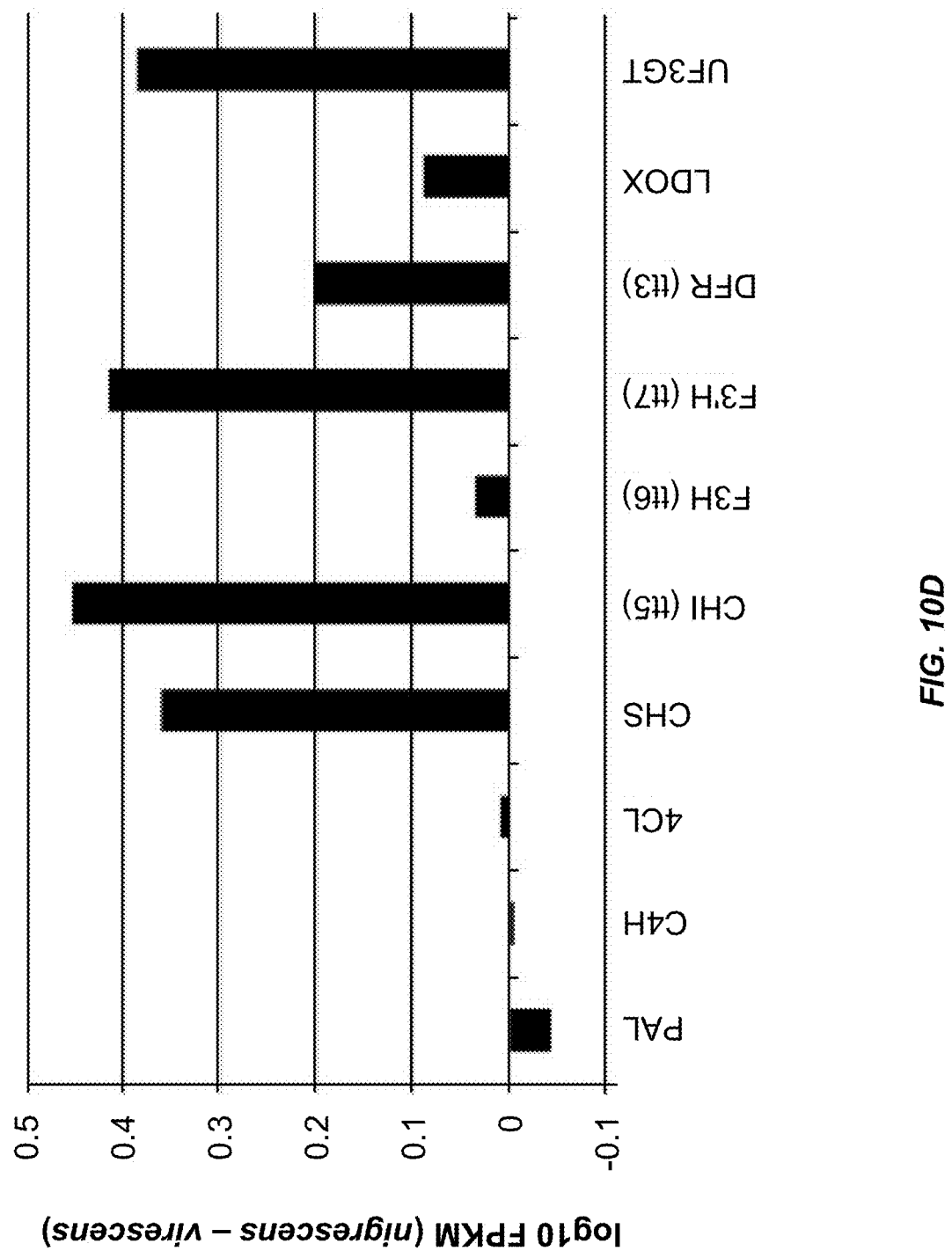

Transcriptome reads with substantial sequence similarity to each biosynthetic gene in the *Arabidopsis* anthocyanin phenylpropanoid pathway were identified (Tables 7 and 8). Flavonoid enzymes can be divided into "early" and "late" groups that regulate distinct temporal stages of the pathway (Pelletier, M. K., et al. Plant Physiol. 113, 1437-1445 (1997)). However, the point in the pathway at which the early and late stages divide differs among various plant species. For example, in *Arabidopsis* seedlings, the late genes initiate at the F3'H step, with downstream genes being regulated by Myb/bHLH/WD-repeat proteins (Gonzales. A. et al. Plant J. 53, 814-827 (2008)) while in maize aleurone, the early/late split occurs at CHS, farther upstream in the pathway (Taylor and Briggs, *Plant Cell* 2, 115-127 (1990)). At 8 WAA, *nigrescens* fruits display dramatically higher expression of CHS and all later pathway genes (FIG. 10*d*). These results suggest that the truncating VIR mutations result in dominant inhibition of Myb-regulated target genes beginning at CHS and extending throughout the anthocyanin biosynthetic pathway, implying a late gene group similar to that in the maize aleurone.

TABLE 8

Transcriptome sequence analysis of *nigrescens* vs. *virescens* fruits

| Gene name[a] | Number of genes included[b] | nigrescens[c] | virescens[c] | Difference (nigrescens-virescens)[d] |
| --- | --- | --- | --- | --- |
| Vir | 1 | 0.737 | 0.138 | 0.599 |
| PAL | 10 | 0.217 | 0.261 | −0.044 |
| C4H | 26 | 0.956 | 0.961 | −0.005 |
| 4CL | 14 | 0.396 | 0.387 | 0.009 |
| CHS | 4 | −1.011 | −1.372 | 0.361 |
| CHI TT5 | 24 | 1.977 | 1.523 | 0.454 |
| F3H TT6 | 13 | 0.721 | 0.685 | 0.036 |
| DFR TT3 | 13 | 0.737 | 0.534 | 0.204 |
| LDOX | 18 | 0.590 | 0.501 | 0.089 |
| UF3GT | 57 | −0.391 | −0.778 | 0.387 |

[a]Biosynthetic genes in the *Arabidopsis* anthocyanin phenylpropanoid pathway
[b]Indicates the number of *E. guineensis* gene models that were grouped into each pathway gene group.
[c]Mean of $\log_{10}$ expression measured in fragments per thousand mapped reads (FPKM) as calculated by CUFFLINKS. To establish a limit of detection, a value of 0.00001 was added to each FPKM value.
[d]Mean of $\log_{10}$ FPKM for *nigrescens* fruits minus that for *virescens* fruits. Positive values represent higher expression in *nigrescens*, relative to *virescens*, fruits.

Discussion

Our findings establish that the oil palm VIR gene controls fruit colour and that any one of five independent, but closely related, dominant mutations in the gene can cause the *virescens* fruit colour phenotype (FIG. 11). The discovery of the genetic basis of the *virescens* phenotype paves the way for development of genetic testing for fruit colour well before planting and for the introgression of the desirable trait into elite breeding materials. For example, the identification of the VIR gene allows differentiation of the homozygous and heterozygous forms of *virescens* palms, as early as the seedling stage, and together with the recent identification of SHELL (Singh, R. et al. *Nature* 500, 340-344 (2013)), allows breeders to develop parental (*pisifera*) lines that are homozygous for *virescens* for use in breeding programmes or for commercial seed production. All 5 alleles of VIR from equatorial Africa have C-terminal frameshifts and stop codons, and their prevalence is unprecedented. This likely reflects dominant negative inheritance (which makes novel alleles conspicuous) and cultural practices that retain the alleles for ritual purposes. The utility of these alleles will have important impacts on fruit harvesting practices, to improve oil yields and lead to improved land utilization.

SEQ ID NO:1 is the genomic interval of VIR in a *nigrescens* palm from the T-128 cross, including 182 bp 5' of the start codon, 2,445 bp comprising the introns and exons of the gene, and 713 bp 3' of the wild type stop codon.

SEQ ID NO:2 is the nucleotide coding sequence of the wild-type VIR gene from the start codon to the stop codon.

SEQ ID NO:3 is the expressed sequence of the VIR gene in a *nigrescens* plant including predicted 5' and 3' UTR sequence.

SEQ ID NO:4 is the predicted amino acid translation of the wild-type VIR polypeptide.

SEQ ID NO:5 is the predicted amino acid translation of the VIR Event 1 mutation, which was discovered in *viriscens* palms in the T128 segregating cross.

SEQ ID NO:6 is the observed partial nucleotide coding sequence of VIR Event 1 mutation.

SEQ ID NO:7 is the reconstructed complete coding sequence of VIR Event 1 mutation.

SEQ ID NO:8 is the amino acid translation of the VIR Event 2 mutation.

SEQ ID NO:9 is the reconstructed complete coding sequence of VIR Event 2 mutation.

SEQ ID NO:10 is the amino acid translation of the VIR Event 3 mutation.

SEQ ID NO:11 is the reconstructed complete coding sequence of VIR Event 3 mutation.

SEQ ID NO:12 is the amino acid translation of the VIR Event 4 mutation.

SEQ ID NO:13 is the reconstructed complete coding sequence of VIR Event 4 mutation.

SEQ ID NO:14 is the amino acid translation of the VIR Event 5 mutation.

SEQ ID NO:15 is the reconstructed complete coding sequence of VIR Event 5 mutation.

SEQ ID NO:16 is the genomic interval sequence of the VIR gene in a *viriscens* plant.

SEQ ID NO:17 is an approximately 2 megabase pair long genomic interval from the reference genome sequence of a congo derived *pisifera* palm around the VIR gene where the first base of the start codon is at position 1,000,001, and there is roughly a megabase 5' and 3' flanking the gene.

Example 2

Differential Detection of Wild-type and Event 2 VIR Alleles

A subset of VIR exon 3 including the Event 2 point mutation is shown in FIG. 12a. The G-to-T point mutation is indicated by the lower case "t" in the figure panel. The Event 2 nonsense mutation creates an AseI restriction enzyme recognition sequence (boxed bases in FIG. 12a). As shown in the figure, PCR primers (denoted by arrows) can be designed to amplify the surrounding sequence so that the amplicon includes only one potential AseI site, and this site is only present on alleles including the vir$^{Event2}$ nonsense mutation. Using the primers suggested in the figure, PCR amplification results in a 340 bp amplicon. As shown in the prophetic example in FIG. 12b, amplicons can be split into two portions: the first portion is mock-treated without restriction enzyme (NE) and the second portion is digested with AseI. Following gel electrophoresis, all NE portions will have a single 340 bp band. Amplicons derived from VIR/VIR genomic DNA will have a single 340 bp band in both the NE and the AseI lanes. Amplicons derived from VIR/vir$^{Event2}$ genomic DINA will have a single 340 bp band in the NE lane and three bands (340, 189 and 151 bp) in the AseI lane: 340 bp derived from the VIR allele and 189 and 151 bp obtained by AseI digestion of the vir$^{Event2}$ allele. Amplicons derived from vir$^{Event2}$/vir$^{Event2}$ genomic DNA will have a single 340 bp band in the NE lane and two bands (189 and 151 bp) in the AseI lane. Therefore, this type of assay can be used to determine the VIR genotype of a DINA or RNA (via reverse-transcriptase PCR) sample and detect the heterozygous or homozygous presence of the vir$^{Event2}$ mutation.

Figure 13:
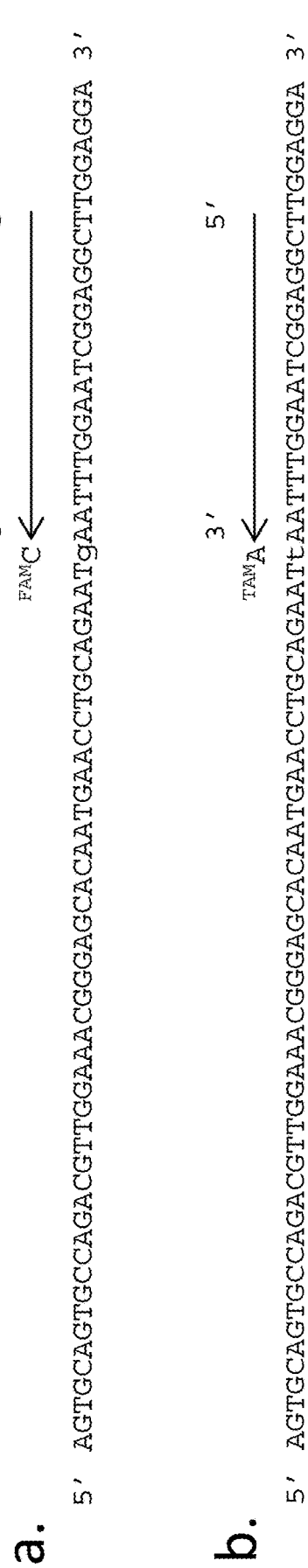
FIG. 13: Single nucleotide primer extension-based assay for genotyping the vir$^{Event2}$ allele. a, Depicts an exemplary primer (SEQ ID NO:72) and primer extension product (SEQ ID NO:73) for detecting the wild-type VIR allele (template=SEQ ID NO:71). The primer extension product contains a 3' cytosine nucleotide linked to a detectable fluorescein derivative, denoted as $^{FAM}$C. b, Depicts an exemplary primer (SEQ ID NO:72) and primer extension product (SEQ ID NO:75) for detecting the vir$^{Event2}$ allele (template=SEQ ID NO:74). The primer extension product contains a 3' adenine nucleotide linked to a detectable rhodamine derivative, denoted as $^{TAM}$A (TAMRA). Thus plants containing a a VIR/VIR, VIR/vir$^{Event2}$, or vir$^{Event2}$/vir$^{Event2}$ genotype can be differentially detected.

Alternatively, the Event 2 mutation can be genotyped by single nucleotide primer extension, thus not relying upon restriction enzyme recognition sequences or restriction digestion. As shown in FIG. 13, a primer can be designed so that its 3' terminal is complimentary to the nucleotide one base 3' of the polymorphic nucleotide. Single nucleotide primer extension is carried out with a mixture of dideoxyribonucleotides (ddATP, ddCTP, ddGTP, ddTTP), each labeled with a different fluorophore. For example, primer annealed to a VIR allele (G at the polymorphic position) could be extended by a single C tagged with FAM (FIG. 13a). Alternatively, primer annealed to a vir$^{Event2}$ allele (T at the polymorphic position) could be extended by a single A tagged with TAM (TAMRA) (FIG. 13b). Therefore, this type of assay can be used to determine the VIR genotype of a DNA or RNA (via reverse-transcriptase PCR) sample and detect the heterozygous or homozygous presence of the vir$^{Event2}$ mutation.

Example 3

Differential Detection of Wild-Type and Event 3 VIR Alleles

Figure 14:
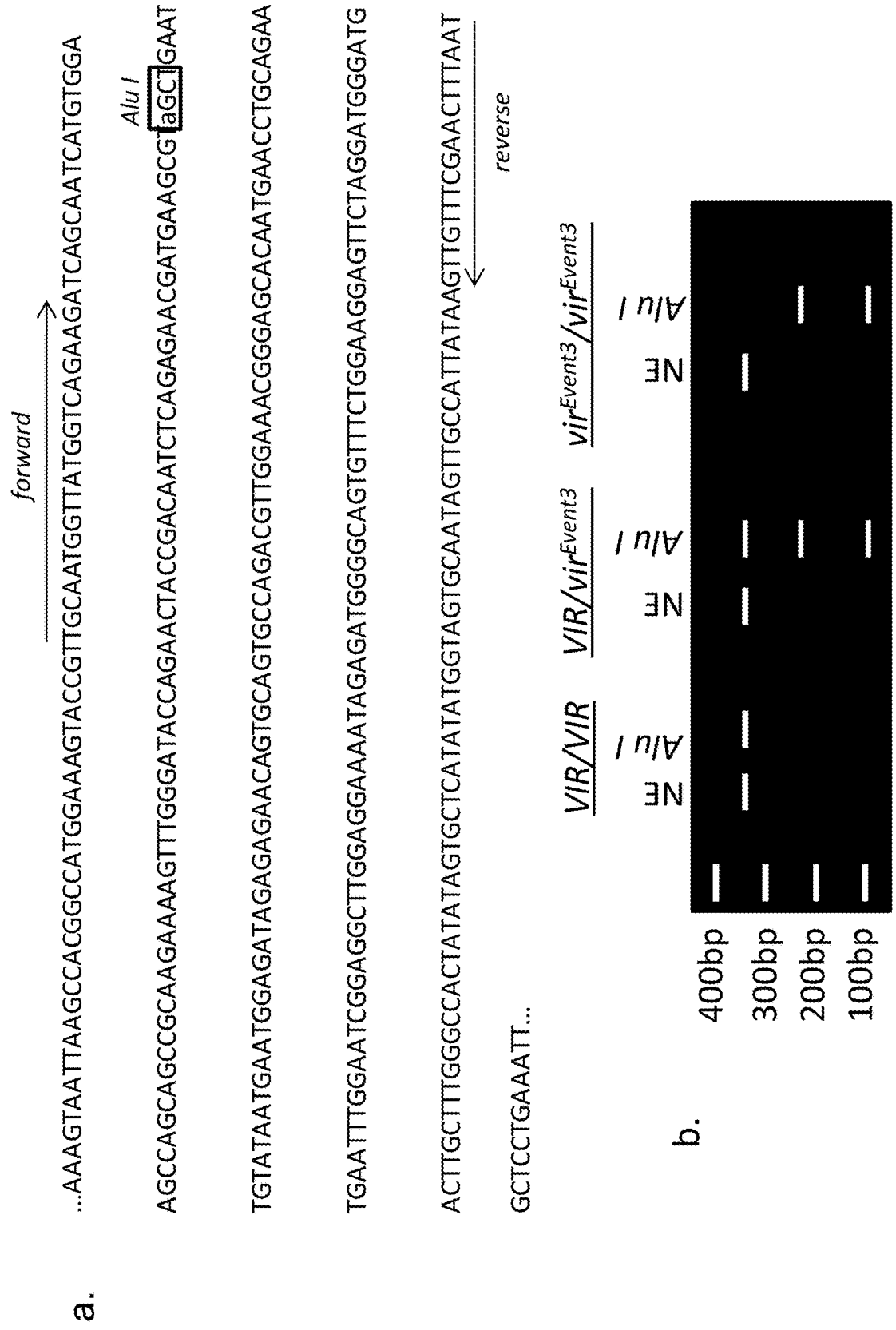
FIG. 14: Restriction enzyme-based assay for genotyping the vir$^{Event3}$ allele, a, Depicts the AluI cleavage site present in the vir$^{Event3}$ allele (SEQ ID NO:76) and binding sites for forward (SEQ ID NO:77) and reverse (SEQ ID NO:78) amplification primers. b, Depicts the results from amplifying the region flanked by the forward and reverse primers denoted in a to produce an amplicon, digesting a portion of the amplicon with AluI, and separating both the digested portion and an undigested portion by gel electrophoresis to differentially detect plants containing a VIR/VIR, VIR/vir$^{Event3}$, or vir$^{Event3}$/vir$^{Event3}$ genotype.

A subset of VIR exon 3 including the Event 3 point mutation is shown in FIG. 14a. The G-to-A point mutation is indicated by the lower case "a" in the figure panel. The Event 3 nonsense mutation creates an AluI restriction enzyme recognition sequence (boxed bases in FIG. 14a). As shown in the figure. PCR primers (denoted by arrows) can be designed to amplify the surrounding sequence so that the amplicon includes only one potential AluI site, and this site is only present on alleles including the vir$^{Event3}$ nonsense mutation. Using the primers suggested in the figure, PCR amplification results in a 340 bp amplicon. As shown in the prophetic example in FIG. 14b, amplicons can be split into two portions: the first portion is mock-treated without restriction enzyme (NE) and the second portion is digested with AluI. Following gel electrophoresis, all NE portions will have a single 340 bp band. Amplicons derived from VIR/VIR genomic DNA will have a single 340 bp band in both the NE and the AluI lanes. Amplicons derived from VIR/vir$^{Event3}$ genomic DNA will have a single 340 bp band in the NE lane and three bands (340, 108 and 232 bp) in the AluI lane: 340 bp derived from the VIR allele and 108 and 232 bp obtained by AluI digestion of the vir$^{Event3}$ allele. Amplicons derived from vir$^{Event3}$/vir$^{Event3}$ genomic DNA will have a single 340 bp band in the NE lane and two bands (108 and 232 bp) in the AluI lane. Therefore, this type of assay can be used to determine the VIR genotype of a DNA or RNA (via reverse-transcriptase PCR) sample and detect the heterozygous or homozygous presence of the vir$^{Event3}$ mutation.

Alternatively, the Event 3 mutation can be genotyped by single nucleotide primer extension, thus not relying upon restriction enzyme recognition sequences or restriction digestion. As shown in FIG. 15, a primer can be designed so that its 3' terminal is complimentary to the nucleotide one base 5' of the polymorphic nucleotide. Single nucleotide primer extension is carried out with a mixture of dideoxyribonucleotides (ddATrP, ddCTP, ddGTP, ddTTP), each labeled with a different fluorophore. For example, primer annealed to a VIR allele (G at the polymorphic position) could be extended by a single C tagged with FAM (FIG. 15a). Alternatively, primer annealed to a vir$^{Event3}$ allele (A at the polymorphic position) could be extended by a single T tagged with TAM (TAMRA) (FIG. 15b). Therefore, this type of assay can be used to determine the VIR genotype of a DNA or RNA (via reverse-transcriptase PCR) sample and detect the heterozygous or homozygous presence of the vir$^{Event3}$ mutation.

Example 4

Differential Detection of Wild-Type and Event 5 VIR Alleles

Figure 12:
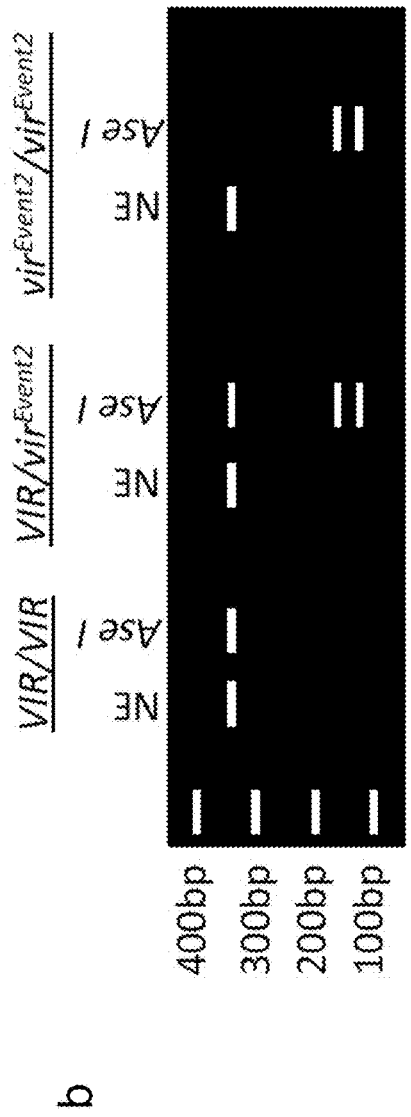
FIG. 12: Restriction enzyme-based assay for genotyping the vir$^{Event2}$ allele. a, Depicts the AseI cleavage site present in the vir$^{Event2}$ allele (SEQ ID NO:68) and binding sites for forward (SEQ ID NO:69) and reverse (SEQ ID NO:70) amplification primers. b, Depicts the results from amplifying the region flanked by the forward and reverse primers denoted in a to produce an amplicon, digesting a portion of the amplicon with AseI, and separating both the digested portion and an undigested portion by gel electrophoresis to differentially detect plants containing a VIR/VIR, VIR/vir$^{Event2}$, or vir$^{Event2}$/vir$^{Event2}$ genotype.

A subset of VIR exon 3 including the Event 5 rearrangement mutation is shown in FIG. 16a. The rearrangement creates a unique DNA sequence beginning at the vertical arrow in FIG. 16a. The same forward primer as shown in FIG. 12 can be used in combination with a reverse primer unique to the Event 5 allele to generate a 137 bp amplicon only from genomic DNA containing at least one Event 5 allele. A third reverse primer, as shown in FIG. 12, in combination with the common forward primer would generate a 340 bp amplicon only from genomic DNA containing the VIR allele. The Event 5 mutation introduces a unique AseI restriction enzyme site in the 137 bp amplicon that is not present in the 340 bp VIR amplicon. As shown in the prophetic example in FIG. 16b, amplicons can be split into two portions: the first portion is mock-treated without restriction enzyme (NE) and the second portion is digested with AseI. Following gel electrophoresis, amplicons derived from VIR/VIR genomic DNA will have a single 340 bp band in both the NE and the AseI lanes. Amplicons derived from VIR/vir$^{Event5}$ genomic DNA will have a 340 bp band and a 137 bp band in the NE lane and three bands (340, 78 and 59 bp) in the AseI lane: 340 bp derived from the VIR allele and 78 and 59 bp obtained by AseI digestion of the vir$^{Event5}$ allele. Amplicons derived from vir$^{Event5}$/vir$^{Event5}$ genomic DNA will have a single 137 bp band in the NE lane and two bands (78 and 59 bp) in the AseI lane. Therefore, this type of assay can be used to determine the VIR genotype of a DNA or RNA (via reverse-transcriptase PCR) sample and detect the heterozygous or homozygous presence of the vir$^{Event5}$ mutation.

Figure 17:
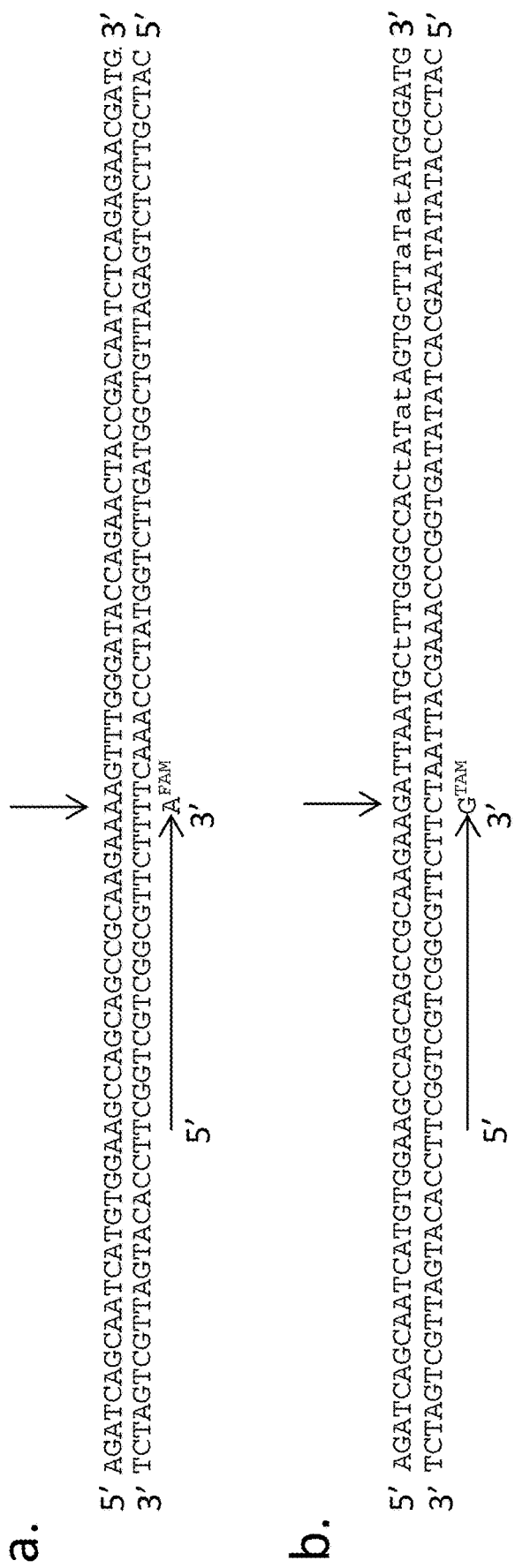
FIG. 17: Single nucleotide primer extension-based assay for genotyping the vir$^{Event5}$ allele. a, Depicts an exemplary primer (SEQ ID NO:89) and primer extension product (SEQ ID NO:90) for detecting the wild-type VIR allele (template=SEQ ID NO:87; complement=SEQ ID NO:88). The primer extension product contains a 3' thymine nucleotide linked to a detectable fluorescein derivative, denoted as A$^{FAM}$ b, Depicts an exemplary primer (SEQ ID NO:89) and primer extension product (SEQ ID NO:90) for detecting the vir$^{Event5}$ allele (template=SEQ ID NO:91; complement=SEQ ID NO:92). The primer extension product contains a 3' cytosine nucleotide linked to a detectable rhodamine derivative, denoted as G$^{TAM}$ (TAMRA). Thus plants containing a VIR/VIR, VIR/vir$^{Event5}$, or vir$^{Event5}$/vir$^{Event5}$ genotype can be differentially detected.

Alternatively, the Event 5 mutation can be genotyped by single nucleotide primer extension, thus not relying upon restriction enzyme recognition sequences or restriction digestion. As shown in FIG. 17, the sequence of VIR (FIG. 17a) and vir$^{Event5}$ (FIG. 17b) diverge at the nucleotide denoted by the downward pointing arrow. A common primer can be designed so that its 3' terminal is complimentary to the nucleotide one base 3' of the polymorphic nucleotide and the sequence of the primer is complimentary to both VIR and vir$^{Event5}$ sequence. Single nucleotide primer extension is carried out with a mixture of dideoxyribonucleotides (ddATP, ddCTP, ddGTP, ddTTP), each labeled with a different fluorophore. For example, primer annealed to a VIR allele (T at the first diverging position on the 3' to 5' strand shown in FIG. 17a)) could be extended by a single adenine tagged with FAM (FIG. 17a). Alternatively, primer annealed to a vir$^{Event5}$ allele (C at the first diverging position on the 3' to 5' strand shown in FIG. 17b)) could be extended by a single guanine tagged with TAM (TAMRA) (FIG. 17b). Therefore, this type of assay can be used to determine the VIR genotype of a DNA or RNA (via reverse-transcriptase PCR) sample and detect the heterozygous or homozygous presence of the vir$^{Event5}$ mutation.

Example 5

Differential Detection of Wild-Type, Event 1, and Event 4 VIR Alleles

Figure 18:
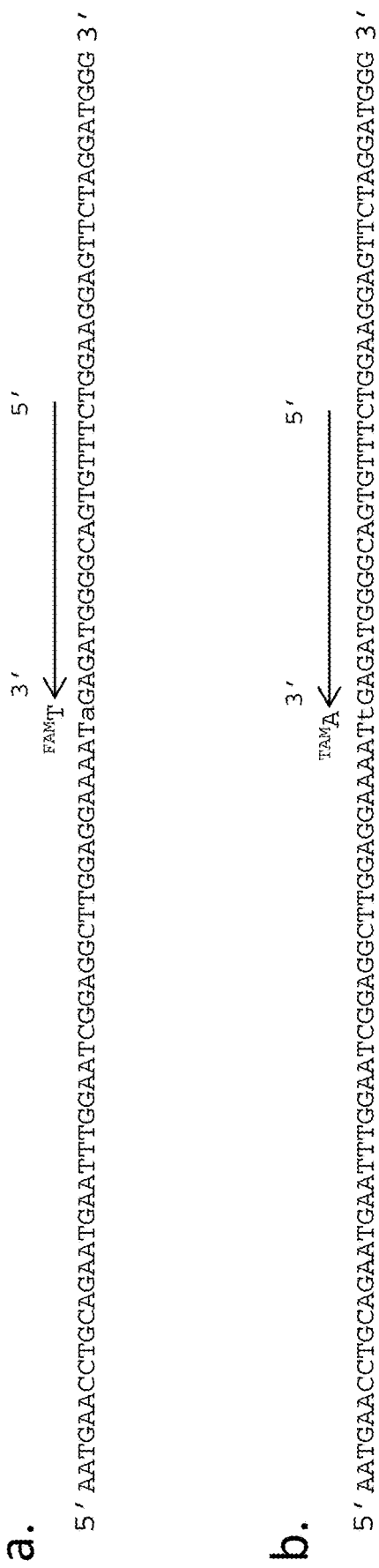
FIG. 18: Single nucleotide primer extension-based assay for genotyping the vir$^{Event1}$ allele. a, Depicts an exemplary primer (SEQ ID NO:95) and primer extension product (SEQ ID NO:96) for detecting the wild-type VIR allele (template=SEQ ID NO:94). The primer extension product contains a 3' thymine nucleotide linked to a detectable fluorescein derivative, denoted as $^{FAM}$T. b, Depicts an exemplary primer (SEQ ID NO:95) and primer extension product (SEQ ID NO:98) for detecting the vir$^{Event1}$ allele (template=SEQ ID NO:97). The primer extension product contains a 3' adenine nucleotide linked to a detectable rhodamine derivative, denoted as $^{TAM}$A (TAMRA). Thus plants containing a VIR/VIR, VIR/vir$^{Event1}$, or vir$^{Event1}$/vir$^{Event1}$ genotype can be differentially detected.

The Event 1 mutation can be genotyped by single nucleotide primer extension, thus not relying upon restriction enzyme recognition sequences or restriction digestion. As shown in FIG. 18, a primer can be designed so that its 3' terminal is complimentary to the nucleotide one base 3' of the polymorphic nucleotide. Single nucleotide primer extension is carried out with a mixture of dideoxyribonucleotides (ddATP, ddCTP, ddGTP, ddTTP), each labeled with a different fluorophore. For example, primer annealed to a VIR allele (A at the polymorphic position) could be extended by a single thymine tagged with FAM (FIG. 18a). Alternatively, primer annealed to a vir$^{Event1}$ allele (T at the polymorphic position) could be extended by a single adenine tagged with TAM (TAMRA) (FIG. 18b). Therefore, this type of assay can be used to determine the VIR genotype of a DNA or RNA (via reverse-transcriptase PCR) sample and detect the heterozygous or homozygous presence of the vir$^{Event1}$ mutation.

Figure 19:
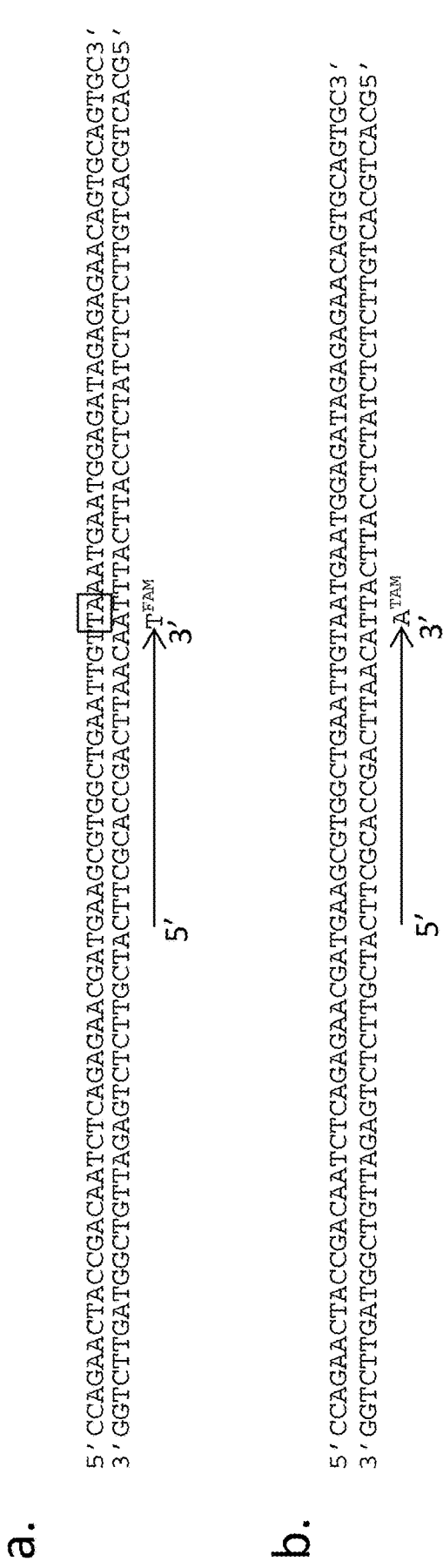
FIG. 19: Single nucleotide primer extension-based assay for genotyping the vir$^{Event4}$ allele. a, Depicts an exemplary primer (SEQ ID NO:101) and primer extension product (SEQ ID NO:102) for detecting the wild-type VIR allele (template=SEQ ID NO:99; complement=SEQ ID NO:100). The primer extension product contains a 3' adenine nucleotide linked to a detectable fluorescein derivative, denoted as T$^{FAM}$. b, Depicts an exemplary primer (SEQ ID NO:101) and primer extension product (SEQ ID NO:105) for detecting the vir$^{Event4}$ allele (template=SEQ ID NO:103; complement=SEQ ID NO:104). The primer extension product contains a 3' thymine nucleotide linked to a detectable rhodamine derivative, denoted as A$^{TAM}$ (TAMRA). Thus plants containing a VIR/VIR, VIR/vir$^{Event4}$, or vir$^{Event4}$/vir$^{Event4}$ genotype can be differentially detected.

Similarly, the Event 4 mutation can be differentially detected by single nucleotide primer extension. The vir$^{Event4}$ mutation is a deletion of 2 bases (TA) relative to VIR. These two bases are boxed in FIG. 19a. For example, primer annealed to a VIR allele one base 3' to the TA sequence deleted in vir$^{Event4}$ could be extended by a single thymine tagged with FAM (FIG. 19a). Alternatively, the same primer annealed to a vir$^{Event4}$ allele could be extended by a single adenine tagged with TAM (TAMRA) (FIG. 19b). Therefore, this type of assay can be used to determine the VIR genotype of a DNA or RNA (via reverse-transcriptase PCR) sample and detect the heterozygous or homozygous presence of the vir$^{Event4}$ mutation.

Thus, all known naturally occurring variations of the VIR locus can be detected. Consequently, the genotype of an oil palm plant at the VIR locus can be determined and the fruit color phenotype predicted. Moreover, additional naturally occurring or induced variations at the VIR locus can be detected using methods described herein or known in the art to predict the fruit color phenotype of an oil palm plant.

The term "a" or "an" is intended to mean "one or more." The term "comprise" and variations thereof such as "comprises" and "comprising," when preceding the recitation of a step or an element, are intended to mean that the addition of further steps or elements is optional and not excluded. All patents, patent applications, and other published reference materials cited in this specification are hereby incorporated herein by reference in their entirety.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10669593B2). An electronic copy of the "Sequence Listing" will also be available from the USPTO upon request and payment of the fee set forth in 37 CFR 1.19(b)(3).

What is claimed is:

1. A method for determining a fruit color phenotype of an *E. guineensis* palm plant, the method comprising,
providing a sample from an *E. guineensis* palm plant or seed;
detecting in the sample presence or absence of a VIR gene alteration in a genomic region corresponding to SEQ ID NO:1 that comprises a VIR gene and confers a *virescens* phenotype to fruit, wherein the detecting comprises detecting the VIR gene alteration by amplification, hybridization, or nucleotide sequencing, wherein the gene alteration in causes the *virescens* phenotype, wherein the VIR gene alteration comprises a nucleotide change that results in a premature stop codon; and
segregating the *E. guineensis* palm plant or seed into groups based on the presence of the VIR gene alternation, wherein at least one group contains *E. guineensis* palm plants or seeds having the VIR gene alteration in the genomic region corresponding to SEQ ID NO: 1.

2. The method of claim 1, wherein the VIR gene alteration generates a truncated protein compared to the protein encoded by SEQ ID NO:4.

3. The method of claim 1 wherein the VIR gene alteration results in the sequence of any one of SEQ ID NOS:7, 9, 11, 13, and 15, or the VIR gene alteration results in a sequence that encodes an amino acid sequence selected from the group consisting of SEQ ID NOS:5, 8, 10, 12, and 14.

4. The method of claim 1, wherein the VIR gene encodes (i) a polypeptide at least 95% identical to SEQ ID NO:4.

5. The method of claim 1, wherein the plant is less than 5 years old.

6. The method of claim 1, wherein the plant is less than one year old.

7. The method of claim 1, further comprising selecting the *E. guineensis* palm plant or seed for cultivation if the *E. guineensis* palm plant or seed has the VIR gene alteration.

8. The method of claim 7, wherein the *E. guineensis* palm plant or seed is discarded if the *E. guineensis* palm plant or seed does not have the VIR gene alteration.

9. The method of claim 1, wherein the segregating comprises segregating the *E. guineensis* palm plant or seed into a first group based on the presence of the VIR gene alteration and segregating the *E. guineensis* palm plant or seed into a second group based on the absence of the VIR gene alteration.

10. The method of claim 9, wherein the absence of the VIR gene alteration results in a *nigrescens* phenotype.

11. The method of claim 1, wherein the method further comprises amplifying genomic DNA from the sample prior to the detecting.

12. A method for determining a fruit color phenotype of an *E. guineensis* palm plant, the method comprising,
providing a sample from an *E. guineensis* palm plant or seed;
detecting in the sample presence or absence of a VIR gene alteration in a genomic region corresponding to SEQ ID NO:1 that comprises a VIR gene and confers a *virescens* phenotype to fruit, wherein the gene alteration causes the *virescens* phenotype, wherein the VIR gene alteration results the sequence of any one of SEQ ID NOS:7, 9, 11, 13, and 15, wherein the detecting comprises detecting the VIR gene alteration by amplification, hybridization or nucleotide sequencing, wherein the VIR gene alteration comprises a nucleotide change that results in a premature stop codon; and
segregating the *E. guineensis* palm plant or seed into groups based on the presence of the VIR gene alternation, wherein at least one group contains *E. guineensis* palm plants or seeds having the VIR gene alteration in the genomic region corresponding to SEQ ID NO: 1.

13. The method of claim 1, wherein the detecting comprises obtaining the sequence of the VIR gene in the genomic region corresponding to SEQ ID NO:1.

14. The method of claim 1, wherein the detecting comprises obtaining the sequence of the VIR gene in the genomic region corresponding to SEQ ID NO:1.

* * * * *